US007285620B2

(12) United States Patent
Ponath et al.

(10) Patent No.: US 7,285,620 B2
(45) Date of Patent: *Oct. 23, 2007

(54) HUMAN CHEMOTACTIC CYTOKINE

(75) Inventors: Paul D. Ponath, Boston, MA (US); Shixin Qin, Lexington, MA (US); Douglas J. Ringler, Revere, MA (US); Walter Newman, Boston, MA (US); Charles Mackay, Newton Highlands, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/133,140

(22) Filed: May 19, 2005

(65) Prior Publication Data

US 2006/0141567 A1    Jun. 29, 2006

Related U.S. Application Data

(63) Continuation of application No. 08/494,093, filed on Jun. 23, 1995.

(51) Int. Cl.
C07K 14/52      (2006.01)
C12N 15/63      (2006.01)
(52) U.S. Cl. .................... 530/324; 435/69.5; 424/1.41
(58) Field of Classification Search ..................... None
See application file for complete search history.

(56) References Cited

U.S. PATENT DOCUMENTS

| 5,993,814 | A | 11/1999 | Williams et al. |
| 6,001,649 | A | 12/1999 | Caput et al. |
| 6,031,080 | A | 2/2000 | Williams et al. |
| 6,403,782 | B1 | 6/2002 | Luster et al. |
| 6,780,973 | B1 | 8/2004 | Luster et al. |

FOREIGN PATENT DOCUMENTS

| WO | WO90/07863 | 7/1990 |
| WO | WO95/07985 | 3/1995 |
| WO | WO96/25497 | 8/1996 |
| WO | WO97/12914 | 4/1997 |
| WO | WO97/46683 | 12/1997 |

OTHER PUBLICATIONS

Miller, M.D., et al., "Biology and Biochemistry of the Chemokines: A Family of Chemotactic and Inflammatory Cytokines," *Crit. Rev. Immunol.*, 12(1,2):17-46 (1992).
Baggiolini, M. and C.A. Dahinden, "CC Chemokines in Allergic Inflammation," *Immunol. Today*, 15(3):127-133 (1994).
Jose, P.J., et al., "Eotaxin: A Potent Eosinophil Chemoattractant Cytokine Detected in a Guinea Pig Model of Allergic Airways Inflammation," *J. Exp. Med.*, 179:881-887 (1994).
Jose, P.J., et al., "Eotaxin: Cloning of an Eosinophil Chemoattractant Cytokine and Increased mRNA Expression in Allergen-Challenged Guinea-Pig Lungs," *Biochem. Biophys. Res. Commun.*, 205(1):788-794 (1994).
Rothenberg, M.E. et al., "Constitutive and Allergen-induced Expression of Eotaxin mRNA in the Guinea Pig Lung," *J. Exp. Med.*, 181:1211-1216 (1995).
Tepper, R.I., et al., "Murine Interleukin-4 Displays Potent Anti-tumor Activity in Vivo," *Cell*, 57:503-512 (1989).
Kameyoshi, Y., et al., "Cytokine RANTES Released by Thrombin-stimulated Platelets Is a Potent Attractant for Human Eosinophils," *J. Exp. Med.*, 176:587-592 (1992).
Griffiths-Johnson, D.A., et al., "The Chemokine, Eotaxin, Activates Guinea-Pig Eosinophils In Vitro and Causes Their Accumulation into the Lung In Vivo," *Biochem. Biophys. Res. Commun.*, 197(3):1167-1172 (1993).
Rothenberg, M.E., et al., "Murine Eotaxin: An Eosinophil Chemoattractant Inducible in Endothelial Cells and in Interleukin 4-induced Tumor Suppression," *Proc. Natl. Acad. Sci. USA*, 92:8960-8964 (1995).
Kitaura, M., et al., "Molecular Cloning of Human Eotaxin, an Eosinophil-selective CC Chemokine, and Identification of a Specific Eosinophil Eotaxin Receptor, CC Chemokine Receptor 3," *J. Biol. Chem.*, 271(13):7725-7730 (1996).
Rot, A., et al., "RANTES and Macrophage Inflammatory Protein 1α Induce the Migration and Activation of Normal Human Eosinophil Granulocytes," *J. Exp. Med.*, 176(6):1489-1495 (1992).
Schröder, J.-M., et al., "Platelets Secrete and Eosinophil-Chemotactic Cytokine Which is a Member of the C-C-Chemokine Family," *Adv. Exp. Med. Biol.*, 351:119-128 (1993).
Wardlaw, A.J., et al., "Platelet-Activating Factor: A Potent Chemotactic and Chemokinetic Factor for Human Eosinophils," *J. Clin. Invest.*, 78:1701-1706 (1986).

(Continued)

Primary Examiner—Prema Mertz
(74) Attorney, Agent, or Firm—Hamilton, Brook, Smith & Reynolds, P.C.

(57) ABSTRACT

The invention relates to isolated and/or recombinant nucleic acids which encode a human chemotactic cytokine designated human eotaxin, and to isolated and/or recombinant human eotaxin proteins or polypeptides, including synthetic polypeptides. The invention further relates to recombinant nucleic acid constructs, comprising a nucleic acid which encodes a human eotaxin, a portion thereof, or a variant; to host cells comprising such constructs, useful for the production of recombinant human eotaxin; and to antibodies reactive with human eotaxin, useful in in vitro methods, diagnosis and/or therapy. Also provided are methods of use of the eotaxin proteins, e.g., in the recruitment of eosinophils to a particular site or in the treatment of allergic conditions. Human eotaxins can be used to identify inhibitors (e.g., antagonists) or promoters (agonists) of human eotaxin, which can be used to selectively modulate leukocyte function, in inflammatory and autoimmune diseases, or in infections.

18 Claims, 20 Drawing Sheets

OTHER PUBLICATIONS

Ponath, P.D., et al., "Cloning of the Human Eosinophil Chemoattractant, Eotaxin: Expression, Receptor Binding, and Functional Properties Suggest a Mechanism for the Selective Recruitment of Eosinophils," *J. Clin. Invest.*, 97(3):604-612 (1996).

Garcia-Zepeda, E.A., et al., "Human Eotaxin is a Specific Chemoattractant for Eosinophil Cells and Provides a New Mechanism to Explain Tissue Eosinophilia," *Nat. Med.*, 2(4):449-456 (1996).

Cunningham, B.C. and J.A. Wells, "High-Resolution Epitope Mapping of hGH-Receptor Interactions by Alanine-Scanning Mutagenesis," *Science*, 244:1081-1085 (1989).

George, D.G., et al., "Current Methods in Sequencing Comparison and Analysis," In *Macromolecular Sequencing and Synthesis*, D.H. Schlesinger, ed. (NY:Alan R. Liss, Inc.), Ch. 12, pp. 127-149 (1988).

Watarai, H., et al., "Posttranslational Modification of the Glycosylation Inhibiting Factor (GIF) Gene Product Generates Bioactive GIF," *Proc. Natl. Acad. Sci. USA*, 97(24):13251-13256 (2000).

Tomura, T., et al., "Immunosuppressive Activities of Recombinant Glycosylation-Inhibiting Factor Mutants," *J. Immunol.*, 162:195-202 (1999).

Kleemann, R., et al., "Characterization of Catalytic Centre Mutants of Macrophage Migration Inhibitory Factor (MIF) and Comparison to Cys81Ser MIF," *Eur. J. Biochem.*, 261:753-766 (1999).

Mikayama, T., et al., "Molecular Cloning and Functional Expression of a cDNA Encoding Glycosylation-Inhibiting Factor," *Proc. Natl. Acad. Sci. USA*, 90:10056-10060 (1993).

Voet, D and Voet, J.G., *Biochemistry*, John Wiley & Sons, Inc. p. 126-128 and 228-234 (1990).

Holst, B., et al., "Steric Hindrance Mutagenesis versus Alanine Scan in Mapping of Ligand Binding Sites in the Tachykinin $NK_1$ Receptor,"*Mol. Pharmacol.*, 53:166-175 (1998).

TCAAGACACAGTGTACACAGGAATCAAGGAAGGTCTTAGATCGACTCATCCCCCA
AGGCCTTGGTTTCCTTGCTCCTTTCCCCAACTACAGGTGTTTCATTTCAACTCAT
CCCCTAGGGCCTTGGTTTTCTTGCTCTCTTCCCCCACTACAGATGTTTAACTTCA
TTTCATAACCACATATTCCCCTCCTTTTCCAAGGCAAGATCCAGATGGATTAAAA
AATGTACCAAGTCCCTACTAGCTTGCCTCTCTTCTGTTCTGCTTGACTTCCTAGG
ATCTGGAATCTGGTCAGCAATCAGGAATCCCTTCATCGTGACCCCCGCATGGGCA
AAGGCTTCCCTGGAATCTCCCACACTGTCTGCTCCCTATAAAGGCAGGCAGATG
GGCCAGAGGAGCAGAGAGGCTGAGACCAACCCAGAAACCACCACCTCTCACGCCA
AAGCTCACACCTTCAGCCTCCAACATGAAGGTCTCCGCAGCACTTCTGTGGCTGC
                               M  K  V  S  A  A  L  L  W  L
TGCTCATAGCAGCTGCCTTCAGCCCCAGGGGCTCGCTGGGCCAGGTAAGCCCCC
L  L  I  A  A  A  F  S  P  Q  G  L  A  G  P
CAACTCCTTACAGGAAAGGTAAGGTAACCACCTCCAGAGCTACTAGGTCAGCAAG
AATCTTTACAGACTCACTGCAAATTCTCCATTTGAAAATAGGGAAACAGGTTTT
GTGGGTGGACAAGAAATGCCTCAACCTCACATCCAGTCACTGGAAGAGCCAGAAC
TAGAAAGCTCCCGAGTCTTTTCCCCACATTCAAGAGGGTTGCTGGGCGCATCCTT
ACCCAGCTATCCTCACAGTGTTTGGGAATGGGGAATGGCTCTGTCTTACTGTGGG
CATGGTGGGCATTTTTGGCAGTGGGAGAGAAGGAAAATCTGTTGATTAGAAGCTC
AGTATGTTAATTCGACTCCAGGACAGCTTTCAGAGACAGTGGCTAAGAGAGAAGA
ACGAGGTCCCAGGGGATCTCTTGAGGTGACTTATTTTGACACTCTTTGGGAAAC
GTTATCTAGGAGATTTGTTCCATAACTCATTTTCCCATACTCTGGTGACAAATTT
ACTGAGTGTATCGGTCCCACTGAGCCAGTGCATAGCATGGTAACAAACAGTCTAA
ATTATCAATGACTTAACAGAATTAACTAAATTAACAAAAGTTACTTTCTCACTTG
TACTAAATATCTATAATGTATGGGCTCAGGCTTCTGCATTTTATACTCAGGATTC
TAGACTGATGGAGAAGTTGCCCATGTGGGGAACATTGATGGATACTGTGATAAG
CAGAAGAAGCTCTCAGGAGTCTTGCATAGGCAATGCACTGTGGCTCAAAAATGAC
ACCCATCACTTTGTCTCCTTCTTTATTGATCAAAACTAATTAATGCCTCCAACCA
AACAAAAGTGGCCAAGAAATGCAAGTCTACCTTGTGTCTCAAAACAGAGGATGGA

FIG. 1A

GATATTTGGTGAAAATTACCATGACCATCACATGGCCACGTAGGTCTTTATAATG

ACAGGCTAGCATTTGTCACATTGACCAAGCTTTGTCCATACACTCTACAGTAATG

ATGAGTCCTCAGTGCACAGGGGAGGATGCTGAAGAGACAGGACAGCATCCTCCAG

ACACATTTGACTTCAGAGCAGAGGGATTCTCCCTCCACCTCTCGCAATTCCTTGC

TTTCTCCTAACTTCCTTTACAAAGTCATGCTTGGAAATGTCTATGTATCATCATG

TGGCTCATTTTTTTCTCTGTTCATTTTTTTCCCCAAAATTCAGCTTCTGTCCCA
                                                              A   S   V   P

ACCACCTGCTGCTTTAACCTGGCCAATAGGAAGATACCCCTTCAGCGACTAGAGA
 T   T   C   C   F   N   L   A   N   R   K   I   P   L   Q   R   L   E

GCTACAGGAGAATCACCAGTGGCAAATGTCCCCAGAAAGCTGTGATGTAAGTAAA
 S   Y   R   R   I   T   S   G   K   C   P   Q   K   A   V   I

TAAAGTTCACCCTCCCCTAGACAAAAAATAATGTCTAGGGCACAGAGTCAAGAA

CTGTGTCACAGTTGCTGGGAGTCATAGACTCTGATAGTTTGACCTCTATGGTCCA

ATTCATTAATTTTCACAAGTGTGTGCACTCCCAGCTCCCTGCCTGGGAGATTCGT

GTAGTCATATCAATTTCTTCAAGTCAAGAGCAAAGATGGTTTTACTGGGCCTTTA

AGAGCAGCAACTAACCCAAGAGTCTCATCCTTCCTCCTCTCCGTAGCAACCCTTT

GTCCAGGGGCAGATGGTCCTTAAATATTTAGGGTCAAATGGGCAGAATTTTCAAA

AACAATCCTTCCAATTGCATCCTGTATCTCCCACAGCTTCAAGACCAAACTGGCC
                                                   F   K   T   K   L   A

AAGGATATCTGTGCCGACCCCAAGAAGAAGTGGGTGCAGGATTCCATGAAGTATC
 K   D   I   C   A   D   P   K   K   K   W   V   Q   D   S   M   K   Y

TGGACCAAAAATCTCCAACTCCAAAGCCATAAATAATCACCATTTTTGAAACCAA
 L   D   Q   K   S   P   T   P   K   P   *

ACCAGAGCCTGATGTTGCCTAATTTGTTTTCCCTTCTTACAATGCATTCTGAGGT

AACCTCATTATCAGTCCAAAGGGCATGGGTTTTATTATATATATATATATTTTTT

TTTTAAAAAAAAACGTATTGCATTTAATTTATTGAGGCTTTAAAACTTATCCTCC

ATGATATCAGTTATTTTTAAACTGTAAGCTTTGTCAGATTCTTTACCCCCTGGGA

GCCCCAATTCGATCCCCTGTCACGTGAACCCAAAGTGTGACTCATTAAATGGAAG

TAAATGTTGTTTTAGGAATACATAAAGTATGTCGATATTTATTATAGTCACTAGT

TGTAATTTTTTTGTGGGAAATCCACACTGAGCTGA

FIG. 1B

SEQUENCE RANGE: 1 TO 294

```
              10            20            30            40
         *     *     *     *     *     *     *     *     *
   ATG  AAG  GTC  TCC  GCA  GCA  CTT  CTG  TGG  CTG  CTG  CTC  ATA  GCA  GCT
    M    K    V    S    A    A    L    L    W    L    L    L    I    A.   A>

50            60            70            80            90
         *     *     *     *     *     *     *     *     *
   GCC  TTC  AGC  CCC  CAG  GGG  CTC  GCT  GGG  CCA  GCT  TCT  GTC  CCA  ACC
    A    F    S    P    Q    G    L    A    G    P    A    S    V    P    T>

100           110           120           130
         *     *     *     *     *     *     *     *     *
   ACC  TGC  TGC  TTT  AAC  CTG  GCC  AAT  AGG  AAG  ATA  CCC  CTT  CAG  CGA
    T    C    C    F    N    L    A    N    R    K    I    P    L    Q    R>

140           150           160           170           180
         *     *     *     *     *     *     *     *     *
   CTA  GAG  AGC  TAC  AGG  AGA  ATC  ACC  AGT  GGC  AAA  TGT  CCC  CAG  AAA
    L    E    S    Y    R    R    I    T    S    G    K    C    P    Q    K>

190           200           210           220
         *     *     *     *     *     *     *     *     *
   GCT  GTG  ATC  TTC  AAG  ACC  AAA  CTG  GCC  AAG  GAT  ATC  TGT  GCC  GAC
    A    V    I    F    K    T    K    L    A    K    D    I    C    A    D>

230           240           250           260           270
         *     *     *     *     *     *     *     *     *
   CCC  AAG  AAG  AAG  TGG  GTG  CAG  GAT  TCC  ATG  AAG  TAT  CTG  GAC  CAA
    P    K    K    K    W    V    Q    D    S    M    K    Y    L    D    Q>

280           290
         *     *     *     *
   AAA  TCT  CCA  ACT  CCA  AAG  CCA  TAA
    K    S    P    T    P    K    P    *>
```

FIG. 2

MCP - 1R

CC - CKR3

SEQUENCE RANGE: 1 to 1689

```
                10                  20                  30                  40
         *       *         *        *         *        *         *        *        *
   AAT  CCT  TTT  CCT  GGC  ACC  TCT  GAT  ATC  CTT  TTG  AAA  TTC  ATG  TTA 50                  60                  70                  80                  90
         *       *         *        *         *        *         *        *        *
   AAG  AAT  CCC  TAG  GCT  GCT  ATC  ACA  TGT  GGC  ATC  TTT  GTT  GAG  TAC 100                 110                 120                 130
         *       *         *        *         *        *         *        *        *
   ATG  AAT  AAA  TCA  ACT  GGT  GTG  TTT  TAC  GAA  GGA  TGA  TTA  TGC  TTC 140                 150                 160                 170                 180
         *       *         *        *         *        *         *        *        *
   ATT  GTG  GGA  TTG  TAT  TTT  TCT  TCT  TCT  ATC  ACA  GGG  AGA  AGT  GAA 190                 200                 210                 220
         *       *         *        *         *        *         *        *        *
   ATG  ACA  ACC  TCA  CTA  GAT  ACA  GTT  GAG  ACC  TTT  GGT  ACC  ACA  TCC
   Met  Thr  Thr  Ser  Leu  Asp  Thr  Val  Glu  Thr  Phe  Gly  Thr  Thr  Ser 230                 240                 250                 260                 270
         *       *         *        *         *        *         *        *        *
   TAC  TAT  GAT  GAC  GTG  GGC  CTG  CTC  TGT  GAA  AAA  GCT  GAT  ACC  AGA
   Tyr  Tyr  Asp  Asp  Val  Gly  Leu  Leu  Cys  Glu  Lys  Ala  Asp  Thr  Arg 280                 290                 300                 310
         *       *         *        *         *        *         *        *        *
   GCA  CTG  ATG  GCC  CAG  TTT  GTG  CCC  CCG  CTG  TAC  TCC  CTG  GTG  TTC
   Ala  Leu  Met  Ala  Gln  Phe  Val  Pro  Pro  Leu  Tyr  Ser  Leu  Val  Phe 320                 330                 340                 350                 360
         *       *         *        *         *        *         *        *        *
   ACT  GTG  GGC  CTC  TTG  GGC  AAT  GTG  GTG  GTG  GTG  ATG  ATC  CTC  ATA
   Thr  Val  Gly  Leu  Leu  Gly  Asn  Val  Val  Val  Val  Met  Ile  Leu  Ile 370                 380                 390                 400
         *       *         *        *         *        *         *        *        *
   AAA  TAC  AGG  AGG  CTC  CGA  ATT  ATG  ACC  AAC  ATC  TAC  CTG  CTC  AAC
   Lys  Tyr  Arg  Arg  Leu  Arg  Ile  Met  Thr  Asn  Ile  Tyr  Leu  Leu  Asn 410                 420                 430                 440                 450
         *       *         *        *         *        *         *        *        *
   CTG  GCC  ATT  TCG  GAC  CTG  CTC  TTC  CTC  GTC  ACC  CTT  CCA  TTC  TGG
   Leu  Ala  Ile  Ser  Asp  Leu  Leu  Phe  Leu  Val  Thr  Leu  Pro  Phe  Trp 460                 470                 480                 490
         *       *         *        *         *        *         *        *        *
   ATC  CAC  TAT  GTC  AGG  GGG  CAT  AAC  TGG  GTT  TTT  GGC  CAT  GGC  ATG
   Ile  His  Tyr  Val  Arg  Gly  His  Asn  Trp  Val  Phe  Gly  His  Gly  Met
```

FIG. 15A

```
        500             510             520             530             540
         *       *       *       *       *       *       *       *       *
TGT AAG CTC CTC TCA GGG TTT TAT CAC ACA GGC TTG TAC AGC GAG
Cys Lys Leu Leu Ser Gly Phe Tyr His Thr Gly Leu Tyr Ser Glu 550             560             570             580
         *       *       *       *       *       *       *       *       *
ATC TTT TTC ATA ATC CTG CTG ACA ATC GAC AGG TAC CTG GCC ATT
Ile Phe Phe Ile Ile Leu Leu Thr Ile Asp Arg Tyr Leu Ala Ile 590             600             610             620             630
         *       *       *       *       *       *       *       *       *
GTC CAT GCT GTG TTT GCC CTT CGA GCC CGG ACT GTC ACT TTT GGT
Val His Ala Val Phe Ala Leu Arg Ala Arg Thr Val Thr Phe Gly 640             650             660             670
         *       *       *       *       *       *       *       *       *
GTC ATC ACC AGC ATC GTC ACC TGG GGC CTG GCA GTG CTA GCA GCT
Val Ile Thr Ser Ile Val Thr Trp Gly Leu Ala Val Leu Ala Ala 680             690             700             710             720
         *       *       *       *       *       *       *       *       *
CTT CCT GAA TTT ATC TTC TAT GAG ACT GAA GAG TTG TTT GAA GAG
Leu Pro Glu Phe Ile Phe Tyr Glu Thr Glu Glu Leu Phe Glu Glu 730             740             750             760
         *       *       *       *       *       *       *       *       *
ACT CTT TGC AGT GCT CTT TAC CCA GAG GAT ACA GTA TAT AGC TGG
Thr Leu Cys Ser Ala Leu Tyr Pro Glu Asp Thr Val Tyr Ser Trp 770             780             790             800             810
         *       *       *       *       *       *       *       *       *
AGG CAT TTC CAC ACT CTG AGA ATG ACC ATC TTC TGT CTC GTT CTC
Arg His Phe His Thr Leu Arg Met Thr Ile Phe Cys Leu Val Leu 820             830             840             850
         *       *       *       *       *       *       *       *       *
CCT CTG CTC GTT ATG GCC ATC TGC TAC ACA GGA ATC ATC AAA ACG
Pro Leu Leu Val Met Ala Ile Cys Tyr Thr Gly Ile Ile Lys Thr 860             870             880             890             900
         *       *       *       *       *       *       *       *       *
CTG CTG AGG TGC CCC AGT AAA AAA AAG TAC AAG GCC ATC CGG CTC
Leu Leu Arg Cys Pro Ser Lys Lys Lys Tyr Lys Ala Ile Arg Leu 910             920             930             940
         *       *       *       *       *       *       *       *       *
ATT TTT GTC ATC ATG GCG GTG TTT TTC ATT TTC TGG ACA CCC TAC
Ile Phe Val Ile Met Ala Val Phe Phe Ile Phe Trp Thr Pro Tyr 950             960             970             980             990
         *       *       *       *       *       *       *       *       *
AAT GTG GCT ATC CTT CTC TCT TCC TAT CAA TCC ATC TTA TTT GGA
Asn Val Ala Ile Leu Leu Ser Ser Tyr Gln Ser Ile Leu Phe Gly
```

FIG. 15B

```
              1000           1010           1020           1030
        *      *      *      *      *      *      *      *      *
AAT GAC TGT GAG CGG ACG AAG CAT CTG GAC CTG GTC ATG CTG GTG
Asn Asp Cys Glu Arg Thr Lys His Leu Asp Leu Val Met Leu Val 1040           1050           1060           1070           1080
        *      *      *      *      *      *      *      *      *
ACA GAG GTG ATC GCC TAC TCC CAC TGC TGC ATG AAC CCG GTG ATC
Thr Glu Val Ile Ala Tyr Ser His Cys Cys Met Asn Pro Val Ile 1090           1100           1110           1120
        *      *      *      *      *      *      *      *      *
TAC GCC TTT GTT GGA GAG AGG TTC CGG AAG TAC CTG CGC CAC TTC
Tyr Ala Phe Val Gly Glu Arg Phe Arg Lys Tyr Leu Arg His Phe 1130           1140           1150           1160           1170
        *      *      *      *      *      *      *      *      *
TTC CAC AGG CAC TTG CTC ATG CAC CTG GGC AGA TAC ATC CCA TTC
Phe His Arg His Leu Leu Met His Leu Gly Arg Tyr Ile Pro Phe 1180           1190           1200           1210
        *      *      *      *      *      *      *      *      *
CTT CCT AGT GAG AAG CTG GAA AGA ACC AGC TCT GTC TCT CCA TCC
Leu Pro Ser Glu Lys Leu Glu Arg Thr Ser Ser Val Ser Pro Ser 1220           1230           1240           1250           1260
        *      *      *      *      *      *      *      *      *
ACA GCA GAG CCG GAA CTC TCT ATT GTG TTT TAG GTA GAT GCA GAA
Thr Ala Glu Pro Glu Leu Ser Ile Val Phe ***

1270           1280           1290           1300
        *      *      *      *      *      *      *      *      *
AAT TGC CTA AAG AGG AAG GAC CAA GGA GAT NAA GCA AAC ACA TTA 1310           1320           1330           1340           1350
        *      *      *      *      *      *      *      *      *
AGC CTT CCA CAC TCA CCT CTA AAA CAG TCC TTC AAA CCT TCC AGT 1360           1370           1380           1390
        *      *      *      *      *      *      *      *      *
GCA ACA CTG AAG CTC TTA AGA CAC TGA AAT ATA CAC ACA GCA GTA 1400           1410           1420           1430           1440
        *      *      *      *      *      *      *      *      *
GCA GTA GAT GCA TGT ACC CTA AGG TCA TTA CCA CAG GCC AGG GCT 1450           1460           1470           1480
        *      *      *      *      *      *      *      *      *
GGG CAG CGT ACT CAT CAT CAA CCT AAA AAG CAG AGC TTT GCT TCT 1490           1500           1510           1520           1530
        *      *      *      *      *      *      *      *      *
CTC TCT AAA ATG AGT TAC CTA TAT TTT AAT GCA CCT GAA TGT TAG
```

FIG. 15C

```
          1540           1550           1560           1570
   *       *    *       *     *     *       *     *     *
ATA GTT ACT ATA TGC CGC TAC AAA AAG GTA AAA CTT TTT ATA TTT 1580          1590          1600         1610         1620
   *       *    *       *     *     *       *     *     *
TAT ACA TTA ACT TCA GCC AGC TAT TAT ATA AAT AAA ACA TTT TCA 1630           1640          1650          1660
   *       *    *       *     *     *       *     *     *
CAC AAT ACA ATA AGT TAA CTA TTT TAT TTT CTA ATG TGC CTA GTT 1670          1680
   *       *    *       *
CTT TCC CTG CTT AAT GAA AAG CTT
```

FIG. 15D

HUMAN CHEMOTACTIC CYTOKINE

RELATED APPLICATIONS

This application is a continuation of U.S. application Ser. No. 08/494,093, filed Jun. 23, 1995, the entire teachings of which are incorporated herein by reference.

BACKGROUND OF THE INVENTION

Chemokines, also referred to as intecrines, are soluble, low molecular weight members of the cytokine family which have chemoattractant function. Chemokines are capable of selectively inducing chemotaxis of the formed elements of the blood (other than red blood cells), including leukocytes such as eosinophils, basophils, neutrophils (polymorphonuclear leukocytes), lymphocytes (e.g., T and B cells), and other blood and tissue cells such as mast cells and macrophages. A chemoattractant protein is capable of attracting leukocytes (such as eosinophils or other leukocyte subsets), and of inducing accumulation and/or activation of leukocytes (such as eosinophils or other leukocyte subsets) in vitro and/or in vivo. In addition to stimulating chemotaxis, other changes can be selectively induced by chemokines in responsive cells, including changes in cell shape, transient rises in the concentration of intracellular free calcium ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

The chemokines characterized to date are related in primary structure. They share four conserved cysteines, which form disulphide bonds. cDNA cloning and biochemical characterization of several chemokines has revealed that the proteins typically have a leader sequence of about 20-25 amino acids, which is cleaved upon secretion to yield a mature protein of approximately 92-99 amino acids. Based on the conserved cysteine motif, the family is divided into two branches, designated as the C-C chemokines and the C-X-C chemokines, in which the first two conserved cysteines are adjacent or are separated by an intervening residue, respectively. Baggiolini, M. and C. A. Dahinden, *Immunology Today*, 15: 127-133 (1994)).

The C-X-C chemokines include a number of chemoattractants which are potent chemoattractants and activators of neutrophils, such as interleukin 8 (IL-8), and neutrophil-activating peptide 2 (NAP-2). The C-C chemokines include molecules such as human monocyte chemotactic proteins 1-3 (MCP-1, MCP-2 and MCP-3), RANTES (Regulated on Activation, Normal T-cell Expressed and Secreted), and the macrophage inflammatory proteins 1α and 1β (MIP-1α and MIP-1β), which have been characterized as chemoattractants and activators of monocytes or lymphocytes, but do not appear to be chemoattractants for neutrophils. For example, recombinant RANTES is a chemoattractant for monocytes, as well as for memory T cells in vitro (Schall, T. J. et al., *Nature*, 347: 669-671 (1990)).

The C-C chemokines are of great interest because of their potential role in allergic inflammation. For example, MCP-1 induces exocytosis of human basophils, resulting in release of high levels of inflammatory mediators, such as histamine and leukotriene $C_4$. Similarly, there is great interest in the receptors for the C-C chemokines, which trigger these cellular events in response to chemokine binding. A receptor for C-C chemokines has recently been cloned and is reported to bind MIP-1α and RANTES. Accordingly, this MIP-1α/RANTES receptor was designated C-C chemokine receptor 1 (Neote, K. et al., *Cell*, 72: 415-425 (1993); Horuk, R. et al., WO 94/11504, published May 26, 1994; Gao, J.-I. et al., *J. Exp. Med.*, 177: 1421-1427 (1993)). An MCP-1 receptor has also been cloned (Charo, I. F. et al., *Proc. Natl. Acad. Sci. USA*, 91: 2752 (1994)).

The MCP-1 receptor and the C-C chemokine receptor 1 are predicted to belong to a family of seven transmembrane spanning G-protein coupled receptors. This family of G-protein coupled (serpentine) receptors comprises a large group of integral membrane proteins, containing seven transmembrane-spanning regions. The ligands of these receptors include a diverse group of molecules, including small biogenic amine molecules, such as epinephrine and norepinephrine, peptides, such as substance P and neurokinins, and larger proteins, such as chemokines. The receptors are coupled to G proteins, which are heterotrimeric regulatory proteins capable of binding GTP and mediating signal transduction from coupled receptors, for example, by the production of intracellular mediators.

The cloning and sequencing of two IL-8 receptor cDNAs reveals that these C-X-C receptor proteins also share sequence similarity with seven transmembrane-spanning G protein-coupled receptor proteins (Murphy P. M. and H. L. Tiffany, *Science*, 253: 1280-1283 (1991); Murphy et al., WO 93/06299; Holmes, W. E. et al., *Science*, 253: 1278-1280 (1991)). Additional receptors for chemotactic proteins such as anaphylatoxin C5a and bacterial formylated tripeptide fMLP have been characterized by cloning and been found to encode receptor proteins which also share sequence similarity to these seven transmembrane-spanning proteins (Gerard, N. P. and C. Gerard, *Nature*, 349: 614-617 (1991); Boulay, F. et al., *Biochemistry*, 29: 11123-11133 (1990)). Although a number of other proteins with significant sequence similarity and similar tissue and leukocyte subpopulation distribution to known chemokine receptors have been identified and cloned, the ligands for these receptors remain undefined. Thus, these proteins are referred to as orphan receptors.

The isolation and characterization of additional genes and the encoded chemokine, and the characterization of the corresponding receptor(s), is essential to an understanding of the interaction of chemokines with their target cells and the events stimulated by this interaction, including chemotaxis and cellular activation of leukocytes.

SUMMARY OF THE INVENTION

The present invention relates to isolated and/or recombinant nucleic acids which encode human chemotactic cytokines designated human eotaxins. The invention further relates to recombinant nucleic acid constructs, such as plasmids or retroviral vectors, which contain a nucleic acid which encodes a protein of the present invention or portion thereof. The nucleic acids and constructs can be used to produce recombinant human eotaxin. In another embodiment, the nucleic acid encodes an antisense nucleic acid which can hybridize with a second nucleic acid encoding a human eotaxin of the present invention, and which, when introduced into cells, can inhibit the expression of the polypeptide.

Another aspect of the present invention relates to proteins or polypeptides, referred to herein as isolated and/or recombinant human eotaxin. The recombinant human eotaxin proteins and eotaxin variants of the present invention can be produced in host cells as described herein. In one embodiment, a human eotaxin is characterized by high affinity binding to leukocytes, particularly eosinophils and/or the ability to induce leukocyte accumulation and/or chemotaxis.

Antibodies reactive with the proteins of the present invention can be produced using a human eotaxin, a variant, or portion thereof as immunogen, for example. Such antibodies or fragments thereof are useful in therapeutic, diagnostic and research applications. For example, the antibodies can be used in the purification and study of human eotaxin, the identification of cells which express eotaxin, and the detection of the presence of abnormal levels of eotaxin in a sample.

Also encompassed by the present invention are methods of identifying inhibitors (e.g., antagonists) or promoters (agonists) of human eotaxin function. For example, human eotaxin or variants thereof can be used in assays designed to identify antagonists which block the binding of the chemoattractant protein to its natural receptor(s). In one embodiment, suitable host cells which have been engineered to express a receptor for human eotaxin are used in an assay to identify and/or assess the efficacy of inhibitors or promoters of human eotaxin function.

Agents that inhibit (e.g., prevent, reduce (decrease or abolish)) production, release or activity of a human eotaxin can be used therapeutically in the treatment of inflammatory (e.g., asthma) and autoimmune diseases. In addition, human eotaxin, human eotaxin variants, or agents which act as promoters of human eotaxin function can be administered to an individual providing a method of selective stimulation of leukocyte function, which can be useful, for example, in the treatment of cancer or parasitic infections.

BRIEF DESCRIPTION OF THE DRAWINGS

FIGS. 1A-1B is an illustration of the nucleotide sequence determined from a genomic clone (Clone 25) encoding human eotaxin (SEQ ID NO:1), and the predicted amino acid sequence of the protein encoded by the open-reading frame (SEQ ID NO:2). The gene contains two introns. (Standard single letter amino acid codes are used.)

FIG. 2 is an illustration of the nucleotide sequence determined for a cDNA clone encoding human eotaxin (SEQ ID NO:3), and the predicted amino acid sequence of the protein encoded by the open-reading frame (SEQ ID NO:4).

FIG. 3 also shows the results of an assay in which migration of PBMC in response to MCP-1 was determined using a fluorescence activated cell sorter. Cell size and side scatter of human PBMC (left); background migration in a "no chemokine" control (center); and migration of cells (particularly the monocyte population) in response to 100 ng/ml of MCP-1 (right) are plotted.

FIG. 4B, monocytes; FIG. 4C, activated T cells; FIG. 4D, eosinophils) in response to 100 ng/ml of chemokine present in the bottom chamber of a chemotaxis assay (MCP-1, MCP-2, MCP-3, MIP-1α (MIP-1a), RANTES, interleukin-8 (IL-8), IP-10, MIP-1β, or human eotaxin). Chemotaxis plates were incubated at 37° C. for 90 minutes, and the cells which migrated to the bottom chamber were counted by microscopy (HPF=high power field). This was a representative experiment of at least four experiments performed.

FIGS. 15A-15D is an illustration of the nucleotide sequence determined from a genomic clone encoding a human C-C chemokine receptor 3 (CKR-3) protein (also referred to as Eos L2 receptor) (SEQ ID NO:5), and the predicted amino acid sequence of the protein encoded by the open-reading frame (SEQ ID NO:6).

DETAILED DESCRIPTION OF THE INVENTION

Proteins and Peptides

Figure 3:
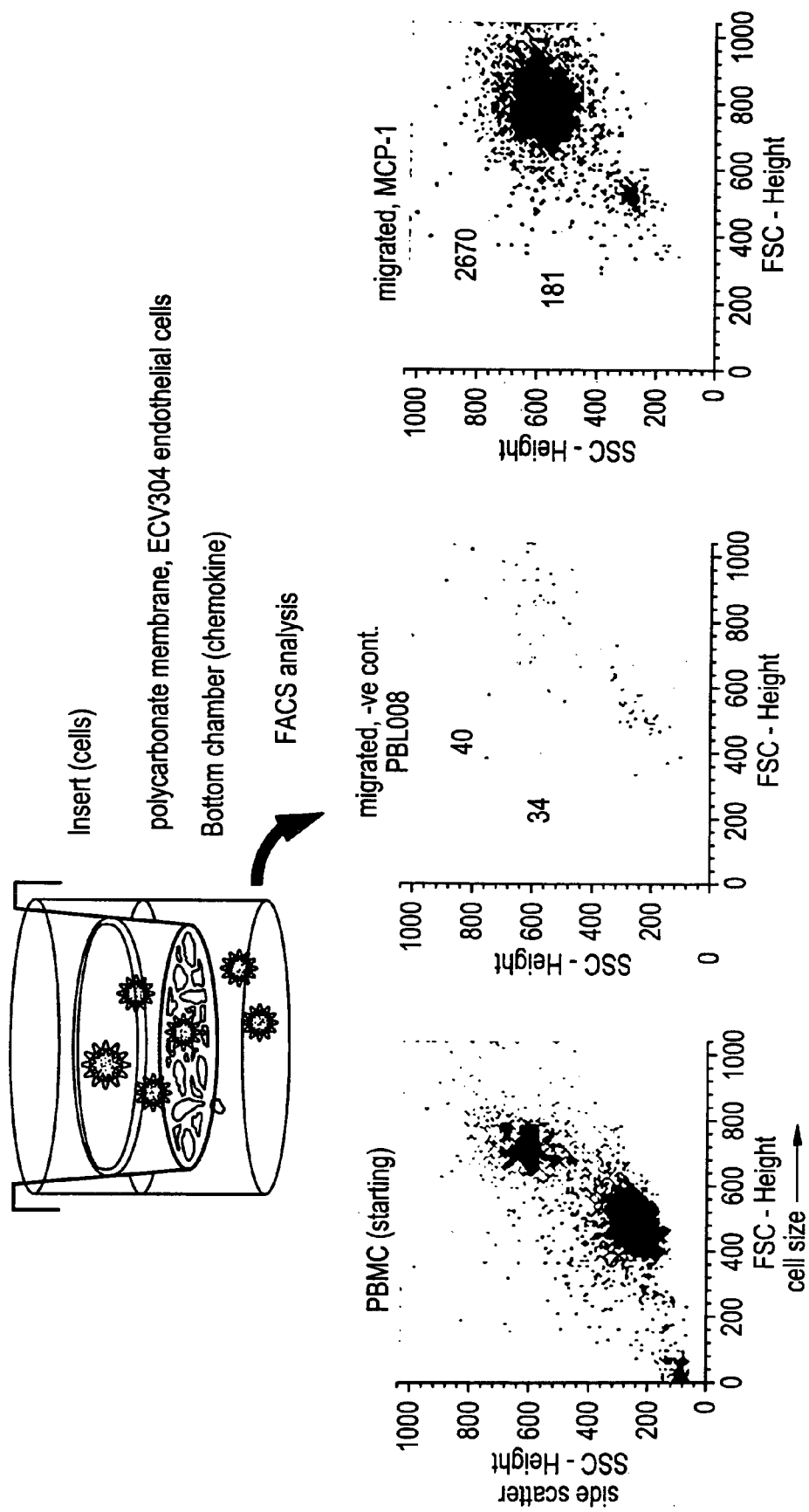
FIG. 3 is an illustration of one type of transendothelial chemotaxis assay. A culture insert is placed into a container, such as a well in a 24-well plate, creating a first (upper) and second (lower) chamber within the well. ECV304 endothelial cells are grown in a monolayer on the polycarbonate membrane on the inner side of the insert. Cells (e.g., leukocytes, such as eosinophils) to be assessed for a response to a substance (e.g., a chemokine) are introduced into the top chamber and the substance is introduced into the bottom chamber. The insert can be removed, and cells which have migrated from the top chamber through the endothelial layer into the bottom chamber can be detected or counted by a suitable method to assess chemotaxis. For example, cells in the bottom chamber can be collected and counted by microscopy or flow cytometry (e.g., FACS analysis).

The present invention relates to isolated and/or recombinant (including, e.g., essentially pure) proteins or polypeptides which are human chemotactic cytokines (chemokines) and are designated human eotaxin. Proteins or polypeptides referred to herein as "isolated" are proteins or polypeptides purified to a state beyond that in which they exist in mammalian cells. "Isolated" proteins or polypeptides include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Proteins or polypeptides referred to herein as "recombinant" are proteins or polypeptides produced by the expression of recombinant nucleic acids of the present invention.

As used herein human eotaxin refers to naturally occurring or endogenous human eotaxin protein (a human eotaxin protein recovered from a source which naturally produces human eotaxin, including polymorphic or allelic variants), including mature eotaxin, and proteins having the same amino acid sequence as naturally occurring or endogenous human eotaxin protein. Isolated and/or recombinant human eotaxin is a ligand for one or more natural or physiological receptor(s) for eotaxin and/or can stimulate eosinophil accumulation and/or attract eosinophils (induce chemotaxis). In one embodiment, isolated (e.g., chemically synthesized) and/or recombinant human eotaxin has the same amino acid sequence as a naturally occurring human eotaxin protein. For example, as shown herein, an isolated protein corresponding to amino acids 24-97 of FIG. 2 (predicted mature eotaxin) can bind to a receptor present on human eosinophils specifically and with high affinity and can induce chemotaxis of eosinophils from humans or other primates. In addition, this isolated human protein can also bind to transfected cells expressing human C-C chemokine receptor 3 (CKR-3) and induce chemotaxis of the cells.

As shown herein, the proteins encompassed by the term human eotaxin are eosinophil-specific chemoattractants capable of stimulating eosinophil accumulation and/or attracting eosinophils (inducing chemotaxis). Eosinophil-specific activity can be assessed in vitro, where the proteins are capable of attracting or inducing chemotaxis of eosinophils, but do not significantly induce chemotaxis of neutrophils, monocytes or T cells. Eosinophil-specific activity can also be assessed in vivo, where the proteins are capable of specifically inducing accumulation and/or chemotaxis of eosinophils. For example, upon intradermal injection the polypeptides elicit a predominantly eosinophilic infiltration.

The invention also relates to isolated and/or recombinant portions or fragments of a human eotaxin. In one embodiment, an isolated and/or recombinant portion (e.g., a peptide) of human eotaxin has at least one function characteristic of a human eotaxin, such as a binding function (e.g., binding to an eotaxin receptor or other receptor); a leukocyte activation function (e.g., activation of a G protein, induction of rapid and transient increase in the concentration of cytosolic free calcium $[Ca^{2+}]_i$, induction of exocytosis or inflammatory mediator release, leukocyte integrin activation); and/or a leukocyte stimulation function (e.g., induces accumulation and/or chemotaxis of leukocytes, especially of eosinophils such as human or primate eosinophils (has eosinophil-specific chemoattractant activity)). For example, one type of isolated and/or recombinant human eotaxin fragment can bind a receptor for eotaxin, but cannot induce leukocyte activation and/or stimulation. In one embodiment, an isolated and/or recombinant human eotaxin portion is an eosinophil-specific chemoattractant capable of stimulating eosinophil accumulation and/or chemotaxis. Examples of functional fragments or portions of a human eotaxin include those with deletions of one or more amino acids from the mature protein which retain one or more of the above functions. The amino acids which can be deleted can be identified by screening. For example the N- or C-terminus of the protein can be deleted in a step-wise fashion and the resulting protein or polypeptide screened in one or more assays as described herein. Also envisioned are fragments wherein an (i.e., one or more) internal amino acid is deleted, including deletions of non-contiguous amino acids. Where the resulting protein displays activity in the assay, the resulting protein ("fragment") is functional.

In an alternative embodiment, an isolated and/or recombinant portion (e.g., a peptide) of human eotaxin has at least one immunological property of a human eotaxin. For example, as described in more detail below, some portions of a human eotaxin can be produced (e.g., synthetic peptides) and used to produce antibodies. These portions are immunogenic and induce an antibody response against themselves when used in a suitable immunization protocol (e.g., conjugated to a suitable carrier). However, portions are not required to be immunogenic. As used herein, a portion (polypeptide or peptide) of human eotaxin having "at least one immunological property" of human eotaxin is a polypeptide or peptide which (a) is bound by at least one antibody of a selected epitopic specificity which binds a naturally occurring human eotaxin; and/or (b) is an immunogen capable of inducing the formation in a suitable animal of at least one antibody of a selected epitopic specificity which binds a naturally occurring human eotaxin. For example, a portion can be cross-reactive with an antibody which is raised against and/or reactive with human eotaxin. In a preferred embodiment, the antibody of selected epitopic specificity is specific for human eotaxin, and in a particularly preferred embodiment binds to human eotaxin with high affinity (e.g., a Ka in the range of about 1-10 nM).

In yet another embodiment, an isolated and/or recombinant portion of human eotaxin has at least one function characteristic of human eotaxin and at least one immunological property of a human eotaxin.

Studies on the structure and function of C-C chemokines provide the basis for being able to divide C-C chemokines into functional domains (e.g., leader peptide, mature protein; Miller, M. D. and M. S. Krangel, *Critical Rev. Immunol.*, 12 (1,2): 17-46 (1992); see also, Gong, J. H. and I. L. Clark-Lewis, *J. Exp. Med.*, 181: 631-6410 (1995)). Portions of human eotaxin can be produced which have full or partial function on their own, or which when joined with another portion of a second chemokine (though fully, partially, or nonfunctional alone), constitute a functional protein having at least one function characteristic of a mammalian C-C chemokine, such as human eotaxin (e.g., binding, leukocyte activation and/or stimulation function).

The invention further relates to mutants, variants or derivatives of a human eotaxin (e.g., a mature human eotaxin). Such variants include natural or artificial variants of a naturally occurring human eotaxin, differing by the addition, deletion or substitution of one or more amino acid residues, or modified polypeptides in which one or more residues is modified, and mutants comprising one or more modified residues.

The invention further relates to fusion proteins, comprising a human eotaxin (e.g., mature human eotaxin, or the full-length product (amino acids 1-97 of FIG. 2)) as a first moiety, linked to a second moiety not occurring in the human eotaxin as found in nature. Thus, the second moiety can be an amino acid or polypeptide. The first moiety can be in an N-terminal location, C-terminal location or internal to the fusion protein. In one embodiment, the fusion protein comprises a human eotaxin or portion thereof as the first moiety, and a second moiety comprising a linker sequence and affinity ligand (e.g., an enzyme, an antigen, epitope tag).

Fusion proteins can be produced by a variety of methods. For example, some embodiments can be produced by the insertion of a human eotaxin gene or portion thereof into a suitable expression vector, such as Bluescript®II SK +/− (Stratagene), pGEX-4T-2 (Pharmacia) and pET-15b (Novagen). The resulting construct is then introduced into a suitable host cell for expression. Upon expression, fusion protein can be isolated or purified from a cell lysate by means of a suitable affinity matrix (see e.g., *Current Protocols in Molecular Biology* (Ausubel, F. M. et al., eds., Vol. 2, Suppl. 26, pp. 16.4.1-16.7.8 (1991)). In addition, affinity labels provide a means of detecting a fusion protein comprising a human eotaxin moiety. For example, the cell surface expression or presence in a particular cell fraction of a fusion protein comprising an antigen or epitope affinity label can be detected by means of an appropriate antibody.

Nucleic Acids, Constructs and Vectors

The present invention further relates to isolated and/or recombinant (including, e.g., essentially pure) nucleic acids having sequences which encode a protein of the present invention, including human eotaxin or a portion thereof. In one embodiment, the nucleic acid or portion thereof encodes a protein having at least one function characteristic of human eotaxin, such as a binding function (e.g., binding to an eotaxin receptor or other receptor); a leukocyte activation function (e.g., activation of a G protein, induction of rapid and transient increase in the concentration of cytosolic free calcium $[Ca^{2+}]_i$ induction of exocytosis or inflammatory mediator release, leukocyte integrin upregulation and/or activation); and/or a leukocyte stimulation function (e.g., induces accumulation and/or chemotaxis of leukocytes, especially of eosinophils such as human or primate eosinophils (has eosinophil-specific chemoattractant activity)). The present invention also relates more specifically to isolated and/or recombinant nucleic acids comprising sequences which encode a human eotaxin or a portion thereof.

The invention further relates to isolated and/or recombinant nucleic acids that are characterized by (1) their ability to hybridize to: (a) a nucleic acid having the sequence shown in FIGS. 1A-1B (SEQ ID NO:1) or FIG. 2 (SEQ ID NO:3), (b) the complement of the sequence shown in FIGS. 1A-1B (SEQ ID NO:1) or FIG. 2 (SEQ ID NO:3), (c) the RNA counterpart of either of the foregoing, wherein U is substituted for T, or (d) a portion of any of the foregoing (e.g., a portion comprising the open reading frame); or (2) by their ability to encode a polypeptide having the amino acid sequence shown in FIGS. 1A-1B (SEQ ID NO:2) or FIG. 2 (SEQ ID NO:4) or a functional equivalent thereof (i.e., a polypeptide which binds one or more natural receptors of human eotaxin and/or induces accumulation and/or chemotaxis of leukocytes, especially of eosinophils such as human or primate eosinophils); or (3) by both characteristics.

C-C chemokine genes typically encode a polypeptide having an amino-terminal signal sequence or presequence for secretion, which is cleaved to yield a mature protein active in binding, and in inducing accumulation and/or chemotaxis. Alignment of the amino acid sequence of the protein encoded by the genomic and cDNA clones described herein with other C-C chemokines indicates that the encoded protein also has a leader sequence for secretion. Based on the alignment with other C-C chemokines, the leader sequence corresponds to amino acids 1-23 of the predicted protein, yielding a predicted mature protein beginning with $Gly^{24}$ (amino acids 24-97 of FIGS. 1A-1B (SEQ ID NO:2) or FIG. 2 (SEQ ID NO:4)). Functional equivalents of a polypeptide having the amino acid sequence shown in FIGS. 1A-1B (SEQ ID NO:2) or FIG. 2 (SEQ ID NO:4) include proteins corresponding to mature eotaxin. In one embodiment, functional equivalents of the amino acid sequence shown in FIGS. 1A-1B (SEQ ID NO:2) or FIG. 2 (SEQ ID NO:4) are defined by their sequence similarity to a protein having an amino acid sequence corresponding to amino acids 24-97 of FIGS. 1A-1B (amino acids 24-97 of SEQ ID NO:2) or FIG. 2 (SEQ ID NO:4), and the functional equivalents have at least about 75% ($\leq 75\%$) sequence similarity with said protein. In a preferred embodiment, the functional equivalents share at least about 80% sequence similarity with said protein. More preferably, the percent amino acid sequence similarity is at least about 90%, and still more preferably, at least about 95%.

Isolated and/or recombinant nucleic acids meeting these criteria comprise nucleic acids having sequences identical to sequences of naturally occurring human eotaxin genes (including polymorphic or allelic variants) and portions thereof, or variants of the naturally occurring sequences. Such variants include mutants differing by the addition, deletion or substitution of one or more residues, modified nucleic acids in which one or more residues is modified (e.g., DNA or RNA analogs), and mutants comprising one or more modified residues.

Such nucleic acids can be detected and isolated by hybridization under high stringency conditions or moderate stringency conditions, for example. "High stringency conditions" and "moderate stringency conditions" for nucleic acid hybridizations are explained on pages 2.10.1-2.10.16 (see particularly 2.10.8-11) and pages 6.3.1-6 in *Current Protocols in Molecular Biology* (Ausubel, F. M. et al., eds., Vol.

1, Suppl. 26, 1991), the teachings of which are incorporated herein by reference (see also Example 2). Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other nucleic acids are being compared for homology.

Isolated and/or recombinant nucleic acids that are characterized by their ability to hybridize to a nucleic acid having the sequence shown in FIGS. 1A-1B (SEQ ID NO:1) or FIG. 2 (SEQ ID NO:3), the complement or RNA counterpart of the sequence shown in FIGS. 1A-1B (SEQ ID NO:1) or FIG. 2 (SEQ ID NO:3), or a portion thereof (e.g., under high conditions) can further encode a human eotaxin or portion thereof. Such portions have at least one function characteristic of human eotaxin, such as a binding function (e.g., binding to an eotaxin receptor or other receptor); a leukocyte activation function (e.g., activation of a G protein, induction of rapid and transient increase in the concentration of cytosolic free calcium $[Ca^{2+}]_i$, induction of exocytosis or inflammatory mediator release, leukocyte integrin activation); and/or a leukocyte stimulation function (e.g., induces accumulation and/or chemotaxis of leukocytes, especially of eosinophils), and/or at least one immunological property of a human eotaxin.

The binding function of a polypeptide encoded by hybridizing nucleic acid can be detected in binding or binding inhibition assays using membrane fractions containing a suitable receptor or cells expressing receptor, for instance (see Examples 6 and 7; see also, Van Riper et al., *J. Exp. Med.*, 177: 851-856 (1993); Sledziewski et al., U.S. Pat. No. 5,284,746 (Feb. 8, 1994)). Thus, the ability of the encoded protein or polypeptide to bind a receptor present on eosinophils or cells transfected with a suitable receptor, such as C-C CKR-3, can be assessed.

The leukocyte activation function of a protein or polypeptide encoded by hybridizing nucleic acid can be detected by enzymatic assays for G protein activity responsive to polypeptide binding to a receptor (e.g., exchange of GTP for GDP on the G protein a subunit, using membrane fractions). G protein coupling can be further assessed, for example, using assays in which stimulation by G protein is blocked by treatment or pre-treatment of cells or a suitable cellular fraction (e.g., membranes) with specific inhibitors of G proteins, such as Bordetella pertussis toxin (Bischoff, S. C. et al., *Eur. J. Immunol.* 23: 761-767 (1993); Sozzani, S. et al., *J. Immunol.* 147: 2215-2221 (1991)).

Standard assays which monitor the induction of a rapid and transient increase in the concentration of cytosolic free calcium $[Ca^{2+}]_i$ (Example 5), exocytosis (e.g., of enzymes such as eosinophil peroxidase, β-glucuronidase) or inflammatory mediator (e.g., histamine, leukotriene) release can be used to assess the response of leukocytes to a human eotaxin, variant or portion thereof (see e.g., Bischoff, S. C. et al., *Eur. J. Immunol.*, 23: 761-767 (1993); Rot, A. et al., *J. Exp. Med.*, 176: 1489-1495 (1992); Baggliolini, M. and C. A. Dahinden, *Immunology Today*, 15:127-133 (1994) and references cited therein).

The stimulatory function of a protein or polypeptide encoded by hybridizing nucleic acid can be detected by standard assays for chemotaxis. For example, chemotaxis of eosinophils in response to a polypeptide can be assessed (see e.g., Example 4). In another embodiment, the chemotaxis of cells expressing an eotaxin receptor in response to a polypeptide is monitored (see e.g., Example 7).

Functions characteristic of a human eotaxin may also be assessed by other suitable methods (see below). These methods, alone or in combination with other suitable methods can also be used in procedures for the identification and/or isolation of nucleic acids which encode a polypeptide having the amino acid sequence shown in FIGS. 1A-1B (SEQ ID NO:2) or FIG. 2 (SEQ ID NO:4) or functional equivalents thereof, and having an activity detected by the assay. Portions of isolated and/or recombinant nucleic acids which encode polypeptide portions of the protein shown in FIGS. 1A-1B (SEQ ID NO:2) or FIG. 2 (SEQ ID NO:4) having a certain function can be also identified and isolated in this manner.

Nucleic acids of the present invention can be used in the production of proteins or polypeptides. For example, a nucleic acid containing all or part of the coding sequence for a human eotaxin or a variant thereof, or DNA which hybridizes to the nucleic acid sequence shown in FIGS. 1A-1B (SEQ ID NO:1) or FIG. 2 (SEQ ID NO:3)(or to the complement or RNA counterpart of these sequences), can be incorporated into various constructs and vectors created for further manipulation of sequences or for production of the encoded polypeptide in suitable host cells.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated (see e.g., Daugherty, B. L. et al., *Nucleic Acids Res.*, 19(9):2471-2476 (1991); Lewis, A. P. and J. S. Crowe, *Gene*, 101: 297-302 (1991)). Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Antisense Constructs

In another embodiment, the nucleic acid is an antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell using methods known in the art or other suitable methods, antisense nucleic acid can inhibit the expression of the gene encoded by the sense strand. Antisense nucleic acids can be produced by standard techniques.

In one embodiment, the antisense nucleic acid is wholly or partially complementary to and can hybridize with a target nucleic acid, wherein the target nucleic acid can hybridize to a nucleic acid having the sequence of the complement of the nucleic acid shown in FIGS. 1A-1B (SEQ ID NO:1) or FIG. 2 (SEQ ID NO:3). For example, antisense nucleic acid can be complementary to a target nucleic acid having the sequence of FIGS. 1A-1B (SEQ ID NO:1) or a portion thereof sufficient to allow hybridization. In another embodiment, the antisense nucleic acid is wholly or partially complementary to and can hybridize with a target nucleic acid which encodes, for example, human eotaxin.

Antisense nucleic acids are useful for a variety of purposes, including research and therapeutic applications. For example, a construct comprising an antisense nucleic acid can be introduced into a suitable cell to inhibit eotaxin expression. In one embodiment, such a construct is introduced into some or all of the cells of a mammal. The antisense nucleic acid inhibits eotaxin expression, and inflammatory processes mediated by eotaxin can be inhibited. Thus, an inflammatory disease or condition can be treated using an antisense nucleic acid of the present invention. Suitable laboratory animals comprising an antisense construct can also provide useful models for deficiencies of leukocyte function, and of eosinophil deficiency in particular, and provide further information regarding eotaxin function. Such animals can provide valuable models of infectious disease, useful for elucidating the role of leukocytes, such as eosinophils, in host defenses.

Novel Chemokine Genes

Because advances in the understanding and treatment of human inflammatory and autoimmune diseases and of parasitic infections would be of tremendous benefit, human eotaxin was the species selected for the experimental work described herein. However, the approaches described to isolate and manipulate genomic DNA and cDNA encoding a human eotaxin, to construct vectors and host strains, and to produce and use eotaxin or portions thereof, can be applied to other primates (e.g., a primate other than a human, such as a monkey (e.g., cynomolgus monkey)). The human cDNA or genomic clones described herein, or sufficient portions thereof, whether isolated and/or recombinant or synthetic, including fragments produced by PCR, can be used as probes or primers to detect and/or recover allelic variants of the genes described herein, eotaxin homologs or other related chemokine genes (e.g., novel C-C chemokine genes) from other mammalian species (e.g., by hybridization, PCR or other suitable techniques). This can be achieved using the procedures described herein or other suitable methods.

Method of Producing Recombinant Proteins

Another aspect of the invention relates to a method of producing human eotaxin or a portion thereof, and variants of human eotaxin. Example 3 describes the chemical synthesis of a predicted mature human eotaxin consisting of amino acids 24-97 of FIG. 2 (amino acids 24-97 of SEQ ID NO:4). In addition, constructs suitable for the expression of a human eotaxin or a portion thereof are provided. The constructs can be introduced into a suitable host cell. Cells expressing a recombinant human eotaxin, portion thereof, or variants of human eotaxin, can be produced and maintained in culture. Such cells are useful for a variety of purposes such as the production of protein for characterization, isolation and/or purification. Suitable host cells can be procaryotic, including bacterial cells such as *E. coli, B. subtilis* and/or other suitable bacteria, or eucaryotic, such as fungal or yeast cells (e.g., *Pichia pastoris, Aspergillus* species, *Saccharomyces cerevisiae, Schizosaccharomyces pombe, Neurospora crassa*), or other lower eucaryotic cells, and cells of higher eucaryotes such as those from insects (e.g., Sf9 insect cells) or mammals (e.g., 293 cells, Chinese hamster ovary cells (CHO)). (See, e.g., Ausubel, F. M. et al., eds. *Current Protocols in Molecular Biology*, Greene Publishing Associates and John Wiley & Sons Inc., (1993)). In one embodiment, host cells capable of secreting a mature protein are used.

Host cells which produce a recombinant human eotaxin, portion thereof, variant, or fusion protein can be produced as follows. For example, a nucleic acid encoding all or part of the coding sequence for a human eotaxin or fusion protein can be inserted into a nucleic acid vector, e.g., a DNA vector, such as a plasmid, virus or other suitable replicon for expression. A variety of vectors are available, including vectors which are maintained in single copy or multiple copy, or which become integrated into the host cell chromosome.

The transcriptional and/or translational signals of a human eotaxin gene can be used to direct expression. Alternatively, suitable expression vectors are available. Suitable vectors for expression of a nucleic acid encoding all or part of the coding sequence, for e.g., a human eotaxin, portion thereof, or variant of human eotaxin can contain a number of additional components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence of human origin or from a heterologous species (for secretion provided by the vector, eotaxin coding sequence, or other source).

A promoter is provided for expression in a suitable host cell. Promoters can be constitutive or inducible. In the vectors, the promoter is operably linked to a nucleic acid encoding the human eotaxin, portion thereof or variant, and is capable of directing expression of the encoded polypeptide. A variety of suitable promoters for procaryotic (e.g., lac, tac, T3, T7 promoters for *E. coli*) and eucaryotic (e.g., yeast alcohol dehydrogenase (ADH1), SV40, CMV) hosts are available.

In addition, the expression vectors typically comprise a selectable marker for selection of host cells carrying the vector, in the case of replicable expression vectors, an origin or replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The present invention also relates to cells carrying these expression vectors.

When the nucleic acid encoding the human eotaxin, portion thereof, or variant is inserted into the vector, operably linked to one or more of these expression control elements, and the resulting construct is introduced into host cells maintained under conditions suitable for expression, the encoded polypeptide is produced. The construct can be introduced into cells by a method appropriate to the host cell selected (e.g., transformation, transfection, electroporation, infection). For production of a human eotaxin, host cells comprising the construct are maintained under conditions appropriate for expression, (e.g., in the presence of inducer, suitable media supplemented with appropriate salts, growth factors, antibiotic, nutritional supplements, etc.). The encoded protein (e.g., human eotaxin) can be isolated from the host cells or medium.

Antibodies

The invention further relates to antibodies reactive with a human eotaxin or portion thereof. In one embodiment, antibodies are raised against an isolated and/or recombinant protein of the present invention, including human eotaxin or a portion thereof (e.g., a peptide). In a preferred embodiment, the antibodies specifically bind a human eotaxin or a portion thereof.

The antibodies of the present invention can be polyclonal or monoclonal (see e.g., Example 8), and the term antibody is intended to encompass both polyclonal and monoclonal antibodies. Antibodies of the present invention can be raised against an appropriate immunogen, including proteins or polypeptides of the present invention, such as an isolated (e.g., synthetic) and/or recombinant human eotaxin or a portion thereof (e.g., synthetic peptides). Synthetic peptides can be conjugated to a suitable carrier for immunization.

Preparation of immunizing antigen, and polyclonal and monoclonal antibody production can be performed using any suitable technique. A variety of methods have been described (see e.g., Kohler et al., *Nature*, 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) are isolated using selective culture conditions, and cloned by limiting dilution. Cells which produce antibodies with the desired specificity are selected by a suitable assay (e.g., ELISA).

Single chain antibodies, and chimeric, humanized or primatized (CDR-grafted) antibodies, as well as chimeric or CDR-grafted single chain antibodies, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Pat. No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology*, 10: 1455-1460 (1992), regarding primatized antibody, and Ladner et al., U.S. Pat. No. 4,946,778 and Bird, R. E. et al., *Science*, 242: 423-426 (1988)) regarding single chain antibodies.

In addition, functional fragments of antibodies, including fragments of chimeric, humanized, primatized or single chain antibodies, can also be produced. Functional fragments of foregoing antibodies retain at least one binding function and/or modulation function of the full-length antibody from which they are derived. For example, antibody fragments capable of binding to a human eotaxin or portion thereof, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Alternatively, antibodies can be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

The antibodies of the present invention are useful in a variety of applications, including processes, research, diagnostic and therapeutic applications. For instance, they can be used to isolate and/or purify human eotaxin, portions thereof, or variants of human eotaxin, and to study human eotaxin structure (e.g., conformation) and function.

The antibodies of the present invention can also be used to modulate chemokine function in in vitro and therapeutic applications. For instance, antibodies can act as inhibitors to inhibit (reduce or prevent) (a) binding of a human eotaxin, inhibitor or promoter of eotaxin function, for example, to its receptor(s), (b) leukocyte activation, (c) and/or leukocyte stimulation (e.g., accumulation and/or chemotaxis of leukocytes such as eosinophils). Antibodies which act as inhibitors of human eotaxin function can block human eotaxin binding directly or indirectly (e.g., by causing a conformational change or by desensitization (with or without inhibition of binding of a ligand)).

In addition, the various antibodies of the present invention can be used to detect or measure the expression of eotaxin, for example, in cells transfected with a nucleic acid of the present invention or in a sample from a patient (e.g., inflammatory exudate). Thus, they also have utility in diagnostic or in vitro applications.

Anti-idiotypic antibodies are also provided. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See e.g., U.S. Pat. No. 4,699,880.

In one embodiment, antibodies are raised against a human eotaxin or a portion thereof, and these antibodies are used in turn to produce an anti-idiotypic antibody.

This anti-Id antibody can bind molecules which bind eotaxin, such as a receptor(s) for eotaxin, and can be used in an immunoassay to detect, isolate and/or quantitate molecules which bind eotaxin. In one embodiment, such an anti-idiotypic antibody can be an inhibitor of eotaxin function, although it does not bind eotaxin itself. In another embodiment, such an anti-idiotypic antibody can be an agonist of eotaxin function, by binding to one or more natural receptors of human eotaxin and/or inducing leukocyte activation (e.g., activation of a G protein, induction of rapid and transient increase in the concentration of cytosolic free calcium [Ca$^{2+}$]$_i$, induction of exocytosis or inflammatory mediator release, leukocyte integrin activation) and/or leukocyte stimulation (e.g., induce accumulation and/or chemotaxis of leukocytes, especially of eosinophils).

Anti-idiotypic (i.e., Anti-Id) antibody can itself be used to raise an anti-idiotypic antibody (i.e., Anti-anti-Id). Such an antibody can be similar or identical in specificity to the original immunizing antibody. In one embodiment, antibody antagonists which block binding to receptor can be used to raise Anti-Id, and the Anti-Id can be used to raise Anti-anti-Id, which can have a specificity which is similar or identical to that of the antibody antagonist. These anti-anti-Id antibodies can be assessed for inhibitory effect on eotaxin function to determine if they are antagonists.

Single chain, and chimeric, humanized or primatized (CDR-grafted), as well as chimeric or CDR-grafted single chain anti-idiotypic antibodies can be prepared, and are encompassed by the term anti-idiotypic antibody. Antibody fragments of such antibodies can also be prepared. Identification of Inhibitors or Promoters of Human Eotaxin Function and Identification of Receptors for Eotaxin As used herein, a ligand is a substance which binds to a receptor protein. For example, human eotaxin binds to an eotaxin receptor. In one embodiment, eotaxin can bind selectively to two or more receptors. In a preferred embodiment, eotaxin binding of a receptor occurs with high affinity. The term ligand refers to substances including, but not limited to, a natural ligand, whether isolated and/or purified, synthetic, and/or recombinant, a homolog of a natural ligand (e.g., from another mammal), antibodies, portions of such molecules, and other substances which bind receptor. A natural ligand of a selected receptor can bind to the receptor under physiological conditions, and is of an origin (species) which is the same as that of the receptor. The term ligand encompasses substances which are inhibitors or promoters of receptor activity, as well as substances which bind but lack inhibitor or promoter activity.

As used herein, an inhibitor is a substance which inhibits at least one function characteristic of a human eotaxin, such as a binding function (e.g., binding to an eotaxin receptor or other receptor); a leukocyte activation function (e.g., activation of a G protein, induction of rapid and transient increase in the concentration of cytosolic free calcium $[Ca^{2+}]_i$, induction of exocytosis or inflammatory mediator release, leukocyte integrin upregulation and/or activation); and/or a leukocyte stimulation function (e.g., induces accumulation and/or chemotaxis of leukocytes, especially of eosinophils such as human or primate eosinophils). The term inhibitor refers to substances including antagonists, which can bind an eotaxin receptor and inhibit eotaxin function (e.g., binding function, leukocyte activation and/or stimulation function is inhibited) directly or indirectly, such as a competitive inhibitor of eotaxin binding to its receptor(s) (e.g., a fragment of naturally occurring human eotaxin or a variant of a human eotaxin) or an anti-idiotypic antibody which binds a receptor(s) for eotaxin. In one embodiment, the inhibitor is a substance other than naturally occurring human eotaxin or a polypeptide having the same amino acid sequence as naturally occurring human eotaxin, or other naturally occurring ligands of a human eotaxin receptor (e.g., RANTES is another ligand for CKR-3 receptor protein). The term inhibitor also encompasses agents which inhibit (prevent or reduce (e.g., decrease or abolish)) production, release or activity of human eotaxin, such as an anti-eotaxin antibody which inhibits eotaxin function, or other agent.

As used herein, a promoter is a substance which promotes (induces or enhances) at least one function characteristic of a human eotaxin, such as a binding function, leukocyte (e.g., eosinophil) activation function and/or leukocyte (e.g., eosinophil) stimulation function. The term promoter refers to substances including agonists such as an anti-idiotypic antibody as described herein, variants of human eotaxin, a homolog of eotaxin isolated from another species, and substances which promote or enhance eotaxin function.

Because of the role of chemokines in the selective induction of leukocyte chemotaxis and leukocyte activation in response to chemoattractants, chemokines play a fundamental role in leukocyte migration, and particularly in migration associated with inflammation. Chemokines, produced at sites of inflammation and infection (e.g., wounds), specifically recruit selected leukocyte subtypes from the circulation to the site of inflammation in the tissues. Subsequent to chemokine binding to a leukocyte chemokine receptor, integrin activation occurs, and leukocytes adhere firmly to the endothelial cell wall via leukocyte integrins and endothelial cell adhesion molecules. The leukocytes become flat in shape, and migrate through the endothelium towards sites of inflammation in the tissues. The specificity of a leukocyte for a tissue or inflammatory site is, in many cases, determined at the level of the chemokine-receptor interaction, rather than at the level of the adhesion interaction between integrin and cellular adhesion molecules.

Modulation of eotaxin function according to the present invention, through the inhibition or promotion of human eotaxin function (e.g., binding, activation and/or stimulation), provides an effective and selective way of inhibiting or promoting leukocyte-mediated inflammatory action, particularly that of eosinophils. Inhibitors and promoters of eotaxin function, such as those identified as described herein, can be used to modulate leukocyte function for therapeutic and/or prophylactic purposes in humans. As a major eosinophil chemokine, human eotaxin is an important target for interfering with or promoting leukocyte, especially eosinophil function. Agents which inhibit or promote human eotaxin function (e.g., binding to a receptor(s)), such as other ligands of an eotaxin receptor, inhibitors and promoters identified according to the present method, are particularly useful for modulating eosinophil function for therapeutic and/or prophylactic purposes. It will be appreciated that inhibitors or promoters of human eotaxin, can also be inhibitors or promoters of primate eotaxins or other mammalian eotaxin homologs.

The assays described below, which rely upon the nucleic acids and proteins of the present invention, can be used, alone or in combination with each other or other suitable methods, to identify inhibitors or promoters of eotaxin function. The in vitro method of the present invention can be used in high-throughput screening. These assays can be adapted for processing large numbers of samples (e.g., a 96 well format).

In another aspect, they can be used to identify receptors for eotaxin, which are also useful in identifying inhibitors or promoters of human eotaxin. For example, the present invention also relates to the identification of a receptor-ligand pair: human eotaxin and human C-C chemokine receptor 3 (CKR-3). As shown herein, human eosinophils have a single class of high affinity binding sites for eotaxin. As described in copending U.S. Ser. No. 08/375,199, entitled "Novel G Protein-Coupled Receptor Gene and Methods of Use Therefor", filed Jan. 19, 1995, human eosinophils express CKR-3 receptors. As further shown herein, synthetic human eotaxin (Example 3) was shown to bind to cells which are transfected with a gene encoding a human C-C chemokine receptor-3 (FIG. 11), and to induce chemotaxis in response to binding (FIGS. 12A-12E). U.S. Ser. No. 08/375,199 describes mammalian C-C CKR-3 genes, such as human CKR-3 genes, which can be made (e.g., by isolating the gene using PCR or by other suitable methods) based on the sequence shown in FIGS. 15A-15D.

In one embodiment, an isolated eotaxin receptor gene from, e.g., a mammal, is incorporated into an expression system to produce a receptor protein or polypeptide (essentially as described above for eotaxin). An isolated and/or recombinant eotaxin receptor, such as a receptor expressed in cells stably or transiently transfected with a construct comprising a nucleic acid which encodes an eotaxin receptor, or present in a cell fraction (e.g., membrane fraction from transfected cells, or further purified if desired) containing receptor, can be used in tests for eotaxin function and/or to identify inhibitors or promoters of eotaxin in vitro or in vivo.

For example, isolated and/or recombinant human C-C chemokine receptor 3 (CKR-3) gene, such as the gene illustrated in FIGS. 15A-15D, can be used in the present method. The effect of an agent is assessed by monitoring receptor function as described herein or using other suitable techniques. For example, stable or transient transfectants, such as stable tranfectants of mouse L1-2 pre-B cells (see e.g., Example 7) or insect cells (e.g., Sf9 cells) infected with a baculovirus vector comprising a nucleic acid encoding receptor can be used in binding assays. Stable transfectants of mouse L1-2 pre-B cells or of other suitable cells capable of chemotaxis can be used in chemotaxis assays, for example.

According to the method of the present invention, agents can be individually screened or one or more agents can be tested simultaneously. Where a mixture of compounds is tested, the agent(s) selected by the processes described can be separated (as appropriate) and identified by suitable methods (e.g., PCR, sequencing, chromatography). The presence of one or more agents (e.g., an inhibitor, promoter) in a test sample can also be determined according to these methods.

Combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 2678-2685 (1994) and references cited therein; see also, Ohlmeyer, M. H. J. et al., *Proc. Natl. Acad. Sci. USA*, 90:10922-10926 (1993) and DeWitt, S. H. et al., *Proc. Natl. Acad. Sci. USA*, 90:6909-6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible.

Other sources of potential inhibitors and/or promoters of eotaxin include, but are not limited to, substances such as other chemoattractants, such as a second human chemokine (e.g., RANTES, MCP-3), a chemokine from another mammal (e.g., for a human receptor, a homolog of a human chemokine obtained from a non-human source); variants of other chemoattractants or chemokines, such as naturally occurring, synthetic or recombinant variants; other mammalian (e.g., human) CKR-3 receptor ligands, inhibitors and/or promoters (e.g., antibodies, antagonists, agonists), and variants thereof; other G-protein coupled receptor ligands, inhibitors and/or promoters (e.g., antagonists or agonists); and soluble portions of a mammalian CKR-3 receptor, such as a suitable receptor peptide or analog which can inhibit receptor function (see e.g., Murphy, R. B., WO 94/05695).

Binding Assays

The isolated and/or recombinant proteins of the present invention (e.g., synthetic predicted mature eotaxin, a fusion protein comprising predicted mature eotaxin) or portions thereof, can be used in a method to select and/or identify agents or compounds which bind to or inhibit binding of human eotaxin to an eotaxin receptor (e.g., human CKR-3 receptor or other receptor present on leukocytes such as eosinophils) and which are potential inhibitors or promoters of human eotaxin. Agents selected by the method, including ligands, inhibitors or promoters, can be further assessed for an inhibitory or stimulatory effect on human eotaxin function and/or for therapeutic utility.

In one embodiment, agents which bind to a mammalian (e.g., human) chemokine receptor protein that binds human eotaxin are identified by the method. Binding function of proteins of the present invention such as a human eotaxin, a portion thereof or variant of human eotaxin can also be assessed in this manner. For example, an isolated and/or recombinant chemokine receptor protein (e.g., CKR-3) can be maintained under conditions suitable for binding, the receptor is contacted with an agent to be tested or a protein of the present invention (e.g., human eotaxin), and binding is detected or measured. In one embodiment, eosinophils expressing a (at least one type) receptor which binds human eotaxin are used. In another embodiment, a receptor protein can be expressed in cells stably or transiently transfected with a construct comprising a nucleic acid sequence which encodes a receptor for eotaxin. The cells are maintained under conditions appropriate for expression of receptor, and are contacted with an agent or a protein of the present invention (e.g., human eotaxin, portion thereof, or a variant) under conditions suitable for eotaxin binding to receptor (e.g., in a suitable binding buffer), and binding is detected by standard techniques. To measure binding, the extent of binding can be determined relative to a suitable control (e.g., compared with background determined in the absence of agent, compared with binding of a second agent (i.e., a standard), compared with binding of eotaxin to untransfected cells). Optionally, a cellular fraction, such as a membrane fraction, containing receptor can be used in lieu of whole cells.

In one embodiment, the agent or protein of the present invention is labeled with a suitable label (e.g., fluorescent label, isotope label), and binding is determined by detection of the label. Specificity of binding can be assessed by competition or displacement, for example, using unlabeled agent, an unlabeled isolated and/or recombinant human eotaxin, or a second ligand for receptor as competitor.

The binding activity of a promoter or inhibitor which binds receptor can be assessed using such a ligand binding assay. Receptors of human eotaxin, including human natural receptors or receptors from other mammalian species, can be identified in this manner.

Binding inhibition assays can also be used to identify inhibitors or promoters which bind a chemokine receptor which binds human eotaxin, and which can inhibit or promote, respectively, at least one human eotaxin function. For example, a binding assay can be conducted in which a reduction in the binding of isolated and/or recombinant human eotaxin (in the absence of an agent), as compared with binding of said human eotaxin in the presence of the agent, is detected or measured. The agent can be another protein of the present invention (e.g., a variant), for example. A receptor (e.g., isolated and/or recombinant receptor, cells bearing receptor or a membrane fraction containing receptor isolated from such cells) can be contacted with the human eotaxin and the agent simultaneously, or one after the other, in either order. A reduction in the extent of binding of the human eotaxin in the presence of the agent, is indicative of inhibition of binding by the agent. For example, binding of eotaxin could be decreased or abolished.

In one embodiment, direct inhibition of the binding of a human eotaxin to a chemokine receptor by a second test agent is monitored. For example, the ability of an agent to inhibit the binding of $^{125}$I-labeled eotaxin to human receptor (e.g., isolated receptor or receptor present on cells) can be monitored. Such an assay can be conducted using either whole cells (e.g., eosinophils, butyric acid-differentiated HL-60 cells, or a suitable cell line containing nucleic acid encoding a human C-C chemokine receptor such as CKR-3 receptor) or a membrane fraction from said cells, for instance.

Other methods of identifying an agent which binds a receptor which binds human eotaxin are available, such as methods which monitor events which are triggered by receptor binding, including leukocyte activation and/or stimulation (See below).

Receptor-binding inhibitors (e.g., antagonists) and promoters (e.g., agonists), which are identified in this manner, can be further assessed to determine whether, subsequent to binding, they act to inhibit or activate other functions of human eotaxin and/or to assess their therapeutic utility.

Assays for Leukocyte Activation

The activation function of protein of the present invention or a promoter of human eotaxin function, such as an agonist, can be monitored using any suitable method. The binding of a human eotaxin or promoter of human eotaxin function, such as an agonist, to a responsive receptor (e.g., a G protein-coupled receptor) can result in signalling, whereby the activity of a G protein is stimulated. G protein activity, such as hydrolysis of GTP to GDP, or later events triggered by receptor binding, can be assayed by methods known in the art or other suitable methods (see e.g., Neote, K. et al., Cell, 72: 415-425 (1993); Van Riper et al., J. Exp. Med., 177: 851-856 (1993); Dahinden, C. A. et al., J. Exp. Med., 179: 751-756 (1994); Sledziewski et al., U.S. Pat. No. 5,284, 746). Activity in such an assay is indicative of activation function.

Standard assays which monitor the induction of a rapid and transient increase in the concentration of intracellular (e.g., cytosolic) free calcium $[Ca^{2+}]_i$ (Example 5), exocytosis (e.g., of enzymes such as eosinophil peroxidase, β-glucuronidase), or inflammatory mediator release (e.g., histamine, leukotriene) can also be used to assess the response of leukocytes to a protein of the present invention (e.g., isolated human eotaxin) or a promoter. In addition, leukocyte integrin upregulation and/or activation can also be monitored.

In another embodiment, these assays can be used to identify potential inhibitors of eotaxin function. The inhibitory activity of an agent can be determined using a human eotaxin in the assay, and assessing the ability of an agent to inhibit the activity induced by eotaxin.

A protein of the present invention (e.g., a variant of human eotaxin) can also be screened for reduced ability (decreased ability or no ability) to stimulate activity of a coupled G protein or to stimulate a rapid and transient increase in the concentration of intracellular (cytosolic) free calcium $[Ca^{2+}]_i$, for instance. In this embodiment, although the protein has ligand binding activity (as determined by another method in advance or later), engagement of the receptor does not trigger or only weakly triggers activity of a coupled G protein. Such agents are potential antagonists, and can be further assessed using a suitable assay. For instance, the same assay can be conducted in the presence of an active human eotaxin, a portion thereof, or an active variant of human eotaxin, and the ability of the agent to inhibit the activity of a ligand or promoter is assessed.

Chemotaxis Assays and Assays of Leukocyte Stimulation

Chemotaxis assays can also be used to assess or measure function of proteins of the present invention. These assays are based on the functional migration of cells in vitro or in vivo induced by a compound, and can be used to assess the binding and/or chemoattractant effect of e.g., human eotaxin, inhibitors or promoters of human eotaxin function. The use of an in vitro transendothelial chemotaxis assay is described in Example 4 (see also FIG. 3). Springer et al. describe a transendothelial lymphocyte chemotaxis assay (Springer et al., WO 94/20142, published Sep. 15, 1994, the teachings of which are incorporated herein by reference; see also Berman et al., *Immunol Invest*. 17: 625-677 (1988)). Migration across endothelium into collagen gels has also been described (Kavanaugh et al., *J. Immunol*, 146: 4149-4156 (1991)).

Suitable cells capable of chemotaxis, such as eosinophils, stable transfectants of mouse L1-2 pre-B cells (or transfectants of other suitable host cells capable of chemotaxis) can be used in chemotaxis assays. Cells which express a receptor which can bind and is responsive to human eotaxin can also be incorporated into chemotaxis assays.

Generally, chemotaxis assays monitor the directional movement or migration of a suitable cell (such as a leukocyte (e.g., lymphocyte, eosinophil, basophil)) into or through a barrier (e.g., endothelium, a filter), toward increased levels of a compound, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored. In some assays, the membrane is coated with a substance to facilitate adhesion, such as ICAM-1, fibronectin or collagen.

For example, one can detect or measure the migration of cells in a suitable container (a containing means), from a first chamber into or through a microporous membrane into a second chamber which contains a compound to be tested, and which is divided from the first chamber by the membrane. A suitable membrane, having a suitable pore size for monitoring specific migration in response to compound, including, for example, nitrocellulose, polycarbonate, is selected. For example, pore sizes of about 3-8 microns, and preferably about 5-8 microns can be used. Pore size can be uniform on a filter or within a range of suitable pore sizes.

To assess migration, the distance of migration into the filter, the number of cells crossing the filter that remain adherent to the second surface of the filter, and/or the number of cells that accumulate in the second chamber can be determined using standard techniques (e.g., microscopy). In one embodiment, the cells are labeled with a detectable label (e.g., radioisotope, fluorescent label, antigen or epitope label), and migration can be assessed by determining the presence of the label adherent to the membrane and/or present in the second chamber using an appropriate method (e.g., by detecting radioactivity, fluorescence, immunoassay). The extent of migration induced by a compound can be determined relative to a suitable control (e.g., compared to background migration determined in the absence of the compound, to the extent of migration induced by a second compound (i.e., a standard), compared with migration of untransfected cells induced by the compound).

Chambers can be formed from various solids, such as plastic, glass, polypropylene, polystyrene, etc. Membranes which are detachable from the chambers, such as a Biocoat (Collaborative Biomedical Products) or Transwell (Costar, Cambridge, Mass.) culture insert, facilitate counting adherent cells.

In the container, the filter is situated so as to be in contact with fluid containing cells in the first chamber, and the fluid in the second chamber. Other than the test compound or additional ligand, inhibitor, or promoter present for the purpose of the assay, the fluid on either side of the membrane is preferably the same or substantially similar. The fluid in the chambers can comprise protein solutions (e.g., bovine serum albumin, fetal calf serum, human serum albumin) which may act to increase stability and inhibit nonspecific binding of cells, and/or culture media.

In a preferred embodiment, particularly for eosinophils, lymphocytes, or other cells expressing an eotaxin receptor, transendothelial migration is monitored. A transendothelial migration assay is preferred. Such assays are better physiological models, because they more accurately recapitulate in vivo conditions in which leukocytes emigrate from blood vessels toward chemoattractants present in the tissues at sites of inflammation by crossing the endothelial cell layer lining the vessel wall. In addition, transendothelial assays have lower background (signal to noise ratio).

In this embodiment, transmigration through an endothelial cell layer is assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells are available for monolayer formation, including for example, vein, artery or microvascular endothelium, such as human umbilical vein endothelial cells (Clonetics Corp., San Diego, Calif.) or a suitable cell line, such as the ECV 304 cell line used in Example 4. To assay chemotaxis in response to a protein of the present invention, endothelial cells of human origin or from a heterologous mammalian species or genus can also be used.

Generally, the assay is performed by detecting the directional migration of cells into or through a membrane or filter, in a direction toward increased levels of a compound, from a first surface of the filter toward an opposite second surface of the filter, wherein the filter contains an endothelial cell layer on a first surface. Directional migration occurs from the area adjacent to the first surface, into or through the membrane, towards a compound situated on the opposite side of the filter. The concentration of compound present in the area adjacent to the second surface, is greater than that in the area adjacent to the first surface.

In one embodiment, a chemotaxis assay is used to test for ligand or promoter activity of an agent. A composition comprising cells capable of migration and expressing suitable receptor are placed in the first chamber, and a composition comprising the agent to be tested (e.g., a human eotaxin or other compound) is placed in the second chamber, preferably in the absence of other ligands or promoters capable of inducing chemotaxis of the cells in the first chamber (having chemoattractant function). However, one or more ligands or promoters having chemoattractant function may be present. Compounds which can bind receptor and induce chemotaxis of the cells expressing an eotaxin receptor in this assay are ligands or promoters of receptor function. It will be apparent that the assay can also be used to identify and/or isolate a receptor of a human eotaxin.

In one embodiment used to test for an inhibitor, a composition comprising cells capable of migration in response to human eotaxin are placed in the first chamber. A composition comprising an isolated and/or recombinant human eotaxin, portion thereof or variant, and optionally, one or more other ligand(s) or promoter(s) also capable of inducing chemotaxis of the cells in the first chamber (having chemoattractant function), is placed in the second chamber. Either before the cells are placed in the first chamber, or simultaneously with the cells, a composition comprising the agent to be tested is placed, preferably, in the first chamber. Agents which can interfere with the ability of the human eotaxin, portion or variant to bind eotaxin receptor and inhibit the induction of chemotaxis, of the cells present in the first chamber are inhibitors of stimulatory function. A reduction in the extent of cell migration induced in the presence of the test agent is indicative of inhibitory activity. Separate binding studies (see above) could be performed to determine whether inhibition is a result of binding of the test agent to receptor or to the human eotaxin, portion or variant, or occurs via a different mechanism.

For instance, antibodies can be assessed for activity as inhibitors or promoters in a chemotaxis assay as described herein. For example, to assess inhibition, chemotaxis of eosinophils in response to a human eotaxin (in the lower chamber; see e.g., FIG. 3) can be monitored. For example, an antibody (e.g., an antibody raised against a synthetic human eotaxin) can be placed in the lower chamber and the effect on chemotaxis in response to the human eotaxin can be assessed. As a control, chemotaxis in response to a human eotaxin in a no antibody control or in the presence of a control antibody (e.g., preimmune serum) (placed in the lower chamber with chemokine) is measured.

In vivo assays which monitor leukocyte infiltration of a tissue, in response to injection of an agent such as a human eotaxin or promoter of human eotaxin, are described below (Models of Inflammation; Example 10). These models measure the ability of cells to respond to a ligand or promoter by emigration and chemotaxis to a site of inflammation. The effect of an inhibitor on leukocyte infiltration induced by a ligand or promoter can also be assessed in this type of assay.

In addition to the methods described, the effects of a human eotaxin, inhibitor or promoter of human eotaxin on the stimulatory function mediated through receptor binding can be assessed by monitoring cellular responses induced by active receptor, using eosinophils or suitable host cells containing receptor. Similarly, these assays can be used to determine the identity and function of a receptor. For instance, exocytosis (e.g., degranulation of eosinophils leading to release of eosinophil cationic protein and/or one or more enzymes, or other granule components; release of histamine from basophils), inflammatory mediator release (such as release of bioactive lipids such as leukotrienes (e.g., leukotriene $C_4$)), and respiratory burst (Rot, A. et al., *J. Exp. Med.*, 176: 1489-1495 (1992)), can be monitored by methods known in the art or other suitable methods. See e.g., Bischoff, S. C. et al., Eur. *J. Immunol.* 23: 761-767 (1993) and Baggiolini, M. and C. A. Dahinden, *Immunology Today*, 15:127-133 (1994) and references cited therein).

In one embodiment, a human eotaxin, inhibitor or promoter is identified by monitoring the release of an enzyme upon degranulation or exocytosis by a cell capable of this function. Suitable cells capable of exocytosis or degranulation in response to receptor binding, including leukocytes (e.g., eosinophils, basophils) or other cells expressing an eotaxin receptor, such as those containing a nucleic acid which encodes a receptor protein, are maintained in a suitable medium under suitable conditions (e.g., whereby receptor is expressed and whereby degranulation can be induced). The cells are contacted with an agent to be tested, and enzyme release is assessed. The release of an enzyme into the medium can be detected or measured using a suitable assay, such as in an immunological assay, or biochemical assay for enzyme activity.

The medium can be assayed directly, by introducing components of the assay (e.g., substrate, co-factors, antibody) into the medium (e.g., before, simultaneous with or after the cells and compound are combined). Alternatively, the assay can be performed on medium which has been separated from the cells or further fractionated prior to assay.

For example, convenient assays are available for enzymes such as β-glucuronidase and eosinophil peroxidase (White, S. R. et al., A kinetic assay for eosinophil peroxidase activity in eosinophils and eosinophil conditioned media, *J. Immunol. Methods*, 144(2): 257-63 (1991)).

Stimulation of degranulation by an agent can be indicative that the agent is a promoter of human eotaxin. Inhibition of degranulation is indicative of an inhibitor. In this embodiment, the cells are combined with a ligand or promoter, and a compound to be tested is added before, after or simultaneous therewith.

Models of Inflammation

A variety of in vivo models of inflammation are available, which can be used to assess the effects of human eotaxin (or of inhibitors or promoters thereof) in vivo as therapeutic and/or prophylactic agents.

For example, primate models with eosinophilic infiltration to the lung, are available for in vivo testing (see e.g., Wegner, C. D. et al., *Science*, 247: 456 (1990)). In one embodiment, an antibody (e.g., a monoclonal antibody) reactive with human eotaxin, and which cross-reacts with primate eotaxin, is administered to the animal. In another embodiment, an active human eotaxin, portion or variant is administered to the animal to induce inflammation before, simultaneously with or after administration of an antibody reactive with the human eotaxin polypeptide. A number of parameters can be measured to assess in vivo efficacy including, but not limited to, the number of eosinophils in a sample (e.g., in bronchoalveolar lavage fluid), respiratory compliance, and respiratory rate. A decrease in symptoms of airway hypersensitivity can also be indicative of therapeutic benefit.

In addition, a sheep model for asthma, a guinea pig model for passive cutaneous anaphylaxis, or other suitable models can be used to assess an agent (e.g., an antibody) in vivo (see e.g., Weg, V. B. et al., *J. Exp. Med.*, 177: 561 (1993); Abraham, W. M. et al., *J. Clin. Invest.*, 93: 776 (1994)).

In addition, leukocyte infiltration upon intradermal injection of an agent into a suitable animal, such as a primate (e.g., rhesus monkey), rabbit, rat, mouse or guinea pig, can be monitored (Example 10; see also, Van Damme J. et al., *J. Exp. Med.*, 176: 59-65 (1992); Zachariae, C. O. C. et al., *J. Exp. Med.* 171: 2177-2182 (1990); Jose, P. J. et al., *J. Exp. Med.* 179: 881-887 (1994)). In one embodiment, skin biopsies are assessed histologically for infiltration of leukocytes (e.g., eosinophils, granulocytes). In another embodiment, labeled cells (e.g., stably transfected cells expressing an eotaxin receptor, labeled with $^{111}$In for example) capable of chemotaxis and extravasation are administered to the animal. Infiltration of cells in response to injection of a test sample (e.g., an agent to be tested in a suitable buffer or physiological carrier) is indicative of the presence of a human eotaxin or promoter, such as an agonist, in the sample. These assays can also be modified to identify inhibitors of chemotaxis and leukocyte extravasation. For example, an inhibitor can be administered, either before, simultaneously with or after a human eotaxin polypeptide or agonist is administered to the test animal. A decrease in the extent of infiltration in the presence of inhibitor as compared with the extent of infiltration in the absence of inhibitor is indicative of inhibition.

Diagnostic Applications

The present invention has a variety of diagnostic applications. These applications include, but are not necessarily limited to the applications discussed herein.

Mutation(s) in genes encoding a human eotaxin can cause defects in at least one function of the encoded polypeptide, thereby reducing or enhancing eotaxin function. For instance, mutations which produce a variant of eotaxin or alter the level of expression, can reduce or enhance eotaxin function, thereby reducing or enhancing, the inflammatory processes mediated by eotaxin.

For example, the nucleic acids of the present invention provide reagents (e.g., probes, PCR primers) which can be used to identify, screen for, characterize and/or isolate a defective human eotaxin gene, which encodes a polypeptide having reduced or enhanced activity relative to a standard (e.g., wild type). Standard methods of screening for a defective gene can be employed, for instance. A defective gene can be isolated and expressed in a suitable host cell for further assessment of the gene and/or encoded protein.

In one embodiment, the methods of detecting or measuring eotaxin can be used diagnostically to characterize the activity of eotaxin produced by an individual. In these assays, reduced or enhanced eotaxin function can be assessed. For example, antibodies raised against a protein of the present invention (see above) can be used in the diagnosis of diseases or conditions in which increased or decreased leukocyte (especially eosinophil) activation or stimulation are observed, as indicated by, for example hypereosinophilia (e.g., in hypereosinophilic syndrome) or hypoeosinophilia.

In one embodiment, antibodies of the present invention can be used to detect or measure decreased or increased expression of eotaxin in various diseases or conditions in which inflammatory processes of leukocytes are altered (e.g., increased or decreased relative to a suitable control, such as the level of expression in a normal individual). The antibodies of the present invention can be used in procedures in which human eotaxin is detected in a sample (e.g., tissues or body fluids from an individual such as blood, serum, bronchoalveolar lavage fluid, saliva, bowel fluid). For example, a sample (e.g., tissue and/or fluid) can be obtained from an individual and a suitable immunological method can be used to assess the level of expression. Suitable methods include methods such as enzyme-linked immunosorbent assays (ELISA), including chemiluminescence assays, radioimmunoassay, and immunohistology. For instance, the presence of an increased level of eotaxin reactivity in a sample obtained from an individual can be indicative of inflammation and/or leukocyte (e.g., eosinophil) infiltration and/or accumulation associated with an inflammatory disease or condition, such as asthma, allergic rhinitis, or an infection, such as a parasitic infection. The colocalization of elevated levels of eotaxin and leukocytes such as eosinophils in inflamed tissue (nasal polyp) compared with controls, as assessed immunohistologically with anti-eotaxin monoclonal antibodies, establishes an association between eotaxin and inflammation (Example 9). 1

Transgenic Animals

Transgenic animals, in which the genome of the animal host is altered using recombinant DNA techniques, can be constructed. In one embodiment, the alteration is not heritable (e.g., somatic cells, such as progenitor cells in bone marrow, are altered). In another embodiment, the alteration is heritable (the germ line is altered). Transgenic animals can be constructed using standard techniques or other suitable methods (see e.g., Cooke. M. P. et al., *Cell*, 65: 281-291 (1991) regarding alteration of T lymphocytes; Hanahan, D., *Science*, 246: 1265-1275, (1989)).

In one aspect, an endogenous mammalian eotaxin gene can be inactivated or disabled, in whole or in part, in a suitable animal host (e.g., by gene disruption techniques) to produce a transgenic animal. Nucleic acids of the present invention can be used to assess successful construction of a host containing an inactivated or disabled eotaxin gene (e.g., by Southern hybridization). In addition, successful construction of a host containing an inactivated or disabled eotaxin gene can be assessed by suitable assays which monitor the function of the encoded protein.

In another embodiment, a nucleic acid encoding a human eotaxin, portion thereof or variant, is introduced into a suitable host to produce a transgenic animal. In a preferred embodiment, endogenous eotaxin genes present in the transgenic animals are inactivated (e.g., simultaneously with introduction of the nucleic acid by homologous recombination, which disrupts and replaces the endogenous gene). For example, a transgenic animal (e.g., a mouse, guinea pig, sheep) capable of expressing a nucleic acid encoding a human eotaxin in leukocytes (such as eosinophils, lymphocytes (e.g., T lymphocytes)) can be produced, and provides a convenient animal model for assessing the function of the introduced gene and encoded protein (Jose et al., *Biochem. Biophys. Res. Commun.*, 205(1): 788-794 (1994); Rothenberg et al., *J. Exp. Med.*, 181: 1211-1216 (1995)). In addition, an agent can be administered to the transgenic animal, and the effect of the agent on an inflammatory process mediated by eotaxin can be monitored in a suitable assay (see e.g., Weg, V. B. et al., *J. Exp. Med.*, 177: 561 (1993); Abraham, W. M. et al., *J. Clin. Invest.*, 93: 776 (1994)). In this manner, agents which are inhibitors or promoters of eotaxin can be identified or assessed for in vivo effect.

Methods of Therapy

Modulation of human eotaxin function according to the present invention, through the inhibition or promotion of at least one function characteristic of human eotaxin, provides an effective and selective way of inhibiting or promoting leukocyte-mediated inflammatory action. One or more inhibitors and/or promoters of human eotaxin function, such as those identified as described herein, can be used to modulate leukocyte function for therapeutic and/or prophylactic purposes.

As major eosinophil chemokine, eotaxin provides a target for selectively interfering with or promoting leukocyte, especially eosinophil function in a primate, such as a human. Accumulation of eosinophils is observed in certain inflammatory infiltrates. As shown herein, a synthetic human eotaxin can recruit eosinophils in vivo (Example 10). The present invention provides a method of inhibiting or promoting an inflammatory response in an individual (e.g., a primate, such as a human), comprising administering an agent which inhibits or promotes eotaxin function to an individual in need of therapy or prophylaxis. Thus, agents which inhibit or promote human eotaxin function, inhibitors and promoters identified according to the present method, including human eotaxins (e.g., an isolated and/or recombinant human eotaxin having the same amino acid sequence as a naturally occurring human eotaxin) are particularly useful for modulating eosinophil function for therapeutic and/or prophylactic purposes.

In one embodiment, an agent which inhibits one or more functions of human eotaxin is administered to inhibit (e.g., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

In another embodiment, an agent which promotes one or more functions of eotaxin is administered to stimulate (e.g., induce or enhance) an inflammatory response, such as leukocyte (especially eosinophil) emigration, chemotaxis, exocytosis (e.g., of enzymes, histamine) or inflammatory mediator release, resulting in the beneficial stimulation of inflammatory processes. For example, eosinophils can be recruited to combat parasitic infections.

The term "individual" is defined herein to include animals such as mammals, including, but not limited to, humans, primates, cows, sheep, goats, horses, dogs, cats, guinea pigs, rats or other bovine, ovine, equine, canine, feline, rodent or murine species.

Diseases and conditions associated with inflammation and infection can be treated using the method. In a preferred embodiment, the disease or condition is one in which the actions of eosinophils and/or other leukocyte types are to be inhibited or promoted, in order to modulate the inflammatory response.

Diseases or conditions of humans especially, as well as non-human primates or other species which can be treated with inhibitors of human eotaxin function, include, but are not limited to:

- inflammatory or allergic diseases and conditions, including respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; inflammatory bowel diseases, such as Crohn's disease and ulcerative colitis; spondyloarthropathies; scleroderma; psoriasis and inflammatory dermatoses such as dermatitis, eczema, atopic dermatitis, allergic contact dermatitis, urticaria; vasculitis (e.g., necrotizing, cutaneous, and hypersensitivity vasculitis);
- eosinophilic myositis, eosinophilic fasciitis;
- autoimmune diseases, such as rheumatoid arthritis, psoriatic arthritis, multiple sclerosis, systemic lupus erythematosus, myasthenia gravis, juvenile onset diabetes, glomerulonephritis, autoimmune thyroiditis, Behcet's disease;
- graft rejection (e.g., in transplantation), including allograft rejection or graft-versus-host disease;
- cancers with leukocyte infiltration of the skin or organs;

other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans, non-human primates, or other species which can be treated with promoters of eotaxin function, include, but are not limited to:

immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due to congenital (or other) deficiency in eotaxin or other causes;

infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (fluxes) (Schistosomiasis, Clonorchiasis), cestodes (tape worms) (Echinococcosis, Taeniasis saginata, Cysticercosis); visceral worms, visceral larva migrans (e.g., *Toxocara*), eosinophilic gastroenteritis (e.g., *Anisaki* spp., *Phocanema* spp.), cutaneous larva migrans (*Ancylostoma braziliense, Ancylostoma caninum*).

Eosinophils as the Target Cell in Certain Inflammatory Reactions, Particularly Asthma Eosinophils are produced in the bone marrow and circulate to the tissues, predominantly to mucosal tissues, such as the lungs, gastrointestinal tract, and genitourinary tract. Eosinophils typically constitute 1-3% of leukocytes in the blood. However, in people suffering from allergic diseases and helminthic parasitic infections, increased eosinophil accumulation occurs in the tissues or the blood. Eosinophils accumulation can be both beneficial and detrimental to the host.

For example, eosinophils possess numerous granules, containing cationic proteins. Degranulation of eosinophils, triggered, for example, by the engagement of IgG, IgA, or IgE receptors, or by stimulation by inflammatory mediators such as platelet-activating factor (PAF), leukotrienes, or chemokines, leads to release of the components in the granule. Products from eosinophils also cause damage to host cells. The most damaging are the cationic proteins, which are detectable in elevated concentrations in patients with asthma. Eosinophils also generate a number of inflammatory mediators, including Leukotriene C4, and platelet-activating factor (PAF). These mediators contract airway smooth muscle, promote the secretion of mucus, alter vascular permeability, and elicit further eosinophil and neutrophil infiltration.

Eosinophils are involved in the initiation and maintenance of allergic/asthma diathesis. Thus, in a preferred embodiment, the method can be used to treat asthma or hypersensitivity (allergic) states, particularly those involving mucosal tissues, as well as in other eosinophil-associated diseases. In a particularly preferred embodiment, an agent (e.g., an antibody) which inhibits one or more functions of human eotaxin is administered to an individual with asthma.

Eosinophils are clearly important in the host defense against and destruction of, large, nonphagocytable organisms, such as multicellular helminthic parasites. Eosinophils are also important effector cells in immune reactions against other pathogens that induce high levels of IgE antibodies. Accordingly, the method can be used to treat infectious diseases, such as parasitic diseases, to stimulate or promote inflammatory defenses, or to suppress inflammatory responses which are destructive to the host.

Eosinophils and Asthma Pathogenesis

Asthma is characterized by the obstruction of the airways or bronchi, and results from a bronchial hyperresponsiveness and rapid constriction in response to a wide range of pharmacological mediators. Chronic inflammation of the bronchial mucosal lining is believed to play a fundamental role in the development of asthma.

Intense infiltration of the bronchial mucosa with eosinophils, macrophages and lymphocytes is observed in asthma and other hypersensitivities. Often the selective migration of eosinophils to inflamed airways can be striking, and appears to result from the selective binding of eosinophils to endothelium and extraction from the blood. Eosinophils in particular are implicated as the causative agents of bronchial mucosal injury. Studies of asthmatic patients suggest that blood eosinophil counts correlate with the degree of bronchial hyperresponsiveness. In addition, bronchial biopsies and bronchoalveolar lavage fluid from asthmatics show a clear relationship between the degree of eosinophilia and clinical severity. Thus, there is a strong connection between the presence of eosinophils and adverse immune reactions, particularly in asthma.

A novel human chemokine that selectively stimulates activation, chemotaxis, and/or extravasation of leukocytes such as eosinophils, provides an excellent target for interfering with eosinophil recruitment. For example, administration of an inhibitor of at least one function of human eotaxin, such as by inhibiting binding to a receptor which binds thereto, can provide an effective and selective way of treating asthma. By reducing or preventing recruitment (extravasation, infiltration) of leukocytes, particularly eosinophils, to inflamed lung and airway tissues, and/or reducing leukocyte (especially eosinophil) function in those tissues, the destructive inflammatory processes of asthma can be inhibited, and the symptoms alleviated.

There is evidence that the blockage of eosinophil recruitment to the lung can alleviate the symptoms of asthma. Administration of a monoclonal antibody reactive with $\alpha 4$ integrin was reported to inhibit the accumulation of eosinophils into the lung and airways, and blocked the airway hyperresponsiveness to antigen challenge in sheep. In a primate model of asthma, a monoclonal antibody to ICAM-1 is reported to attenuate airway eosinophilia and hyperresponsiveness. In addition, in a guinea pig model for passive cutaneous anaphylaxis, in vitro pretreatment of eosinophils with the anti-$\alpha 4$ monoclonal was reported to suppress eosinophil accumulation. (see Wegner, C. D. et al., *Science*, 247: 456 (1990); Weg, V. B. et al., *J. Exp. Med*., 177: 561 (1993); and Abraham, W. M. et al., *J. Clin. Invest*., 93: 776 (1994) regarding these models).

Desensitization of Eosinophils

RANTES, which is a chemoattractant of monocytes and T cells, is also a chemoattractant for eosinophils. RANTES binds specifically and with high affinity to CKR-3 receptor protein (U.S. Ser. No. 08/375,199, filed Jan. 19, 1995). As shown herein (FIGS. 6A-6E), an isolated, purified human eotaxin of the present invention can desensitize eosinophils to RANTES or to human eotaxin. Moreover, the desensitization appears to be specific for the CKR-3 receptor, as eotaxin did not desensitize eosinophils to anaphylatoxin C5a, which binds to eosinophils through a distinct receptor. Thus, the present invention provides a method of desensitizing eosinophils to chemokines which activate and/or stimulate eosinophil function. Receptor-specific desensitization in which eosinophils are rendered unresponsive or less responsive to one or more ligands of a selected chemokine receptor present on eosinophils, is possible according to the present invention. Eosinophils in blood or tissues, can be desensitized to RANTES and/or human eotaxin present in e.g., lungs or airways, whereby eosinophil activation and/or stimulation is inhibited (reduced or prevented). The method of desensitizing eosinophils is useful therapeutically and/or prophylactically in the treatment of inflammatory or allergic diseases and conditions, particularly allergic hypersensitivity diseases (e.g., allergic rhinitis, asthma).

The specificity of desensitization permits specific inhibition of eosinophil function (e.g., activation and/or stimulation) triggered by engagement of the specific C-C chemokine receptor. In a preferred embodiment, the agent administered desensitizes eosinophils, but has reduced eosinophil activation function, and preferably reduced induction of exocytosis and/or inflammatory mediator release (e.g., as compared with naturally occurring human eotaxin or a protein having the same amino acid sequence as naturally occurring human eotaxin).

According to the method, isolated and/or recombinant human eotaxin, a functional portion thereof or functional variant of human eotaxin is administered to an individual (e.g., a human) in a therapeutically effective amount (e.g., an amount sufficient to desensitize eosinophils in the blood and/or tissues, whereby inflammation due to eosinophil activation and/or stimulation is inhibited (reduced or prevented)). The isolated and/or recombinant human eotaxin, functional portion thereof or variant of human eotaxin can be administered by a suitable route (see below).

Eosinophils and Cancer

Cellular infiltrates containing predominantly eosinophils and macrophages have been observed in the area surrounding a plasmacytoma in a mouse model (Tepper, R. I. et al., *Cell*, 57: 503-512 (1989)). The present invention provides a method of anti-tumor therapy, in which an isolated and/or recombinant human eotaxin, a functional portion thereof or functional variant of human eotaxin is used in tumor therapy to specifically recruit eosinophils to the site of a tumor (e.g., a solid tumor such as a melanoma, carcinoma, sarcoma or leukemia (e.g., lymphoma with infiltration)). In one embodiment, colon cancer can be treated according to the claimed method. In particular, isolated and/or recombinant human eotaxin, a functional portion thereof or variant of human eotaxin is administered to an individual (e.g., a human) in a therapeutically effective amount (e.g., an amount sufficient to recruit eosinophils to the site, whereby tumor growth is inhibited and/or induced tumor regression occurs). The isolated and/or recombinant human eotaxin, a functional portion thereof or variant of human eotaxin is administered by a suitable route, and preferably by injection (e.g., intratumoral injection or injection), to achieve a local concentration sufficient for an anti-tumor effect.

Modes of Administration

According to the method, one or more agents can be administered to the host by an appropriate route, either alone or in combination with another drug. An effective amount of an agent (e.g., a peptide which inhibits eotaxin binding, an antibody or antibody fragment) is administered. An effective amount is an amount sufficient to achieve the desired therapeutic or prophylactic effect, under the conditions of administration, such as an amount sufficient for inhibition or promotion of chemokine (e.g., human eotaxin) function, and thereby, inhibition or promotion, respectively, of an inflammatory response.

A variety of routes of administration are possible including, but not necessarily limited to oral, dietary, topical, parenteral (e.g., intravenous, intraarterial, intramuscular, subcutaneous injection), and inhalation (e.g., intrabronchial, intranasal or oral inhalation, intranasal drops) routes of administration, depending on the disease or condition to be treated. For respiratory allergic diseases such as asthma, inhalation is a preferred mode of administration.

Formulation of an agent to be administered will vary according to the route of administration selected (e.g., solution, emulsion, capsule). An appropriate composition comprising the agent to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Science*, 16th Edition, Mack, Ed. 1980). For inhalation, the agent is solubilized and loaded into a suitable dispenser for administration (e.g., an atomizer, nebulizer or pressurized aerosol dispenser).

Furthermore, where the agent is a protein or peptide (such as a human eotaxin), the agent can be administered via in vivo expression of the recombinant protein. In vivo expression can be accomplished via somatic cell expression according to suitable methods (see, e.g., U.S. Pat. No. 5,399,346). In this embodiment, the DNA encoding the protein can be incorporated into a retroviral, adenoviral or other vector (preferably, a replication deficient infectious vector) for delivery, or can be introduced into a transfected or transformed host cell capable of expressing the protein for delivery. In the latter embodiment, the cells can be implanted (alone or in a barrier device) or injected in an amount effective to express the protein in a therapeutically effective amount.

EXEMPLIFICATION

The present invention will now be illustrated by the following Examples, which are not intended to be limiting in any way.

Example 1

Isolation of a Human Genomic Clone

The reported guinea pig eotaxin amino acid sequence (Jose, P. J. et al., *J. Exp. Med.*, 179: 881-887 (1994)) was used to design degenerate primers for polymerase chain reaction (PCR) amplification of sequences from both human genomic DNA and human asthmatic lung tissue. Clones were isolated and analyzed by DNA sequencing. Of ~25 clones sequenced, some clones shared sequence similarity to known chemokines, but none appeared to be sufficiently related to guinea pig eotaxin to be the human homolog.

Next, a fragment isolated from a mouse cDNA clone designated Clone 28, was used as a probe. Clone 28 (provided by Jose-Carlos Gutierrez-Ramos, Center for Blood Research, Boston, Mass.), was obtained by reverse transcription and polymerase chain reaction using an RT-PCR kit (Perkin-Elmer) with RNA isolated from inflamed, eosinophilic lung tissue obtained from BALB/c mice sensitized to ovalbumin (OVA) in an experimentally induced inflammation model. The degenerate primers used in RT-PCR for the isolation of Clone 28 were designed based on the guinea pig eotaxin amino acid sequence. Restriction digestion of Clone 28 with EcoRI released a ~200 bp Eco RI fragment from the pCR™II vector of the clone. The fragment was separated from vector by agarose gel electrophoresis, and purified by electroelution. Approximately 200 ng of material was labeled with $^{32}$p using a Random Primed DNA Labeling Kit (Boehringer Mannheim) according to the manufacturer's recommended protocol. Library screening A human genomic library in vector EMBL3 SP6/T7 was purchased from Clontech (Catalog No. HL 1111). For each of thirty 150 mm plates, approximately 25,000 plaque forming units were mixed with 600 μls of an overnight bacterial culture of *E. coli* strain K802 (provided with the library) in NZCYM top agarose, and plated on a 150 mm petri dish containing NZCYM agar (NZYCM broth, agar and agarose were purchased from Gibco/BRL). After incubation at 37° for 7 hours, the plates were overlaid with BA-85 nitrocellulose membranes (Schleicher and Schuell, Keene, NH) for 10 minutes to allow transfer of phage to membrane. The membranes were then soaked for 5 minutes in Denaturing Solution (1.5 M sodium chloride, 0.5 N sodium hydroxide) followed by neutralization in 1.5 M sodium chloride, 0.5 M Tris, pH 8.0. The filters were allowed to air dry for 15 minutes and were then baked for two hours at 800° C. under vacuum. Hybridization with the probe (see above) was carried out overnight at 65° C. in 6×SSC (1×SSC is 0.15 M sodium chloride, 0.015 M sodium citrate) containing 5× Denhardt's solution (1× Denhardt's solution is 0.02% bovine serum albumin, 0.02% ficoll, 0.02% polyvinylpyrolidone), 10% w/v dextran sulfate, 2% SDS, and sheared salmon sperm DNA (100 μg/ml). The membranes were rinsed twice in 2×SSC, 0.5% SDS at 65° C. (5 min each), followed by two washes (15 min each) in 0.2×SSC, 0.5% SDS at 55° C.

Eleven positive clones were detected using these conditions of moderate stringency. Plaques were picked from the primary library screen, and were purified by diluting the primary phage several fold and reprobing with the original probe until a single well-isolated positive plaque was obtained. One phage clone, designated Clone 25 (also referred to as 25H3), having an approximately 15-20 kb insert, was found to contain a sequence sharing similarity to that reported for guinea pig eotaxin. The coding region for this human gene was contained within a ~5.5 kb PstI fragment present in Clone 25. This PstI fragment was subcloned into the PstI site of Bluescript® II KS+ (Stratagene) to yield a construct designated 25PstI. Transformants of 25PstI in DH5a were obtained. The insert of 25PstI was subjected to sequence analysis using the Sequenase™ 7-deaza-dGTP DNA Sequencing Kit with Sequenase Version 2.0 T7 DNA polymerase (United States Biochemical (USB), Amersham Life Science). The sequence determined for the human gene is presented in FIGS. 1A-1B (SEQ ID NO:1).

Example 2

Isolation of a Human cDNA Clone

Using specific primers, a candidate human eotaxin cDNA clone was subsequently amplified by RT-PCR (reverse transcription, polymerase chain reaction) from RNA isolated from spleen, thymus, eosinophils, and monocytes in separate amplification reactions. Spleen and thymus mRNA were purchased from Clontech (spleen RNA, Catalog No. 6542-1; thymus RNA, Catalog No. 6536-1). Eosinophils and monocytes were isolated as described below in Example 4, and total RNA was isolated using TRIzol™ Reagent (GIBCO/BRL) according to the manufacturer's protocol.

20-50 ng of mRNA or 5 μg of total RNA was reverse transcribed with oligo dT. 2-5 μl of this cDNA was mixed with 200 μM dNTPs and 50-100 pmol of primer in a 50 μl volume for amplification with 5 units of Amplitaq polymerase. Magnesium concentration was 2.5 mM. The primers used for PCR amplification were:

5' primer (SEQ ID NO:7):

```
         Bam HI
5'- GGA TCC AAC ATG AAG GTC TCC G-3'
```

3' primer (SEQ ID NO:8):

```
      Eco RI
5'- GAA TTC TTA TGG CTT TGG AGT TGG AG-3'
```

The cycle parameters for PCR were as follows:
95° C., 1 minute;
25 cycles of:
  94° C., 30 seconds;
  68° C., 10 seconds;
  72° C., 10 seconds;
72° C., 6 minutes.

The amplification reaction yielded a single size of fragment (~300 bp). The PCR product was gel purified, digested with BamHI and EcoRI, and inserted into the BamHI and EcoRI sites of plasmid Bluescript® II KS+ (Stratagene) to yield a cDNA clone designated #25. cDNA clone #25 was produced by RT-PCR from spleen. Transformants of the #25 clone in DH5α were obtained. The insert of cDNA clone #25 was subjected to sequence analysis using the Sequenase™ 7-deaza-dGTP DNA Sequencing Kit with Sequenase Version 2.0 T7 DNA polymerase (United States Biochemical (USB), Amersham Life Science).

The sequence of the human cDNA determined from cDNA clone #25 is presented in FIG. 2 (SEQ ID NO:3). The encoded protein contains the paired, adjacent cysteine residues typical of C-C chemokines at positions 32-33. Alignment of the amino acid sequence of the protein encoded by cDNA clone #25 with other C-C chemokines indicates that the encoded protein also has a leader sequence for secretion. Based on the alignment with other C-C chemokines, the leader sequence corresponds to amino acids 1-23 of the predicted protein, and the mature protein begins with amino acid 24 ($Gly^{24}$).

The amino acid sequence of the predicted mature polypeptide encoded by clone #25 (residues 24-97) was compared to that of other known C-C chemokines (without leader peptides)(including human MCP-1, human MCP-2, guinea pig eotaxin, human MCP-3, human MIP-1β, human MIP-1α, and human RANTES) using the Lasergene Biocomputing Software from DNASTAR (Madison, Wis.). In addition, the complete open reading frame of the human cDNA (including the nucleotides encoding the leader peptide) was compared to those of other known C-C chemokines. The results of this analysis indicated that the predicted mature human protein encoded by cDNA #25 shares 64%, 62.7%, 62.7% and 58.1% amino acid sequence similarity with human MCP-1, human MCP-2, human MCP-3, and guinea pig eotaxin, respectively. Other sequences were less related. Given the sequence similarity with MCP-1, a monocyte and T cell chemoattractant, the biological activity of the protein encoded by clone #25 was assessed in order to establish its relationship to the other C-C chemokines. At the nucleotide level, the human cDNA #25 sequence was found to share 72.1% and 74.6% nucleic acid sequence similarity with human MCP-1 and guinea pig eotaxin, respectively, and to share 75.6% sequence similarity with the sequence of the mouse gene used as a probe.

As described in more detail below, the predicted mature protein encoded by genomic clone 25 (Example 1) and cDNA clone #25 has been produced. As is further described herein, the protein is a potent and specific chemoattractant for eosinophils, and therefore is referred to herein as human eotaxin. This novel chemotactic cytokine can be classified as a member of the C-C branch of chemotactic cytokines.

Example 3

Chemical Synthesis and Purification of Human Eotaxin

Chemical Synthesis

A human eotaxin polypeptide (amino acids 24-97) was synthesized by using solid-phase methods (Merrifield, R. B., *J. Am. Chem. Soc.* 85: 2149-2154 (1963)) that were optimized and adapted to a fully automated peptide synthesizer (Applied Systems 430A) and described in detail elsewhere (Clark-Lewis, I. et al., *Science* 231: 134-139 (1986); Clark-Lewis, I. and S. Kent, (1989), In: *The Use of HPLC in Receptor Biochemistry*, Kerlavage, A. R., Ed., (Alan R. Liss: New York) pp. 43-75; and Kent, S. B. H., *Annu. Rev. Biochem.* 57: 957-989 (1988)). The synthesis was started with the protected C-terminal amino acid linked to a cross-linked polystyrene resin via a 4-(carboxamidomethyl)benzyl ester linkage (pam resin) (0.4 mmol of 0.8 mmol/g of aminoacyl resin). $N^\alpha$-t-Boc amino acids with appropriate side chain protecting groups were added in a step wise fashion until the entire protected polypeptide chain was formed. Side chain protection was as follows: benzyl (Asp, Glu, Ser, Thr); 4-methylbenzyl (Cys); toluenesulfenyl (Arg); 2-chlorobenzyloxycarbonyl (Lys); 2-bromobenzyloxycarbonyl (Tyr); formyl (Trp); dinitrophenyl (His); and none (Ala, Asn, Gly, Gln, Ile, Leu, Met, Phe, Pro, Val). Samples were automatically taken after each step to retrospectively monitor the amino acid coupling yields using ninhydrin-based reaction (Sarin, V. K. et al., *Anal. Biochem.* 117: 147-157 (1981)).

The resin was dried and cleaved by using the "low-high" hydrogen fluoride method as described (Tam, J. P. et al., *J. Am. Chem. Soc.* 105: 6442-6455 (1983)), except for the following modifications. After the 25% hydrogen fluoride step, the partially protected peptide resin was filtered from the reaction mixture by using an all-Teflon filtration apparatus fitted with a Zitex filter and washed with dichloromethane and dried before the high 90% hydrogen fluoride step. The ethyl acetate precipitation of the material released from the resin was dissolved in 50 ml of 6M guanidine hydrochloride, 0.1 M Tris-acetate, pH 8.5, and 20% 2-mercaptoethanol and stirred at 37° C. for 2 hours and then acidified with 2 ml of acetic acid. This mixture was termed the crude peptide product.

HPLC Purification and Folding

Three different C-18 silica columns were used in the purification and analysis of the human protein, including (1) a preparative column (22.4×250 mm column with a 22.4× 100 mm guard column) packed with 12-µm, 300-Å pore size packing (Dynamax, Rainin Instrument Co., Woburn, Mass.); (2) a semipreparative (10×250 mm) Vydac C-18 column, with 5-mm particle, 300-Å pore size packing (Separations Group, Hesperia, Calif.); and (3) an analytical 4.6×250 mm column (Vydac) containing the same packing. The crude peptide product was loaded onto the preparative column and the retained material eluted with a 0-60% water-acetonitrile gradient in 0.1% trifluoroacetic acid over 4 hours at a flow rate of 15 ml per minute. A sample (25 µl) of fractions containing 225-nm UV-absorbing material was rerun on the analytical column, and by comparison with the profile of the crude material, fractions containing the major peak were pooled and lyophilized. This material was reconstituted in 1 M guanidine hydrochloride and Tris-acetate, pH 8.5, at a concentration of 0.2 mg/ml and stirred vigorously overnight in an open beaker so that air was kept bubbling through the mixture by vortex action. This procedure has been found to promote formation of the disulfide bridges by oxidation of the appropriate half-cystines (Clark-Lewis, I. et al., *Proc. Natl. Acad. Sci. USA*, 85: 7897-7902 (1988); Woo, D. D. L. et al., *Protein Eng.* 3: 29-37 (1989)). This material was acidified with 2 ml of acetic acid, and half was loaded onto the semipreparative column and the retained material eluted with the same gradient as before at a flow rate of 3 ml/min. Samples of each fraction were run on the analytical column. Fractions containing only material with the retention time of the major peak in the folded material were pooled and lyophilized as purified eotaxin.

Example 4

Human Eotaxin is Chemotactic for Eosinophils, but not Neutrophils, T Cells or Monocytes The chemotactic activity of the clone #25 polypeptide was assessed in a sensitive chemotaxis assay that employs transendothelial migration (Carr, M. W. et al., "Monocyte chemoattractant protein 1 acts as a T-lymphocyte chemoattractant," *Proc. Natl. Acad. Sci. U.S.A.*, 91: 3652-56 (1994)). Human eosinophils, neutrophils, peripheral blood mononuclear cells (PBMC), and activated T cells were analyzed for their response to different concentrations of synthetic protein (Example 3) and other chemokines.

Isolation and preparation of eosinophils, neutrophils, peripheral blood mononuclear cells, and activated T cells 100 ml of heparinized blood was diluted 1:1 with PBS. 20 ml aliquots were layered over 65%, 75% Percoll step gradients. The gradients were centrifuged at 1500 rpm, 25 min at room temp. The eosinophil/neutrophil layers were transferred to a new tube and erythrocytes lysed by addition of 20 mls 0.2% NaCl for 1 min followed by the addition of 30 mls 1.8% NaCl. Cells were washed twice with a buffer consisting of PBS, 0.5% BSA, 0.5 mM EDTA. Cells were resuspended at $5 \times 10^7$ cells/50 µl in cold buffer (PBS, 0.5% BSA, 0.5 mM EDTA) and 50 µl CD16 microbeads were added to the cells. The mixture was incubated at 4° C. for 25 min followed by the addition of 900 µl cold buffer. The miniMACS™ separation unit (Miltenyi Biotec, Inc., Auburn Calif. 95603) was used to deplete CD16 positive cells (neutrophils). Cells were loaded onto the column in 200 µl aliquots. Flow-through cells were collected and assessed histologically. The eosinophil prep was >99% pure.

For the isolation of neutrophils or peripheral blood mononuclear cells (including monocytes and lymphocytes), a standard protocol was followed (*Current Protocols in Immunology*, 1992, Coligan, J. E., A. M. Kruisbeek, D. H. Margulies, E. M. Shevach, and W. Strober, Editors, (John Wiley & Sons, New York, N.Y.), Unit 7.23). Activated T cells were prepared using anti-CD3 stimulation. Anti-CD3 mAb TR66 (obtained from Dr. A. Lanzavecchia, Basel Institute for Immunology, Basel) was coated onto 24 well plates, using a solution of 5 μg/ml in PBS. After a 1 hour incubation at 37° C., the unbound antibody was removed, the plate was washed four times with PBS, and $2 \times 10^6$ PBMC were added per well in RPMI 1640/10% fetal calf serum (FCS). Plates were incubated 3-4 days.

Monocytes were isolated using magnetic sorting with MACS using a prefilled and washed A2 column according to the Magnetic Sorting with MACS ($10^7$-$2 \times 10^8$ positive cells); Protocol for $10^7$ cells provided by the manufacturer (Miltenyi Biotec, Inc., Sunnyvale, Calif.). Positive cells were enriched for using a G23 needle.

Chemotaxis Assay

Chemokines were obtained from Peprotech, Inc. (Rocky Hill, N.J.), with the exception of MCP-2 and synthetic eotaxin (predicted mature eotaxin (amino acids 24-97); Example 3) which were chemically synthesized. Chemotaxis experiments were performed using 3.0 micron Biocoat cell culture inserts (Collaborative Biomedical Products), in 24 well plates. Endothelial cells were grown to confluency on the inserts for two days prior to chemotaxis experiments. The endothelial cells used were a cell line termed ECV 304 (European Collection of Animal Cell Cultures, Porton Down, Salisbury, U.K.), which expresses endothelial cell markers such as von Willebrand factor, as well as ICAM-1 and VCAM-1. This endothelial cell line greatly facilitates these assays, since human umbilical vein endothelial cells can be variable in nature, can be used for only several passages, and grow much more slowly than ECV 304.

ECV 304 cells were grown as adherent monolayers in M199/10% FCS, and were seeded onto the inserts ($2 \times 10^5$ cells per insert). Cells were incubated at 37° C. in the M199/10% FCS medium.

The assay buffer consisted of equal parts M199 and RPMI 1640, with 0.5% FCS. The assay was conducted at 37° C. for 1.5 hours, migrated cells were counted using either an inverted microscope, or a flow cytometer. Only cells which migrated completely into the bottom chamber were counted.

FIGS. 4A-4D illustrate the chemotaxis of leukocyte subpopulations in response to 100 ng/ml of chemokine present in the bottom chamber (MCP-1, MCP-2, MCP-3, MIP-1α (MIP-1a), RANTES, interleukin-8 (IL-8), IP-10 (a C-X-C chemokine; Peprotech), MIP-1β, or human eotaxin (synthetic mature eotaxin (amino acids 24-97)). As indicated above, chemotaxis plates were incubated at 37° C. for 90 minutes, and the cells which migrated to the bottom chamber were counted by microscopy (HPF=high power field). The results presented are a representative experiment of at least four experiments performed.

Figure 4A:
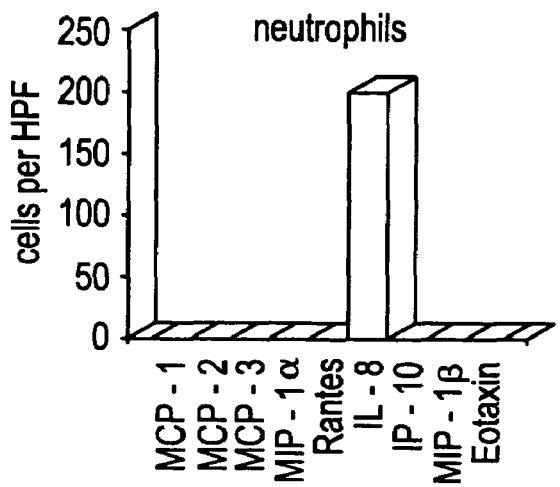
FIGS. 4A-4D are histograms illustrating the chemotaxis of human leukocyte subpopulations (FIG. 4A, neutrophils.
Figure 4C:
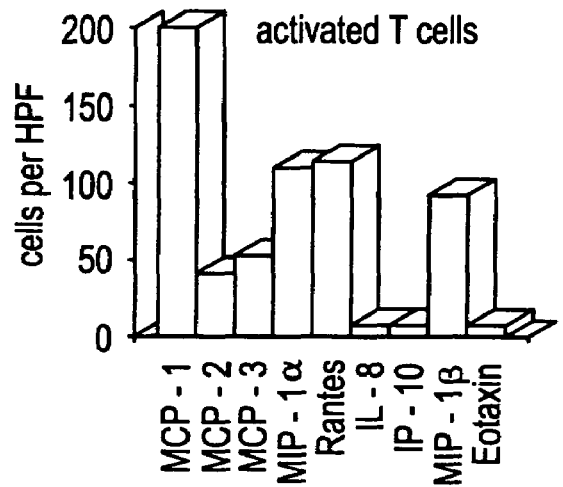
Figure 4B:
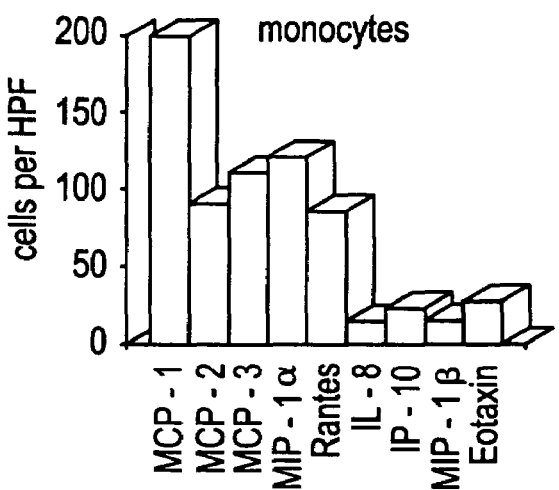
Figure 4D:
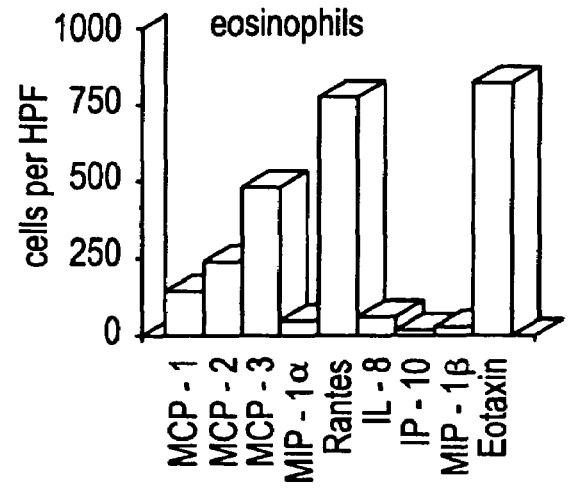

The clone #25 polypeptide was found to be a potent chemoattractant for human eosinophils, attracting eosinophils at levels approximately equal to or greater than that of the other eosinophilic chemoattractants, such as RANTES and MCP-3 (FIG. 4D).

Figure 5A:
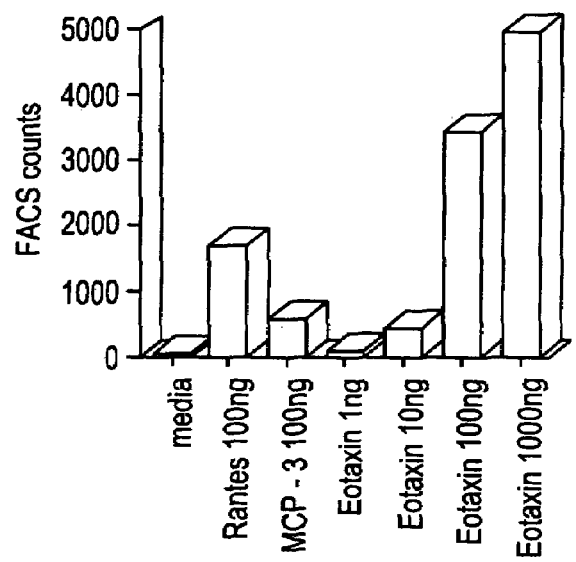
FIGS. 5A-5C are bar graphs illustrating the dose response of human eosinophils to human eotaxin. The chemotaxis of eosinophils in response to 1, 10, 100, or 1000 ng/ml of eotaxin (present in the bottom chamber) was assessed by FACS counting. The response to 100 ng of RANTES or of MCP-3 was also assessed. The results obtained with eosinophils from three different donors are shown (Donor #1, FIG. 5A; Donor #2, FIG. 5B; Donor #3, FIG. 5C).
Figure 5B:
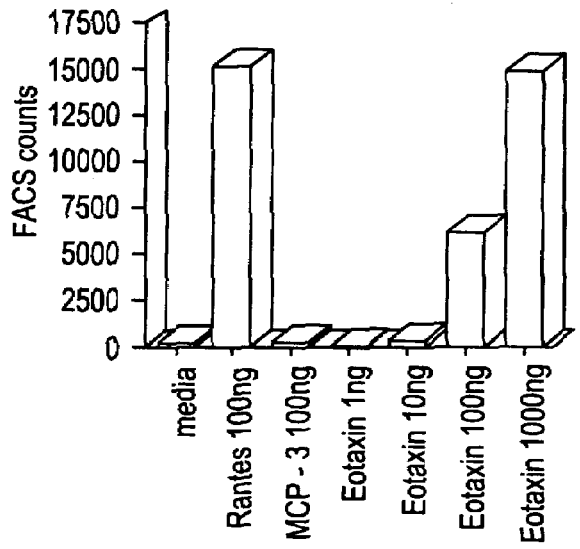
Figure 5C:
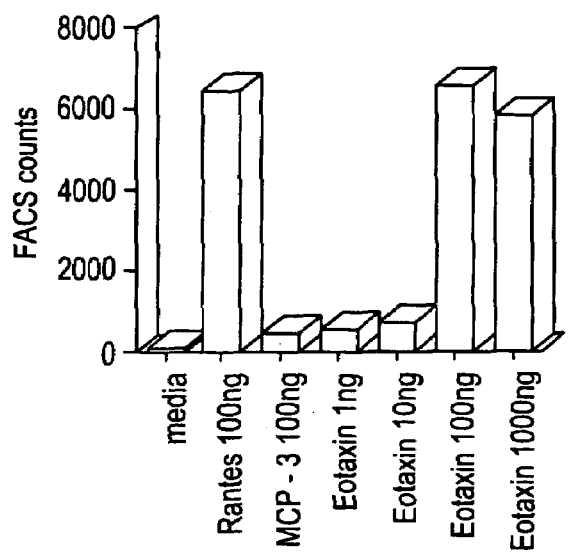

The dose response of human eosinophils to human eotaxin (synthetic mature) was also assessed in the transendothelial assay. Eosinophils were purified as described above. 1, 10, 100, or 1000 ng/ml of chemokine was present in the bottom chamber. Chemotaxis plates were incubated at 37° C. for 90 minutes, and the cells which migrated from the upper chamber to the bottom chamber were counted using a flow cytometer. The results obtained using eosinophils obtained from three different donors are shown in FIGS. 5A-5C. Donor to donor variation in the response of eosinophils to eotaxin, RANTES and MCP-3 was observed.

Human eotaxin was not chemotactic for human neutrophils, monocytes or activated T cells under the conditions used (FIGS. 4A-4C). Based upon the ability of the clone #25 polypeptide to induce the chemotaxis of eosinophils, and the lack of effect on other leukocytes cell types tested under the conditions of the assay, together with the sequence similarity of the encoded protein to guinea pig eotaxin, the polypeptide(s) encoded by genomic clone 25 and cDNA clone #25 were designated human eotaxin.

Example 5

Effects of Human Eotaxin on Human Eosinophils

A. Induction of Calcium Flux

Human eotaxin was tested for its ability to induce calcium flux in human eosinophils. Human eosinophils were isolated from peripheral blood by Percoll separation followed by CD16 magnetic bead treatment, as described above.

Cells were labeled with the fluorochrome Fluo-3 (Molecular Probes) according to the following protocol. 50 μg of Fluo-3 was dissolved in 44 μl of DMSO and diluted to 10 μM with modified Gay's buffer (MGB)(5 mM KCl, 147 mM NaCl, 0.22 mM $KH_2PO_4$, 1.1 mM $Na_2HPO_4$, 5.5 mM glucose, 0.3 mM $MgSO_4.7H_2O$, 1 M $MgCl_2$, and 10 mM HEPES, pH 7.4). Cells were resuspended in MGB to $10^7$ cells/ml, and incubated with an equal volume of 10 μM Fluo-3 mix for 30 minutes at room temperature. Cells were then washed twice with MGB and resuspended at $2 \times 10^6$ cells/ml in MGB. The calcium flux to various chemokines was measured on the FACScan, by analyzing fluorescence intensity (linear scale) versus time.

Figure 6A:
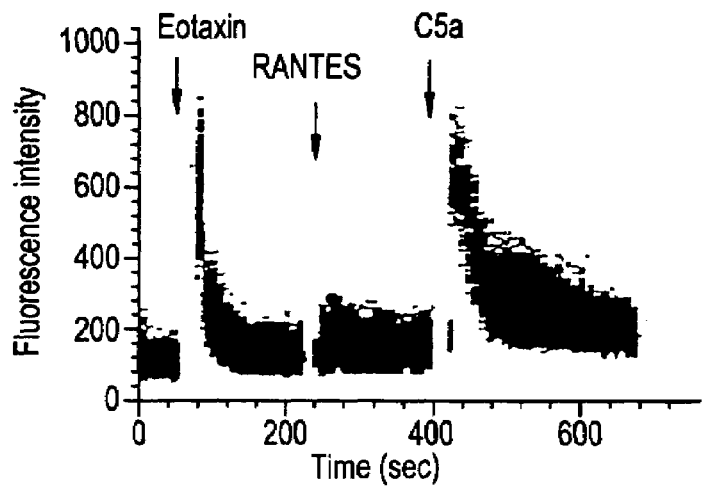
FIGS. 6A-6E are plots of fluorescence intensity over time, illustrating the calcium flux of human eosinophils in response to various agents administered in sequence (arrows indicate time of administration). Eosinophil response to a synthetic human eotaxin (eotaxin), followed by RANTES, and then anaphylatoxin C5a is illustrated in FIG. 6A. Eosinophil response to RANTES, followed by eotaxin, followed by anaphylatoxin C5a is illustrated in FIG. 6B. Eosinophil response to MIP-1α, followed by eotaxin, followed by anaphylatoxin C5a is illustrated in FIG. 6C. Eosinophil response to RANTES, followed by repeat exposure to RANTES is shown in FIG. 6D. Eosinophil response to human eotaxin followed by repeat exposure to human eotaxin polypeptide is shown if FIG. 6E. All chemokines, as well as C5a, were used at a final concentration of 100 nM.

FIG. 6A shows that 100 nM of human eotaxin was able to induce a strong calcium flux in human eosinophils. The magnitude of the response was greater than that obtained with all other chemokines tested, including RANTES, MCP-3, MCP-2, MIP-1α, and IL-8. This response was rapid and transient.

B. Desensitization

Chemokine-mediated calcium flux desensitizes individual receptors to further stimulation with other specific ligands. This technique has been used to establish the specificity of a chemokine for a given receptor, and the combinations of different ligands that bind to the one receptor (Uguccioni, M. et al., "Actions of the chemotactic cytokines MCP-1, MCP-2, MCP-3, RANTES, MIP-1 alpha and MIP-1 beta on human monocytes," Eur. J. Immunol., 25: 64-68 (1995)). Desensitization was also assessed using the calcium flux assay.

Figure 6B:
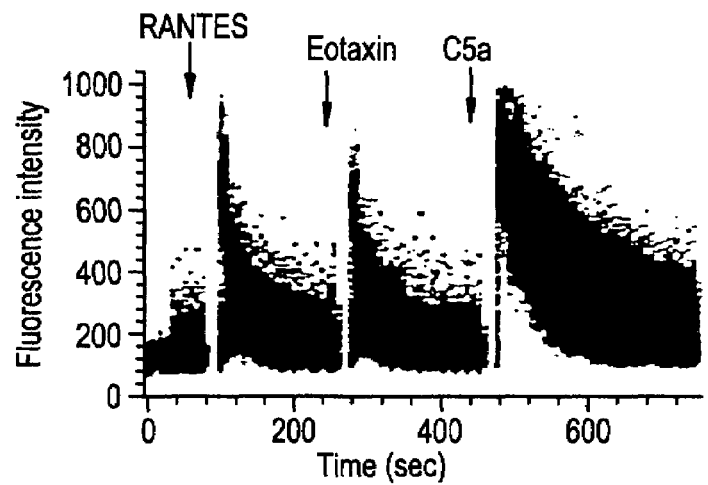
Figure 6C:
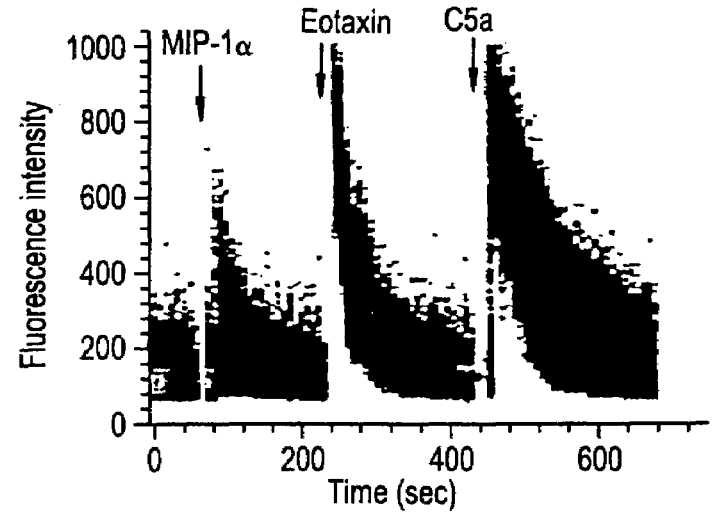
Figure 6D:
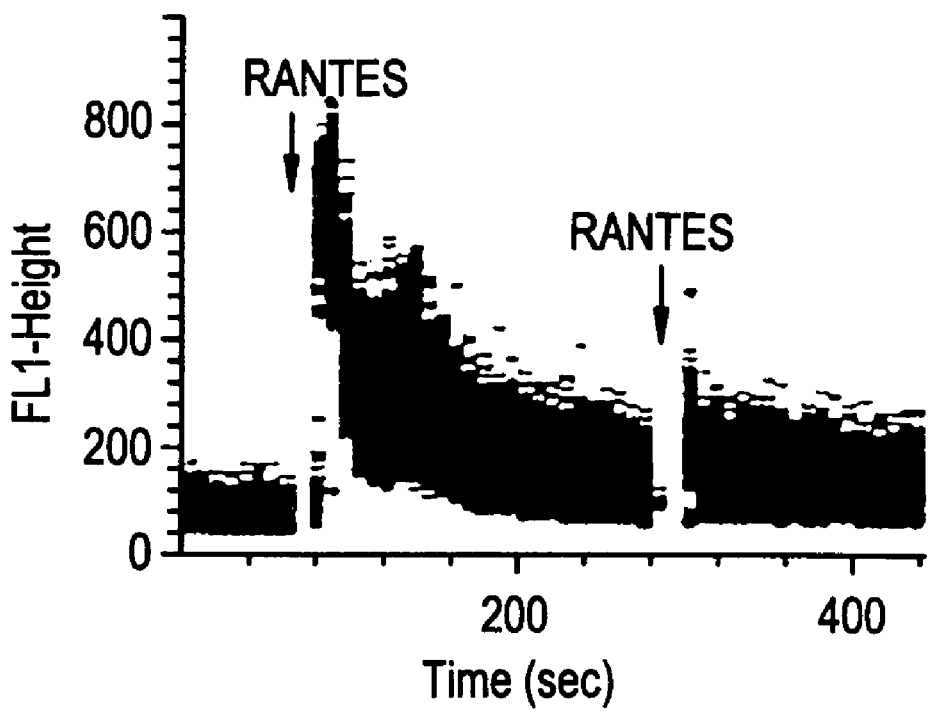
Figure 6E:
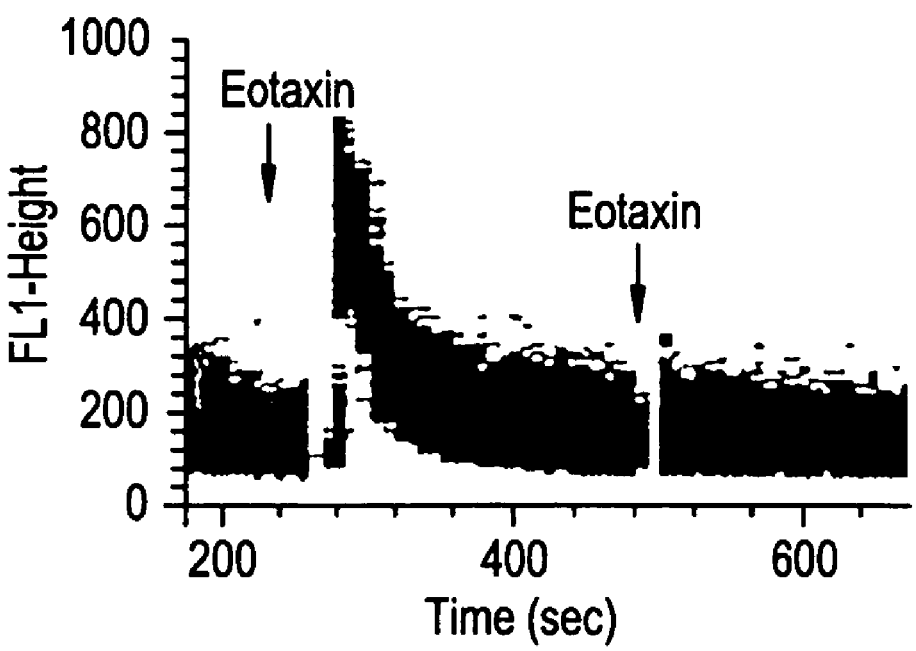

Human eotaxin polypeptide was able to desensitize eosinophils to subsequent stimulation with eotaxin (FIG. 6E) or RANTES (FIG. 6A). However, prior stimulation of eosinophils with RANTES (FIG. 6B) or MIP-1α (FIG. 6C) was unable to completely desensitize the response to subsequent stimulation with eotaxin. This may be because human eotaxin is binding to receptor(s) that cannot be bound/desensitized by any of the chemokines tested, or because human eotaxin induces such a strong response that weaker agonists are unable to desensitize the eotaxin receptor on eosinophils. Nevertheless, RANTES was able to reduce the magnitude of the subsequent eotaxin response, indicating partial desensitization.

Example 6

Competitive Binding Studies

The results of chemotaxis assays indicated that purified eosinophils and to a lesser extent, butyric acid differentiated HL-60 cells, responded to human eotaxin, while other cell types tested did not. In order to further assess the relationship between human eotaxin and other chemokines known to be active on these cells, competitive ligand binding assays were performed.

HL-60 Cell Differentiation

HL-60 cells can differentiate down an eosinophilic pathway (Tagari, P. et al., *Int. Arch. Allergy Immunol.*, 101: 227-233 (1993); Van Riper, G. et al., *J. Immunol.*, 152:. 4055-4061 (1994)). HL-60 cells (American Type Culture Collection, Accession No. CCL 240) were resuspended in RPMI (without HEPES) +20% fetal calf serum (FCS) at $0.5 \times 10^6$ cells/ml. n-Butyric acid (Sigma Chemical Co., St. Louis, Mo.; #B5887) was added to a final concentration of 0.4 mM from a stock solution of 1 M n-butyric acid. HL-60 cells were incubated at 37° C., 5% $CO_2$ for four days before harvesting.

Radioiodination of Human Eotaxin

Synthetic eotaxin (predicted mature protein consisting of amino acids 24-97) was labeled with 125I using Bolton-Hunter reagent according to the manufacturer's instructions (Du Pont NEN, Mass.). Unbound iodine was separated by gel filtration and radiolabeled eotaxin was aliquoted and stored at −80° C. until use. The specific activity of the labeled eotaxin was $4.1 \times 10^4$ cpm/pmol.

Ligand Binding Assay $^{125}$I-labeled human eotaxin was prepared as described above. $^{125}$I-labeled RANTES, $^{125}$I-labeled MCP-3, and $^{125}$I-labeled MIP-α were purchased from DuPont NEN, Mass. Binding of RANTES, MIP-1α and human eotaxin was carried out in binding buffer consisting of 50 mM HEPES supplemented with 1 mM $CaCl_2$, 5 mM $MgCl_2$ and 0.5% BSA. Aliquots of 50 µl ($5 \times 10^5$) cells were added to Eppendorf tubes, incubated first with unlabeled chemokines, then 0.1 nM $^{125}$I labeled chemokines as indicated below. The final reaction volume was 200 µls. Total binding was carried out in the absence of unlabeled chemokines, and non-specific binding was determined by incubating cells with radiolabeled chemokine in the presence of 250 nM of cold chemokine. At the end of incubation, cells were washed 3 times in binding buffer plus 0.5 M NaCl. The cell pellets were transferred into LP3 tubes and counted in a gamma counter.

The binding of MCP-3 was carried out in Hank's Balanced Salt Solution (HBSS) supplemented with 0.5% BSA and 0.1% sodium azide. After a 30 minute incubation at 37° C., the cells were laid onto 800 µl of 20% sucrose and spun at 3000 rpm to separate unbound isotope. The tubes were snap-frozen on dry-ice/ethanol and the tips of the tubes containing the cell pellets were cut off and counted. All experiments were carried out using duplicates and repeated at least three times. Scatchard analysis was performed with Microsoft Excel using a linear curve fit.

Competitive Binding Studies

Figure 7:
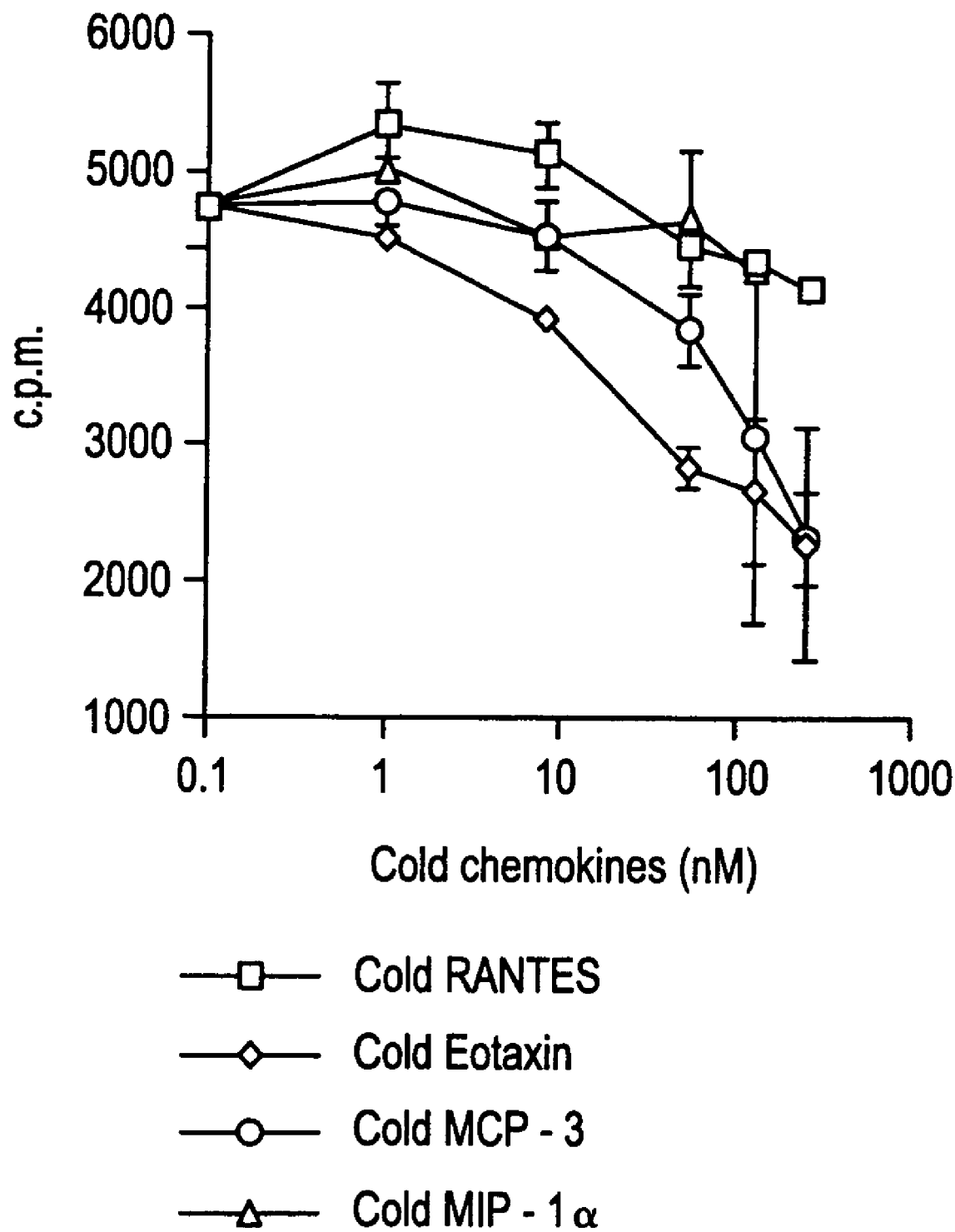
FIG. 7 is a graph illustrating the binding of synthetic human eotaxin to eosinophils. $^{125}$I-labeled eotaxin was incubated with purified eosinophils in the presence of increasing concentrations of eotaxin (◇), RANTES (□), MIP-1α (Δ), and MCP-3 (○).
Figure 8:
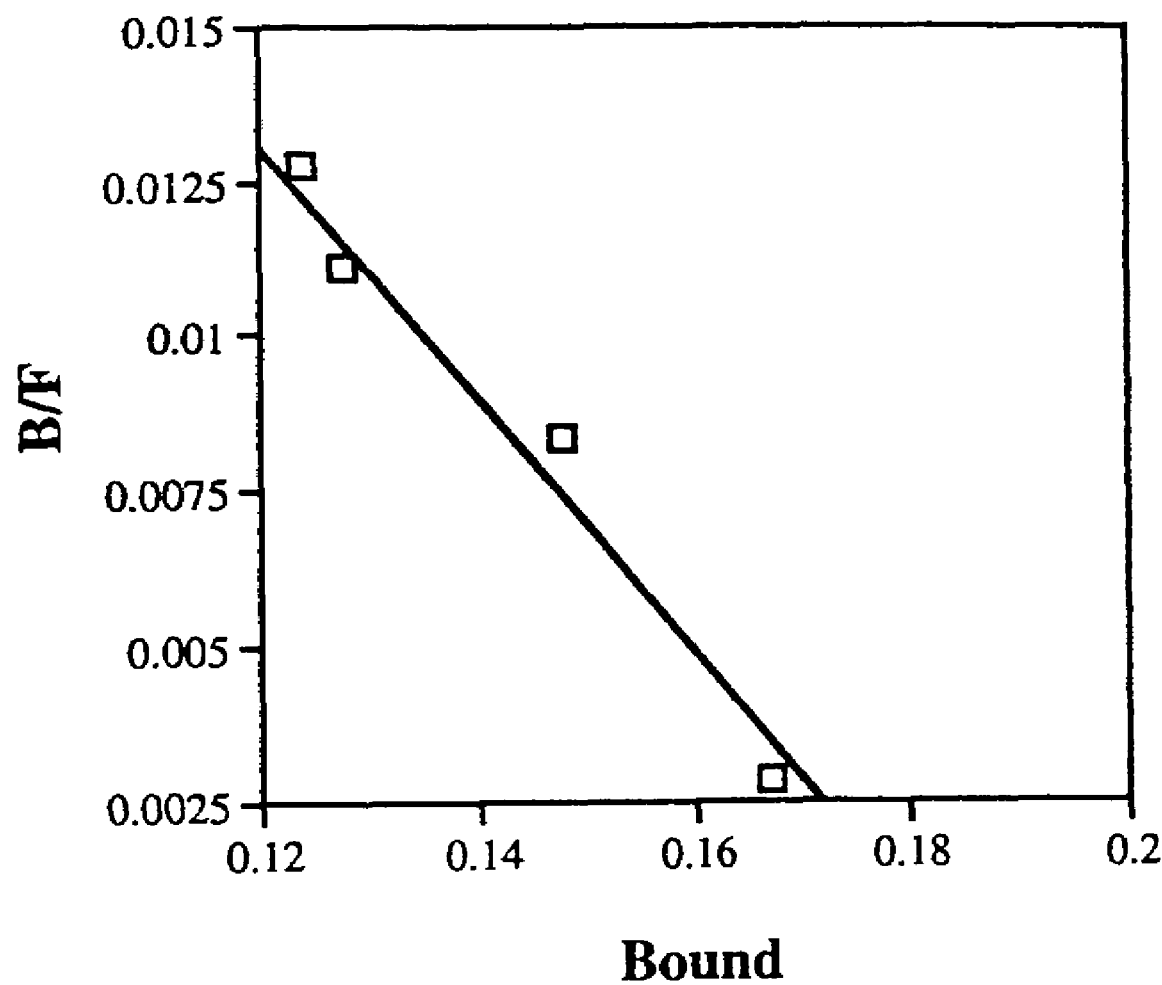
FIG. 8 is a Scatchard plot calculated from the data presented in FIG. 7, which indicates a Kd of 4.7 nM and $2.3 \times 10^4$ binding sites per cell.

Human eosinophils were purified as described in Example 4, and the binding of human eotaxin to eosinophils was investigated. $^{125}$I-labeled eotaxin was incubated with purified eosinophils in the presence of increasing concentrations of 'cold' eotaxin, 'cold' RANTES, 'cold' MIP-1α or 'cold' MCP-3. FIG. 7 shows that radiolabeled eotaxin was able to bind to human eosinophils, could be inhibited efficiently by 'cold' eotaxin, and less efficiently by MCP-3. RANTES and MIP-1α were not able to compete with eotaxin under the conditions used. Data from competitive binding by unlabeled eotaxin was used to produce a Scatchard plot (FIG. 8), which revealed a single class of high affinity binding sites for eotaxin, a Kd of 4.7 nM, and $2.4 \times 10^4$ binding sites per cell. The observed dissociation constant is analogous to other chemokine-receptor dissociation constants.

Figure 9A:
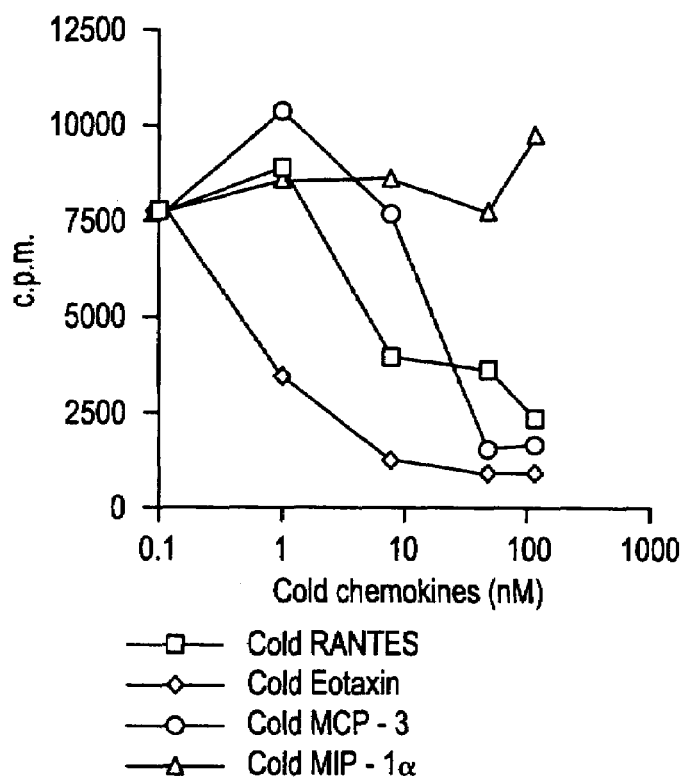
FIGS. 9A-9B are graphs illustrating the competitive binding of human eotaxin with RANTES or MCP-3. Purified human eosinophils were incubated with radiolabeled RANTES (FIG. 9A) and increasing concentrations of 'cold' RANTES (□), 'cold' eotaxin (◇), cold MCP-3 (○) or 'cold' MIP-1α (Δ). Purified human eosinophils were also incubated with radiolabeled MCP-3 (FIG. 9B) and increasing concentrations of 'cold' MCP-3 (◆) or 'cold' eotaxin (■).

In another experiment, purified human eosinophils were incubated with increasing concentrations of 'cold' RANTES, 'cold' eotaxin, 'cold' MCP-3 or 'cold' MIP-1α. 0.1 nM radiolabeled RANTES was added, and binding was carried out at room temperature for 60 minutes. The results of this experiment indicated that eotaxin could completely inhibit $^{125}$I-RANTES binding to eosinophils (FIG. 9A).

Figure 9B:
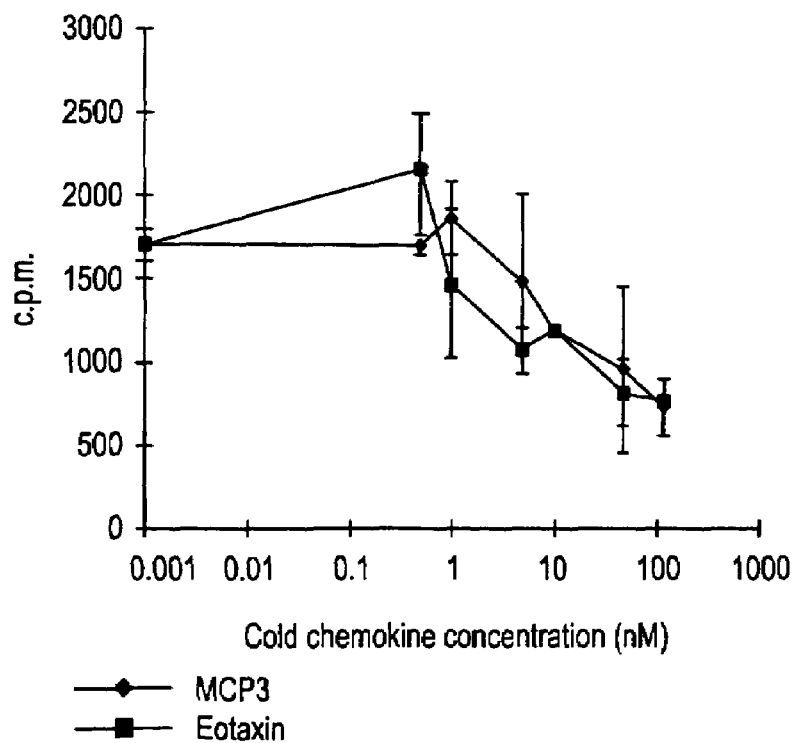

The competitive binding of MCP-3 and eotaxin was also assessed. Purified human eosinophils were incubated with increasing concentrations of (a) 'cold' MCP-3 or 'cold' eotaxin, and (b) radiolabeled MCP-3. MCP-3 binding to eosinophils was completely blocked by eotaxin with a similar affinity as MCP-3 (FIG. 9B).

Figure 10:
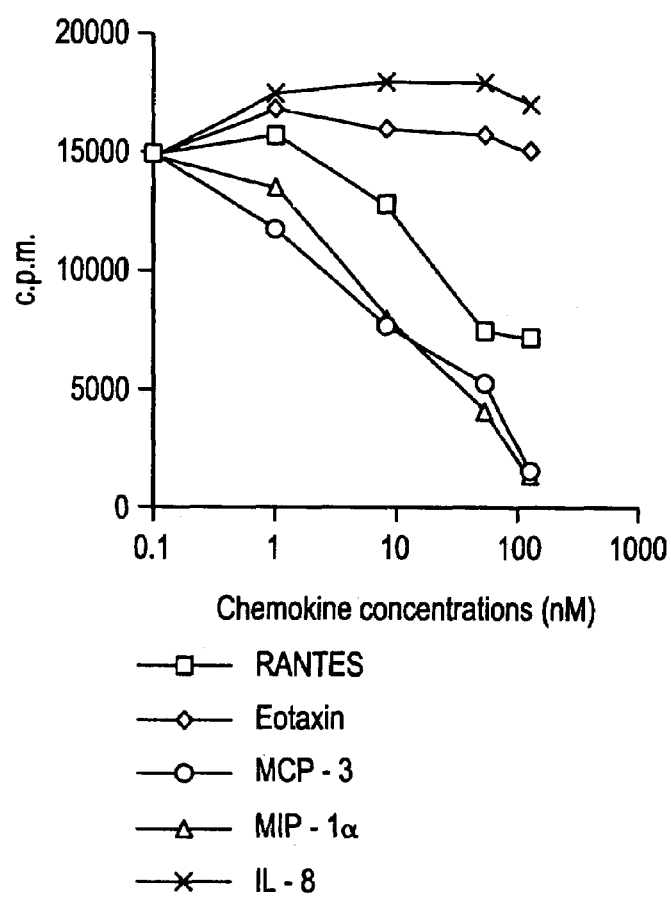
FIG. 10 is a graph illustrating that human eotaxin does not inhibit MIP-1α binding. Butyric acid differentiated HL-60 cells were incubated with (a) 'cold' MIP-1α (Δ), eotaxin (◇), RANTES (□), MCP-3 (602) or IL-8 (×); and (b) 0.1 nM radiolabeled MIP-1α, and binding took place.

To assess MIP-1α binding, butyric acid differentiated HL-60 cells were incubated with 'cold' MIP-1α, 'cold' eotaxin, 'cold' RANTES, 'cold' MCP-3 or 'cold' IL-8. 0.1 nM radiolabeled MIP-1α was then added, and the binding assay was carried out as described above. Total binding was measured in the absence of any competitors. MIP-1α, which hardly bound to eosinophils, showed good binding to HL-60 cells and this binding was not significantly affected by up to 1,000 fold excess of eotaxin under the conditions used (FIG. 10). These data indicate that a MIP-1α/RANTES receptor (probably CC CKR-1 (Neote et al., *Cell*, 72: 415-25 (1993)) is expressed on HL-60 cells, but is not detectably expressed on eosinophils, and that eotaxin binds to a receptor that is distinct from this receptor. RANTES and MCP-3 may share the receptor (designated the CKR-3 receptor; see below) with eotaxin but bind with a lower affinity.

Example 7

Eotaxin Binds to and Mediates Chemotaxis Through a Novel CC Chemokine Receptor

Two CC chemokine receptors have been described in the literature to date: (1) the MIP-1α/RANTES receptor (Neote, K. et al., *Cell*, 72: 415-25 (1993); Horuk, R. et al., WO 94/11504, published May 26, 1994; Gao, J.-I. et al., *J. Exp. Med.*, 177: 1421-1427 (1993)), and (2) the MCP-1 receptor (Charo, I.F. et al., *Proc. Natl. Acad. Sci. USA*, 91: 2752 (1994)). The MIP-1α/RANTES receptor binds RANTES in addition to MIP-1α, and the MCP-1 receptor has been implicated in both MCP-1 and MCP-3 binding. In addition, a novel C-C chemokine receptor designated C-C chemokine receptor 3 (CKR-3; also referred to as EosL2 receptor) has been identified (U.S. Ser. No. 08/375,199, entitled "Novel G Protein-Coupled Receptor Gene and Methods of Use Therefor", filed Jan. 19, 1995, the teachings of which are incorporated herein by reference in their entirety.) The ability of various chemokine receptors to mediate eotaxin binding and/or a functional effect (chemotaxis) in response to eotaxin was determined.

CKR-3 Gene

Eosinophil isolation and purification was performed as described in Example 4. mRNA for RT-PCR (Reverse transcription-polymerase chain reaction) was extracted directly from purified cells using the Micro-FastTrack™ mRNA isolation kit purchased from Invitrogen. 20-50 ng of mRNA was reverse transcribed using a GeneAmp® RNA PCR kit (Perkin-Elmer) with oligo dT and/or random hexamers as primers in a 20 µl final volume as specified by the manufacturer. 2-5 µl of this cDNA (reverse transcribed eosinophil message) was mixed with 200 µM dNTPs and 50-100 pmol of degenerate primers in a 50 µl volume.

PCR products were assessed and separated by agarose gel electrophoresis, and appropriately sized fragments were purified and subcloned using the pCR-Script™ SK+ cloning kit (Stratagene). By sequence analysis of PCR fragments, generated from degenerate oligos, a 201 bp partial cDNA clone in pCR-Script was identified. The 201 bp PCR fragment was obtained from amplification using primer 2a-2 (forward (SEQ ID NO:9); 5'-AC CTG GCC ITG GCI GAC CTM CTC TT) and primer 3R (reverse (SEQ ID NO:10); CTG GCR ATG GAC CGG TAI CAG GTR CGG -5'). This partial clone, designated Eos L2 (also referred to as L2 and EL2), was used for genomic library screening.

A human genomic phage library constructed in the EMBL3 SP6/T7 vector, purchased from CLONTECH Laboratories, Inc. (Palo Alto, Calif.), was screened with the 201 bp PCR fragment to obtain a full-length clone. To prepare the PCR probe, the 201 bp fragment was released from the pCR-Script vector with restriction enzymes EcoRI and Not I. This digestion resulted in a fragment of 240 bp comprised of the 201 bp fragment plus 39 base pairs of polylinker from the vector. The fragment was separated from vector by electrophoresis through agarose gel, and purified by Magic Mini Prep (Promega Corp. Madison, Wis.) as recommended by the manufacturer. Approximately 200 ng of material was labeled with the Random Primed DNA Labeling Kit purchased from Boehringer Mannheim following the manufacturer's recommended labeling protocol.

Approximately 25,000 plaque forming units were mixed with 600 µl of an overnight bacterial culture of *E. coli* strain K802 provided with the library in NZCYM top agarose and plated on 150 mm petri dishes containing NZCYM agar (NZYCM broth, Agar and Agarose were purchased from Gibco/BRL). After incubation at 37° C. for 7 hours, the plates were overlaid with BA-85 nitrocellulose membranes (Schleicher and Schuell, Keene, N.H.) for 5 minutes to allow transfer of phage to membrane. The membranes were then soaked for 5 minutes in Denaturing Solution (1.5 M sodium chloride, 0.5 N sodium hydroxide) followed by neutralization in 1.5 M sodium chloride, 0.5 M Tris, pH 8.0. The filters were allowed to air dry for 15 minutes and then baked for two hours at 80° C. under vacuum. For Southern blots, hybridization was in 6×SSC (1×SSC is 0.15 M sodium chloride, 0.015 M sodium citrate) containing 5× Denhardt's solution (1× Denhardt's solution is 0.02% bovine serum albumin, 0.02% ficoll, 0.02% polyvinyl-pyrolidone), 10% w/v dextran sulfate, 2% SDS, and sheared salmon sperm DNA (100 µg/ml) overnight at 65° C. The membrane was rinsed twice in 2×SSC, 0.5% SDS at 65° C. followed by two washes (15 min each) in 0.2×SSC, 0.5% SDS at 65° C.

One genomic phage clone, designated Eos L2.8, contained an insert which comprises the 1.8 kb Hind III fragment seen on Southern blots (complete insert size was not determined, but is ~17 kb). Phage clone Eos L2.8 was digested with Hind III restriction enzyme and electrophoresed on an agarose gel. A Hind III fragment of approximately 1.8 kb was cut out, electroeluted from agarose, phenol/chloroform extracted and precipitated with ethanol. The 1.8 kb fragment was resuspended in water and ligated into the Hind III site of the pBluescript II KS+ vector (Stratagene) followed by transformation into DH5α competent cells purchased from Gibco/BRL.

Both strands of this Hind III fragment were sequenced, and the fragment was found to contain the entire amino acid coding region for a human CKR-3 receptor (Eos L2 receptor). The sequence is presented in FIGS. 15A-15D (SEQ ID NO:5 and SEQ ID NO:6).

FLAG-tagged CKR-3 (Eos L2) Receptor Construct

A CKR-3 receptor fusion protein was constructed as follows:

1. A FLAG-PAF receptor construct in pCDM8 (constructed as reported in D. Kunz, N. P. Gerard, and C. Gerard (1992), *J. Biol. Chem.* 267: 9101-9106) was double digested with Hind III and EcoRI to release a fragment containing nucleotides which encode the FLAG peptide. The nucleotide sequence is AAGCT-TCCA GCA GCC ATG GAC TAC AAG GAC GAC GAT GAC AAA GAATTC (SEQ ID NO:11). The amino acid sequence is MDYKDDDDKEF (SEQ ID NO:12). The Hind III/EcoRI fragment containing the FLAG nucleotides was subcloned into the Hind III/EcoRI sites of the pcDNA3 vector (Invitrogen, San Diego, Calif.) giving rise to pcDNA3/FLAG.

2. The pBluescript II KS+ vector containing the 1.8 kb CKR-3 Hind III fragment was digested with BamHI and Xho I to release a 1.261 kb fragment. This BamHI-XhoI fragment contains nucleotides encoding CKR-3 amino acids 91 through the stop codon plus the same 3' untranslated region and 21 bp of pBluescript II KS+vector.

3. Two PCR primers were generated to amplify the 5' end of the CKR-3 gene, but removing the first Met and engineering in an EcoRI site which will be compatible with the EcoRI site described above in step 1. The 5' primer (SEQ ID NO:13) was:

```
       EcoRI
5'-TTAA GAATTC ACA ACC TCA CTA GAT AC
```

This primer contains an EcoRI site and the first 17 nucleotides of the CKR-3 gene except for the Met codon.

The 3' primer (SEQ ID NO:14) was:

```
        BamHI
5'-CATAGT GGATCC AGAATG
```

This primer primes in the CKR-3 gene just 3' to the BamHI site. Amplification with these two primers using the pBluescript II KS+ vector containing the 1.8 kb CKR-3 fragment as template will amplify a 280 bp fragment containing the 5' end of the CKR-3 gene which can be digested with EcoRI and BamHI to give a fragment for ligation as described below.

Conditions for amplification were: 100 ng of pBluescript II KS+ containing the 1.8kb CKR-3 fragment was combined with 200 µM dNTPs and 50 pmol of primers in a 50 µl reaction volume. The final magnesium concentration was 2.5 µM and the pH was 8.0. The fragment was amplified with 25 cycles of 94° C., 30 sec; 55° C., 30 sec; 72° C., 30 sec. The amplified product was separated on agarose gel and purified by electroelution as described above. The fragment was digested with EcoRI and BamHI purified again on agarose gel.

4. For construction of the Flag-tagged CKR-3 gene, the pcDNA3 vector containing the FLAG fragment (described in step 1) was digested with EcoRI and Xho I. The vector fragment (an EcoRI-XhoI fragment comprising the FLAG coding sequence) was separated from the polylinker fragment by electrophoresis, and the vector fragment was purified as described for other electroeluted fragments. The vector fragment was combined with the EcoRI-BamHI fragment generated by PCR in step three. These two fragments were combined with the 1.261 kb BamHI-XhoI fragment from step two. All three fragments were triple ligated together to yield the FLAG-tagged CKR-3 receptor in pcDNA3. Ligated DNA was transformed into DH5α.

L1-2 Transfectants

The mouse L1-2 cell line is derived from a pre-B lymphoma, and was obtained from Dr. Eugene Butcher (Stanford University, Stanford, Calif.). L1-2 transfectants expressing IL-8 A receptor (a C-X-C chemokine receptor), IL-8 B receptor (a C-X-C chemokine receptor), or the MIP-1α/RANTES receptor (also referred to as C-C chemokine receptor 1) were obtained from Dr. Eugene Butcher (Murphy P. M. and H. L. Tiffany, Science, 253: 1280-1283 (1991); Murphy et al., WO 93/06299; Holmes, W. E. et al., Science, 253: 1278-1280 (1991); Neote, K. et al., Cell, 72: 415-425 (1993); Horuk, R. et al., WO 94/11504, published May 26, 1994; Gao, J.-I. et al., J. Exp. Med., 177: 1421-1427 (1993)).

L1-2 cells were also transfected with a linearized clone encoding C-C chemokine receptor 3 (CKR-3)), or a clone encoding MCP-1 receptor type B (Charo, I. F. et al., Proc. Natl. Acad. Sci. USA, 91: 2752 (1994)). The receptors encoded by the latter clones are tagged with a FLAG epitope at the N-terminus which is encoded by the pcDNA expression vector (Invitrogen, San Diego, Calif.).

The transfection conditions were as follows: 25 million L1-2 cells in 1.0 ml of transfection buffer (Hank's Balanced Salts Solution plus 20 mM Hepes, pH 7.05, 137 mM NaCl, 5 mM KC1, 0.7 mM $Na_2HPO_4$, and 6 mM dextrose) were incubated for 10 minutes at room temperature with 20 µg of linearized DNA. The cell/DNA mixture was transferred to an electroporation cuvette (available from BioRad, Richmond, Calif.) and subjected to electroporation using a Bio-Rad electroporator set to 250 volts, 960 µF. The electroporated cells were allowed to stand at room temperature for 10 minutes followed by transfer to 10 mls of media. The cells were incubated for 48 hrs followed by the addition of media bringing the volume to 50 mls. 0.8 mg/ml of Geneticin (Gibco/BRL) was added to the cells which were then plated over five 96-well microtiter plates. After about 2 weeks under selection, the wells were screened individually by immunofluorescence and flow cytometry using an antibody reactive with the FLAG epitope (M1 monoclonal antibody; Kodak). Stable transfectants expressing receptor on the surface were screened for eotaxin binding and chemotactic activity in vitro.

CKR-3-transfected Cells Bind to Human Eotaxin

Figure 11:
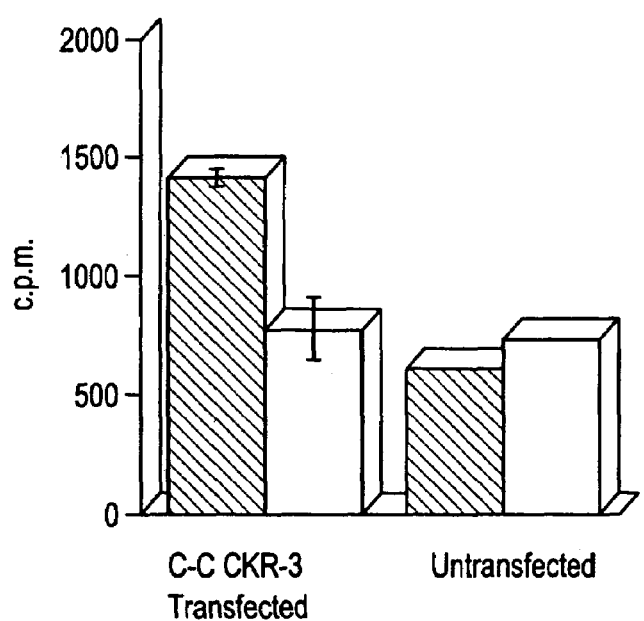
FIG. 11 is a bar graph illustrating the binding of human eotaxin to CKR-3 transfected L12 cells. Radiolabeled eotaxin was incubated with $5 \times 10^5$ transfected cells or untransfected L1-2 cells. Hatched bar, without competitor; white bar, with 125 nM unlabeled eotaxin.

Binding buffer consisted of 50 mM HEPES supplemented with 1 mM $CaCl_2$, 5 mM $MgCl_2$ and 0.5% BSA. $^{125}I$-labeled eotaxin (10 nM) was incubated with $5 \times 10^5$ CKR-3-transfected cells or with untransfected L1-2 cells in 200 µl of binding buffer, and binding was carried out at room temperature for 60 minutes. Binding was determined in the presence of 125 nM unlabeled eotaxin or in the absence of competitor. FIG. 11 shows that significant binding of eotaxin was achieved under these conditions, under which eosinophils also efficiently bind eotaxin. Binding to CKR-3 transfectants was specific, since it could be inhibited by unlabeled eotaxin and untransfected L1-2 cells failed to bind.

Protocol for Transfectant Chemotaxis

For assessing chemotaxis of transfectants, the transendothelial assay described in Example 4 was modified as follows. 600 µl of assay media (50% RPMI1640, 50% M199, 0.5% endotoxin free BSA) containing the chemokine to be tested was added to the bottom chamber of the assay plate (Collaborative Biomedical, Cat. No. 40575). $10^6$ L1-2 transfectants or L1-2 wild type cells were added to the upper chamber in a 100 µl volume. The cells were incubated for 4 hr-overnight at 37° C. The upper chamber was removed and cells which migrated through the membrane insert of the upper chamber were counted.

Figure 12A:
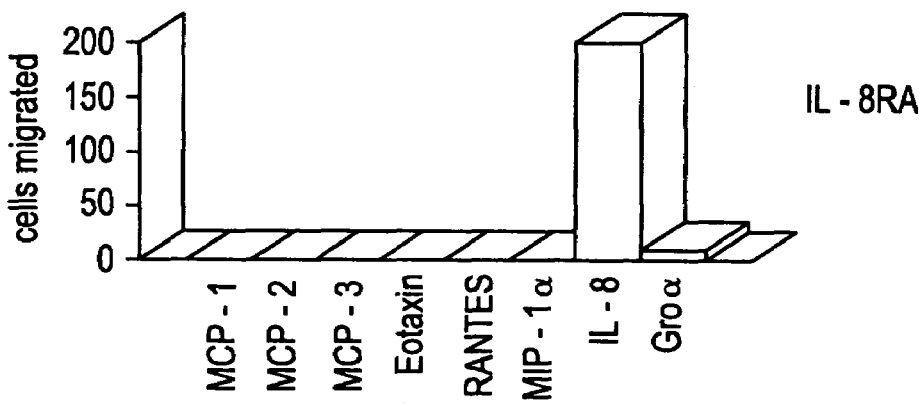
FIGS. 12A-12E are histograms illustrating the chemotaxis of L1-2 transfectants in response to different chemokines (MCP-1, MCP-2, MCP-3, eotaxin, RANTES, MIP-1α, IL-8 and Groα). The L1-2 pre-B lymphoma cell line was transfected with DNA encoding IL-8 RA, IL-8 RB, MIP-1α/RANTES receptor (CC CKR-1), MCP-1 receptor (CC CKR-2) or CC-CKR-3, and the effect of various chemokines, including human eotaxin, on the different transfectants was assessed. Cell counting was performed using a microscope.
Figure 12B:
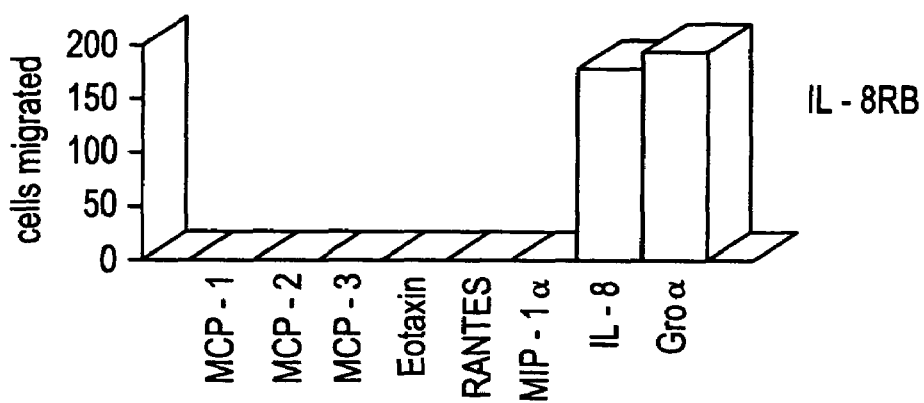
Figure 12C:
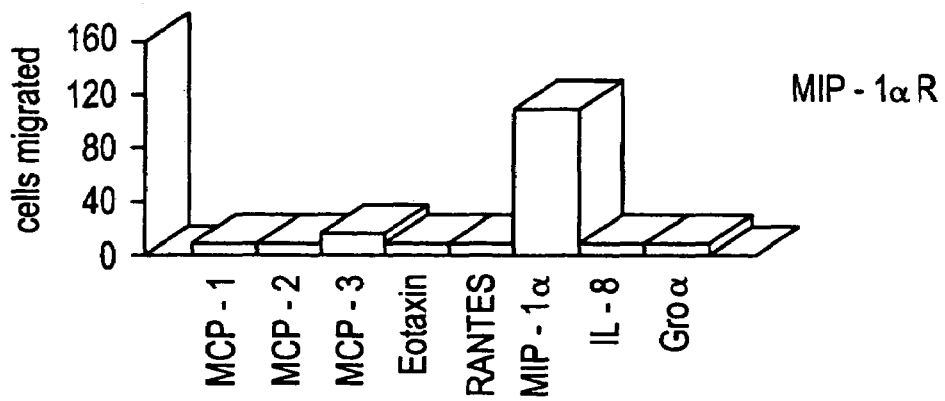
Figure 12D:
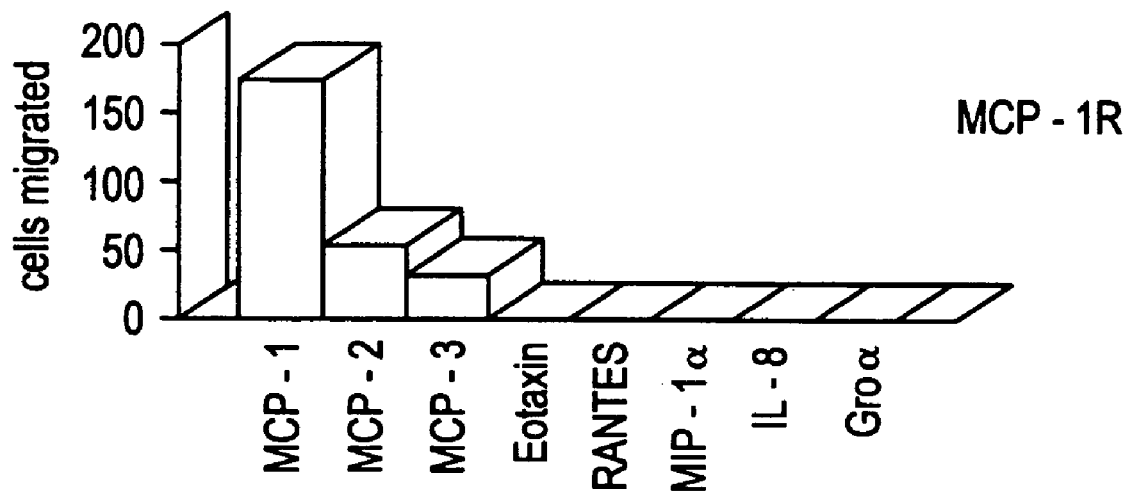

Chemotaxis of a pre-B Lymphoma Line Transfectants Expressing Chemokine Receptors Untransfected L1-2 cells do not respond to any human chemokines, including IL-8, MCP-1, RANTES, MIP-1α and eotaxin. However, when transfected with DNA encoding the IL-8RA, IL-8RB, MIP-1α/RANTES, or MCP-1 receptor, L1-2 cells were able to chemotax in response to specific ligands (FIGS. 12A-12D). FIG. 12C shows that L1-2 cell transfectants expressing the human MIP1-α/RANTES receptor chemotaxed strongly to MIP-1α, and weakly to MCP-3. In contrast, these cells were not responsive to human eotaxin over a wide dose range (1 ng/ml to 1000 ng/ml) (FIG. 12C illustrates the effect of 100 ng eotaxin). Likewise, L1-2 cells transfected with DNA encoding the human MCP-1 receptor (B type) chemotaxed strongly in response to MCP-1 and weakly in response to MCP-3, but not other ligands including eotaxin. These studies indicated that these receptors are not functioning in eotaxin chemotaxis, or at least are unable to when introduced by transfection into L1-2 cells under the conditions used here. The presence of these receptors in monocytes and activated T cells, which are unresponsive to eotaxin, further indicates that eotaxin does not bind to or function through either of these receptors.

Figure 12E:
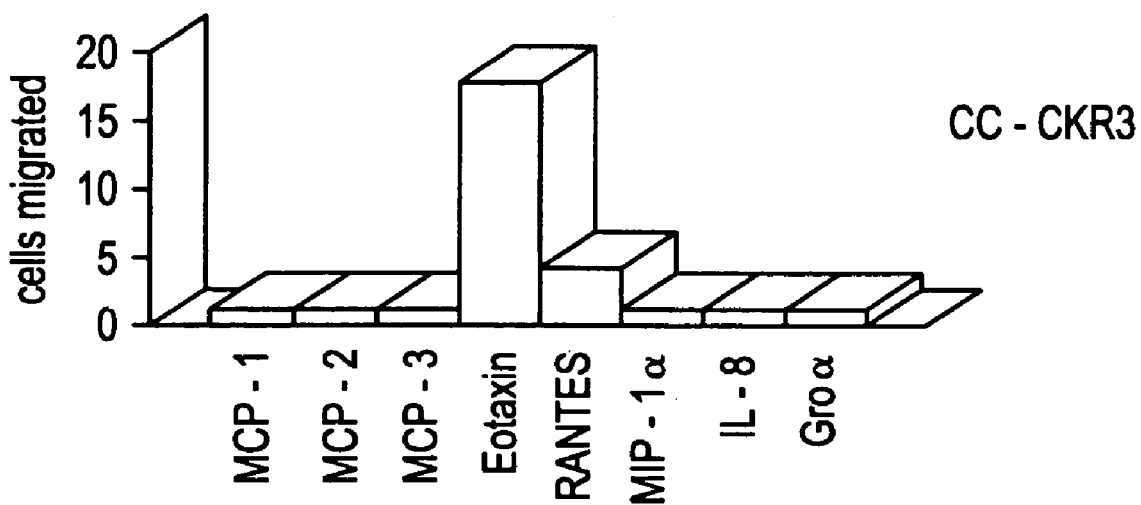

FIG. 12E shows the response of L1-2 cells transfected with a C-C CKR-3 clone encoding a novel C-C chemokine receptor identified from human eosinophils (U.S. Ser. No. 08/375,199, filed Jan. 19, 1995). These cells chemotaxed strongly in response to eotaxin, and less so in response to RANTES. In contrast, L1-2 transfectants expressing CKR-3 did not respond to the other chemokines tested under the conditions of the assay. These results indicate that eotaxin is a principal ligand for the CKR-3 receptor. Furthermore, these results support the conclusion that C-C CKR-3 and human eotaxin are an important receptor-ligand pair for eosinophil chemotaxis.

A monoclonal antibody (LS26-5H12) reactive with CKR-3 was used in FACS analysis of human eosinophils, peripheral blood lymphocytes, monocytes, neutrophils, and activated T cells (Example 4). Cells were stained with monoclonal antibody LS26-5H12, followed by FITC-antimouse Ig (Jackson ImmunoResearch Laboratories, Inc.). Fc receptor binding was controlled for by using an excess of normal human serum.

All eosinophils were stained with anti-CKR-3 antibody LS26-5H12 (not shown). Monocytes were weakly positive for immunofluorescence. A small proportion of lymphocytes were positive for staining, and substantially all of the activated T cells were weakly stained with the antibody LS26-5H12, indicating that T cells express receptor which is upregulated upon T cell activation. Neutrophils were not significantly stained by LS26-5H12 antibody under the conditions of the assay.

As indicated above, on eosinophils there is a single class of binding sites for eotaxin, with a Kd of 4.7 nM, and $2.4 \times 10^4$ binding sites per cell. The competition studies described herein indicate that eotaxin binds to a receptor which is distinct from the MIP-1α/RANTES receptor described by Neote et al. (*Cell*, 72: 415-25 (1993)). As indicated by studies with transfectants expressing CKR-3 protein, CKR-3 can mediate eotaxin binding and chemotaxis in response to eotaxin. In addition, antibody LS26-5H12 detects CKR-3 on eosinophils. Taken together, the data support the conclusion that CKR-3 on eosinophils accounts for some, if not all, of the eotaxin binding and responsiveness of eosinophils.

Example 8

Monoclonal Antibodies (MAbs) Reactive with Human Eotaxin

MAbs reactive with human eotaxin were generated by immunizing mice with a synthetic polypeptide corresponding to the 74 amino acids of predicted mature eotaxin (amino acids 24-97). Female Balb/C mice were immunized with 50 µg of the polypeptide in PBS 3 times at 2 week intervals. Mice were injected intra-peritoneally with the polypeptide, using Freund's complete (first injection) and incomplete adjuvant (second injection). The final immunization was injected intravenously without adjuvant.

One successful fusion was performed which generated over 5,000 hybridomas. Four days after the final injection, the spleen was removed and a single cell suspension prepared in serum free DMEM media. These cells were fused with the hybridoma fusion partner SP2/0, according to Galfre, G. et al. (Galfre, G. et al., *Nature*, 266: 550-552 (1977)). 20 ml of spleen cells and 20 ml of SP2/0 were combined, spun at 800 g for 5 min and the media removed. A solution of 50% Polyethylene glycol 1500 (Boehringer Mannheim, Indianapolis, Ind.) prewarmed to 37° C. was added to the cell pellet over 2 min, followed by 10 ml of DMEM media over 3 min. The cell suspension was spun at 400 g for 3 min and the supernatant removed. The pellet was resuspended gently in DMEM media containing 20% fetal calf serum, 2 mM L-glutamine, 100 units/ml penicillin, 100 µg/ml streptomycin sulfate, and HAT selection media (Boehringer Mannheim, Indianapolis, Ind.). Cells were plated into 96 well flat bottom microtiter plates at 200 µl/well.

Ten days later, supernatants from the wells were screened for reactivity against the human eotaxin polypeptide using an enzyme-labeled anti-mouse antibody (Horseradish peroxidase-labeled anti-mouse IgG) (Jackson) in an ELISA assay (*Current Protocols in Immunology*, 1992, Coligan, J. E., A. M. Kruisbeek, D. H. Margulies, E. M. Shevach, and W. Strober, Editors, (John Wiley and Sons, New York, N.Y.), Unit 2.1.3). Approximately 50 mAbs were selected that showed strong reactivity against the synthetic polypeptide. Hybridomas of interest were subcloned using limiting dilution.

Western Blot Analysis Using Anti-Eotaxin Monoclonal Antibody 6H9

The specificity of mAb 6H9 for human Eotaxin was confirmed by Western blot analysis. 2 µg each of various chemokines (MCP-1, MCP-2, MCP-3, RANTES, Eotaxin, MIP-1β, or MIP-1β) were mixed with non-reducing sample buffer, boiled, and applied to individual lanes of an SDS-polyacrylamide gel. Gels were run using a Biorad Mini-Protean II cell, and transfer of proteins to nitrocellulose was performed for 1 hr using 100V. SDS-PAGE and Western blotting were performed as described in *Current Protocols in Immunology*, Unit 8, Coligan et al., Eds., (John Wiley & Sons, New York, N.Y.), 1992, except that pre-poured 10-20% polyacrylamide gradient gels were used (BioRad, Hercules, Calif.). The nitrocellulose membranes were incubated with monoclonal antibody 6H9 as primary antibody for 1 hr, washed, and reacted with goat anti-mouse Ig conjugated with horseradish peroxidase (Jackson Labs), as described in *Current Protocols in Immunology*, 1992, Coligan, J. E., A. M. Kruisbeek, D. H. Margulies, E. M. Shevach, and W. Strober, Editors, (John Wiley and Sons, New York, N.Y.), Unit 8.10.7. Reactive bands were visualized using diaminobenzidene as the chromagen.

Monoclonal antibody 6H9 reacted with a band of approximately 6 kDa present in the lane containing synthetic eotaxin (predicted mature protein consisting of amino acids 24-97), but was not reactive with any of the other chemokines tested, including MCP-1, MCP-2, MCP-3, RANTES, MIP-1α, and MIP-1β.

Anti-eotaxin Monoclonal Antibodies Inhibit Eotaxin Binding to Eosinophils

Antibody-mediated Inhibition of Eotaxin Binding

Eighteen monoclonal antibodies selected by ELISA were tested for their ability to block eotaxin binding to its receptor on eosinophils. Binding buffer consisted of 50 mM HEPES, 1 mM $CaCl_2$, 5 mM $MgCl_2$ and 0.5% BSA. 50 µl of tissue culture supernatant from eighteen different anti-eotaxin hybridomas were each incubated with 5 µl (10 nM) $^{125}$I-labeled eotaxin (prepared as described in Example 6) at room temperature for 10 minutes. 50 µl ($5\times10^5$ cells) of purified human eosinophils (see Example 4) were then added, final volume was adjusted to 200 µl with binding buffer, and binding was carried out at room temperature for 60 minutes. As negative controls, 50 µl of culture medium (no antibody) or an anti-IL-8 receptor B antibody were added in lieu of anti-eotaxin antibody. At the end of incubation, cells were washed 3 times in binding buffer plus 0.5 M NaCl. The cell pellets were transferred into LP3 tubes and counted in a gamma counter.

Figure 13A:
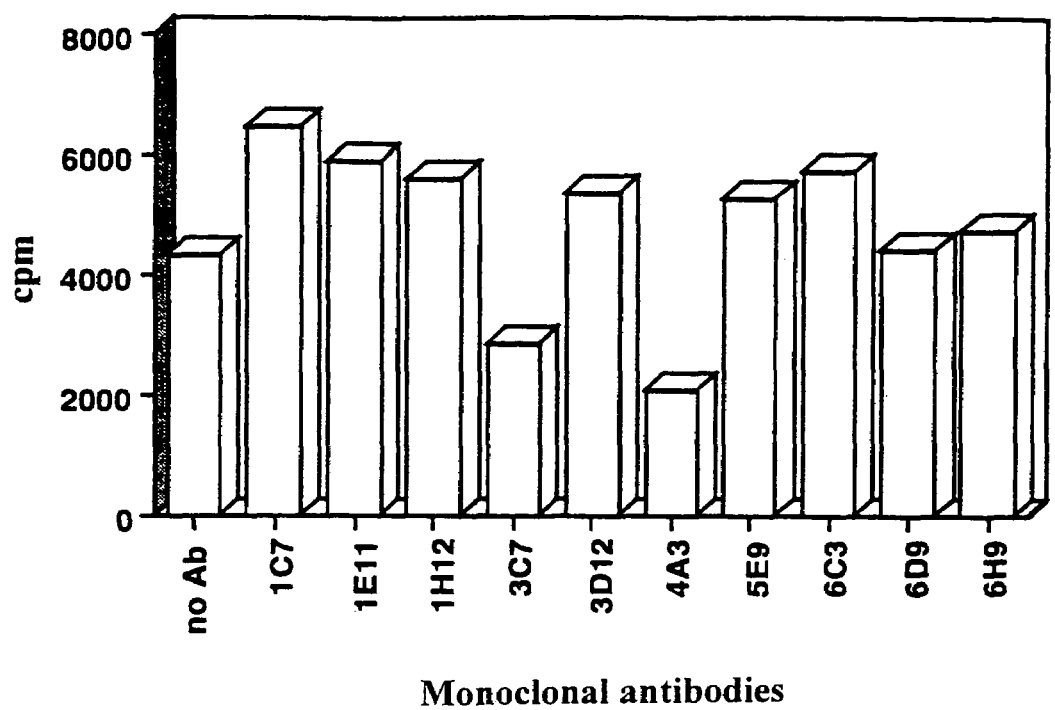
FIGS. 13A-13B are histograms illustrating the effect of anti-eotaxin monoclonal antibodies on eotaxin binding to purified human eosinophils. 50 μl of tissue culture supernatants from anti-eotaxin hybridomas were incubated with 5 μl (10 nM) radiolabeled eotaxin at room temperature for 10 minutes. Purified human eosinophils were then added, and binding was determined.
Figure 13B:
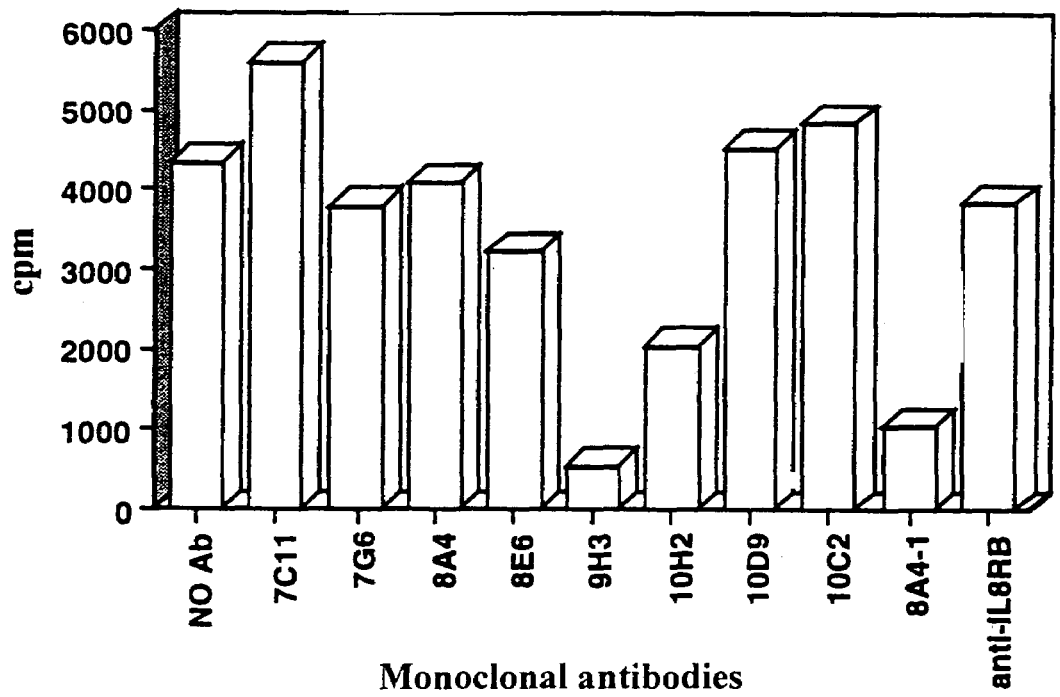

Of eighteen anti-eotaxin monoclonal antibodies tested, five showed significant inhibition of ligand binding (FIGS. 13A-13B; 3C7, 4A3, 9H3, 10H2, and 8A4-1).

Example 9

Upregulation of Eotaxin Expression at a Site of Eosinophil Involvement

Immunohistochemical analysis for human eotaxin protein was performed on formalin-fixed, paraffin-embedded samples of human nasal polyps and adjacent uninvolved nasal mucosa using techniques previously described (Ringler, D. J. et al., *Lab. Invest.*, 56: 313 (1987); Ringler, D. J. et al, *Clin. Immunol. Immunopathol.*, 49: 349 (1988); and Ringler, D. J. et al., *Am. J. Pathol.*, 126: 199 (1987)). Tissue was obtained from a human (believed to be an allergic rhinitis patient). Briefly, deparaffinized sections were post-fixed in 100% methanol for 5 minutes at 4° C., followed by blocking with PBS/10% goat serum for 30 minutes at room temperature. Anti-human eotaxin monoclonal antibody 6H9 (Example 8) or irrelevant mAb was then used as neat tissue culture supernatant, followed by biotinylated goat anti-mouse IgG (Vector Laboratories, Burlingame, Calif.), and subsequently by avidin-peroxidase complexes (Vector Laboratories, Burlingame, Calif.). Diaminobenzidine (DAB) was used as the chromagen.

There was a direct correlation between eosinophil infiltration within the mucosa and submucosa of the polyp and eotaxin expression to resident cells and leukocytes. Specifically, in areas of eosinophil localization, there was an increase in the number of anti-eotaxin immunoreactive macrophages, mast cells, epithelial cells, and eosinophils, and when compared to uninvolved nasal mucosa, a concomitant increase in staining intensity. These results were confirmed using anti-eotaxin monoclonal antibodies designated 6D6, 5H2, 5E9 and 1H12 (Example 8). The colocalization of elevated levels of eotaxin and eosinophils in inflamed tissue, as assessed immunohistologically with anti-eotaxin monoclonal antibodies supports the in vivo significance of eotaxin to the process of inflammation.

Example 10

Protocol for Eosinophil Recruitment to Skin

A male adult rhesus monkey was injected intradermally at 9 sites on the back with 0.1 ml of the following:
10, 100 or 1000 pmol of eotaxin in buffer
10, 100 or 1000 pmol of RANTES in buffer
10, 100 or 1000 pmol of bovine serum albumin (BSA) in buffer Buffer was Dulbecco's Phosphate buffered saline. Full-thickness skin biopsies (6 mm) were taken from these sites at 4 hours post-injection. These tissues were fixed in formalin, embedded in paraffin and sectioned for histological analysis by staining with hematoxylin and eosin.

Figure 14:
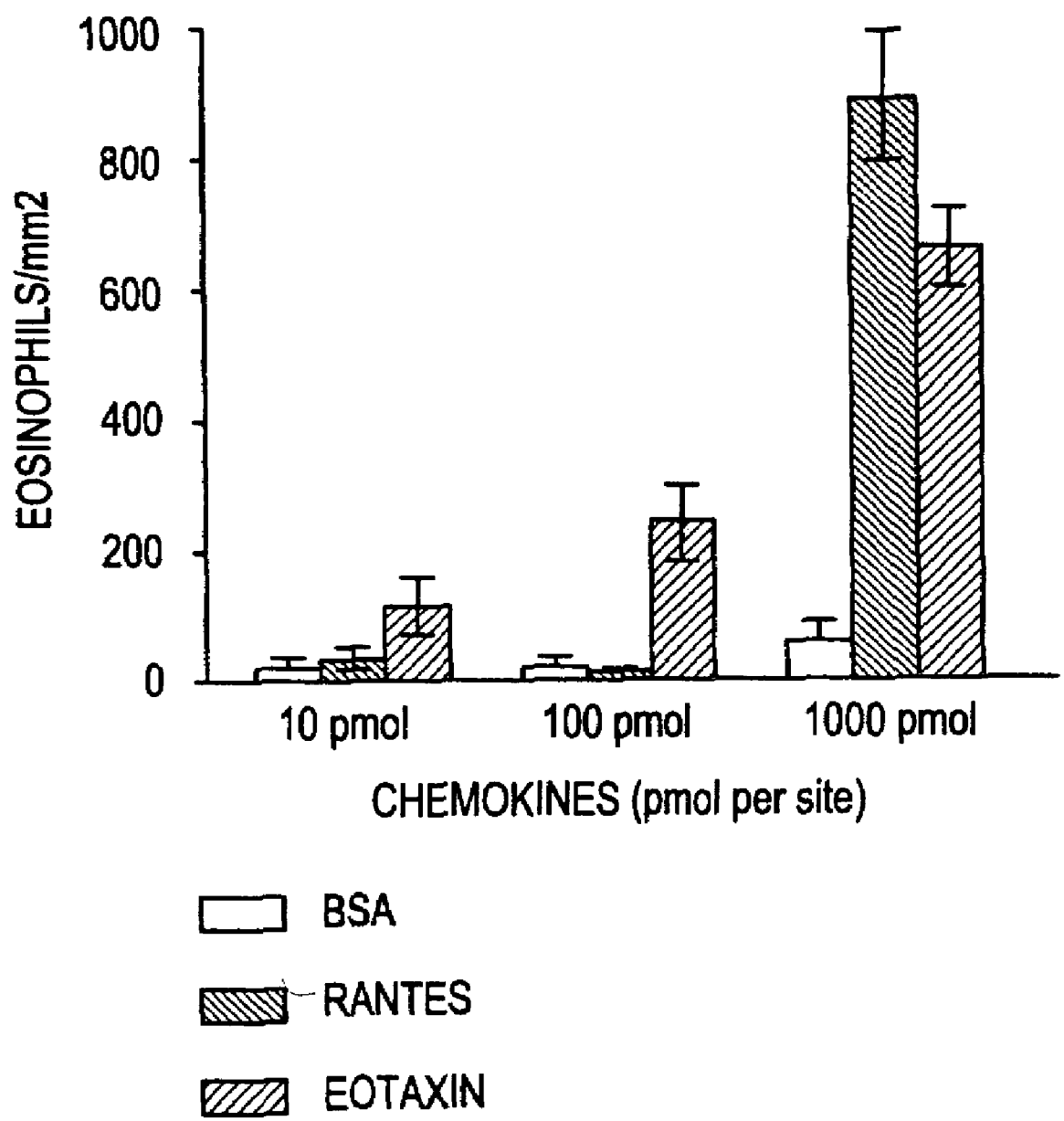
FIG. 14 is a bar graph of the number of eosinophils recruited to skin injection sites in rhesus monkeys. Skin biopsies (6 mm) were taken 4 hours after injection of control (BSA), RANTES or synthetic human eotaxin at the 10, 100 or 1000 pmol doses/site. The results are expressed as the number of cells recruited per $mm^2$ as determined by computer assisted morphometrics analysis.

Quantitative, computer-assisted, morphometric analysis of skin sections was performed using a Leica Quantimet 500 Image Analyzer. The relative density (number cells/area$^2$) of eosinophils was enumerated on at least 5 random fields/sections just adjacent to the post-capillary venules of the superficial vascular plexus. Cells were selected based on the color wavelength generated from eosin-stained cytoplasmic granules of eosinophils, and color selection criteria were identical on all sections analyzed. The number of eosinophils/area$^2$ $(mm)$ of dermis was calculated as the mean ±1 SEM and graphically depicted (FIG. 14).

Results

The results showed no recruitment of eosinophils with BSA at the 10 or 100 pmol doses, and only a rare isolated eosinophil at 1000 pmol. The greatest eosinophil recruitment was observed at the injection site for 1000 pmol of human eotaxin, which was characterized histologically by foci consisting of 5-10 eosinophils adjacent to the postcapillary venules of the superficial vascular plexus in the dermis, as well as clusters of eosinophils scattered throughout the dermal collagen bundles. RANTES elicited a substantially (approximately 10-fold) lower response at 100 pmol, with insignificant recruitment at the 10 pmol dose (FIG. 14).

Equivalents

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. Isolated human eotaxin or a fragment thereof, said human eotaxin comprising the amino acid sequence encoded by a nucleic acid comprising the nucleotide sequence of SEQ ID NO:1, wherein said fragment can attract eosinophils and/or induce eosinophil accumulation, without substantially attracting or inducing accumulation of neutrophils or monocytes.

2. The isolated human eotaxin or a fragment thereof of claim 1, wherein said human eotaxin or fragment thereof is labeled with a detectable label.

3. The isolated human eotaxin or a fragment thereof of claim 2, wherein said label is a fluorescent label or isotope label.

4. The isolated human eotaxin or a fragment thereof of claim 1, wherein said eotaxin or fragment thereof is produced by chemical synthesis.

5. The isolated human eotaxin or a fragment thereof of claim 1, wherein said eotaxin or fragment thereof is recombinant.

6. The isolated human eotaxin of claim 1.

7. An essentially pure eotaxin polypeptide comprising the amino acid sequence set forth in SEQ ID NO:2.

8. An isolated human eotaxin or fragment of said human eotaxin, wherein said human eotaxin comprises an amino acid sequence which shares at least 95% amino acid sequence similarity with amino acids 24-97 of SEQ ID NO:4, and wherein said human eotaxin or fragment can attract eosinophils and/or induce eosinophil accumulation, without substantially attracting or inducing accumulation of neutrophils or monocytes.

9. The isolated human eotaxin or fragment of said human eotaxin of claim 8, wherein said human eotaxin or fragment is labeled with a detectable label.

10. The isolated human eotaxin or fragment of said human eotaxin of claim 9, wherein said label is a fluorescent label or isotope label.

11. The isolated human eotaxin or fragment of said human eotaxin of claim 8, wherein said eotaxin is produced by chemical synthesis.

12. The isolated human eotaxin or fragment of said human eotaxin of claim 8, wherein said eotaxin is recombinant.

13. The isolated human eotaxin of claim 8.

14. The isolated human eotaxin of claim 13, wherein said eotaxin is labeled with a detectable label.

15. The isolated human eotaxin of claim 14, wherein said label is a fluorescent label or isotope label.

16. The isolated human eotaxin of claim 13, wherein said eotaxin is produced by chemical synthesis.

17. The isolated human eotaxin of claim 13, wherein said eotaxin is recombinant.

18. The isolated human eotaxin or fragment of said human eotaxin of claim 8, wherein said human eotaxin or said fragment comprises amino acids 24-97 or SEQ ID NO:4.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 2730 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(465..539, 1749..1861, 2237..2339)

(xi) SEQUENCE DESCRIPTION: SEQ ID NO: 1:

```
TCAAGACACA GTGTACACAG GAATCAAGGA AGGTCTTAGA TCGACTCATC CCCCAAGGCC        60

TTGGTTTCCT TGCTCCTTTC CCCAACTACA GGTGTTTCAT TTCAACTCAT CCCCTAGGG        120

CTTGGTTTTC TTGCTCTCTT CCCCCACTAC AGATGTTTAA CTTCATTTCA TAACCACAT        180

TTCCCCTCCT TTTCCAAGGC AAGATCCAGA TGGATTAAAA AATGTACCAA GTCCCTACT        240

GCTTGCCTCT CTTCTGTTCT GCTTGACTTC CTAGGATCTG GAATCTGGTC AGCAATCAG        300

AATCCCTTCA TCGTGACCCC CGCATGGGCA AAGGCTTCCC TGGAATCTCC CACACTGTC        360

GCTCCCTATA AAAGGCAGGC AGATGGGCCA GAGGAGCAGA GAGGCTGAGA CCAACCCAG        420

AACCACCACC TCTCACGCCA AAGCTCACAC CTTCAGCCTC CAAC ATG AAG GTC TCC        476
                                                Met Lys Val Ser
```

```
GCA GCA CTT CTG TGG CTG CTC ATA GCA GCT GCC TTC AGC CCC CAG       524
Ala Ala Leu Leu Trp Leu Leu Leu Ile Ala Ala Ala Phe Ser Pro Gln
  5              10                  15                  20

GGG CTC GCT GGG CCA GGTAAGCCCC CCAACTCCTT ACAGGAAAGG TAAGGTAACC   579
Gly Leu Ala Gly Pro
             25

ACCTCCAGAG CTACTAGGTC AGCAAGAATC TTTACAGACT CACTGCAAAT TCTCCATTT  639

AAAAATAGGG AAACAGGTTT TGTGGGTGGA CAAGAAATGC CTCAACCTCA CATCCAGTC  699

CTGGAAGAGC CAGAACTAGA AAGCTCCCGA GTCTTTTCCC CACATTCAAG AGGGTTGCT  759

GGCGCATCCT TACCCAGCTA TCCTCACAGT GTTTGGGAAT GGGGAATGGC TCTGTCTTA  819

TGTGGGCATG GTGGGCATTT TTGGCAGTGG GAGAGAAGGA AAATCTGTTG ATTAGAAGC  879

CAGTATGTTA ATTCGACTCC AGGACAGCTT TCAGAGACAG TGGCTAAGAG AGAAGAACG  939

GGTCCCAGGG GGATCTCTTG AGGTGACTTA TTTTGACACT CTTTGGGAAA CGTTATCTA  999

GAGATTTGTT CCATAACTCA TTTTCCCATA CTCTGGTGAC AAATTTACTG AGTGTATC   1059

TCCCACTGAG CCAGTGCATA GCATGGTAAC AAACAGTCTA AATTATCAAT GACTTAAC   1119

AATTAACTAA ATTAACAAAA GTTACTTTCT CACTTGTACT AAATATCTAT AATGTATG   1179

CTCAGGCTTC TGCATTTTAT ACTCAGGATT CTAGACTGAT GGAGAAGTTG CCCATGTG   1239

GGAACATTGA TGGATACTGT GATAAGCAGA AGAAGCTCTC AGGAGTCTTG CATAGGCA   1299

GCACTGTGGC TCAAAAATGA CACCCATCAC TTTGTCTCCT TCTTTATTGA TCAAAACT   1359

TTAATGCCTC CAACCAAACA AAAGTGGCCA AGAAATGCAA GTCTACCTTG TGTCTCAA   1419

CAGAGGATGG AGATATTTGG TGAAAATTAC CATGACCATC ACATGGCCAC GTAGGTCT   1479

ATAATGACAG GCTAGCATTT GTCACATTGA CCAAGCTTTG TCCATACACT CTACAGTA   1539

GATGAGTCCT CAGTGCACAG GGGAGGATGC TGAAGAGACA GGACAGCATC CTCCAGAC   1599

ATTTGACTTC AGAGCAGAGG GATTCTCCCT CCACCTCTCG CAATTCCTTG CTTTCTCC   1659

ACTTCCTTTA CAAAGTCATG CTTGGAAATG TCTATGTATC ATCATGTGGC TCATTTTT   1719

CTCTGTTCAT TTTTTTTCCC CAAAATTCA GCT TCT GTC CCA ACC ACC TGC TGC  1772
                                Ala Ser Val Pro Thr Thr Cys Cys
                                                         30

TTT AAC CTG GCC AAT AGG AAG ATA CCC CTT CAG CGA CTA GAG AGC TAC  1820
Phe Asn Leu Ala Asn Arg Lys Ile Pro Leu Gln Arg Leu Glu Ser Tyr
 35                  40                  45

AGG AGA ATC ACC AGT GGC AAA TGT CCC CAG AAA GCT GTG AT           1861
Arg Arg Ile Thr Ser Gly Lys Cys Pro Gln Lys Ala Val Ile
 50                  55                  60

GTAAGTAAAT AAAGTTCACC CTCCCCTAGA CAAAAAAATA ATGTCTAGGG CACAGAGT   1921

AGAACTGTGT CACAGTTGCT GGGAGTCATA GACTCTGATA GTTTGACCTC TATGGTCC   1981

TTCATTAATT TTCACAAGTG TGTGCACTCC CAGCTCCCTG CCTGGGAGAT TCGTGTAG   2041

ATATCAATTT CTTCAAGTCA AGAGCAAAGA TGGTTTTACT GGGCCTTTAA GAGCAGCA   2101

TAACCCAAGA GTCTCATCCT TCCTCCTCTC CGTAGCAACC CTTTGTCCAG GGCAGAT    2161

TCCTTAAATA TTTAGGGTCA AATGGGCAGA ATTTTCAAAA ACAATCCTTC CAATTGCA   2221

CTGTATCTCC CACAG C TTC AAG ACC AAA CTG GCC AAG GAT ATC TGT GCC   2270
                Phe Lys Thr Lys Leu Ala Lys Asp Ile Cys Ala
                             65                  70

GAC CCC AAG AAG AAG TGG GTG CAG GAT TCC ATG AAG TAT CTG GAC CAA  2318
Asp Pro Lys Lys Lys Trp Val Gln Asp Ser Met Lys Tyr Leu Asp Gln
 75                  80                  85                  90
```

```
AAA TCT CCA ACT CCA AAG CCA TAAATAATCA CCATTTTTGA AACCAAACCA      2369
Lys Ser Pro Thr Pro Lys Pro
                95

GAGCCTGATG TTGCCTAATT TGTTTTCCCT TCTTACAATG CATTCTGAGG TAACCTCA    2429

ATCAGTCCAA AGGGCATGGG TTTTATTATA TATATATATA TTTTTTTTTT AAAAAAAA    2489

GTATTGCATT TAATTTATTG AGGCTTTAAA ACTTATCCTC CATGATATCA GTTATTTT    2549

AACTGTAAGC TTTGTCAGAT TCTTTACCCC CTGGGAGCCC CAATTCGATC CCCTGTCA    2609

TGAACCCAAA GTGTGACTCA TTAAATGGAA GTAAATGTTG TTTTAGGAAT ACATAAAG    2669

TGTCGATATT TATTATAGTC ACTAGTTGTA ATTTTTTTGT GGGAAATCCA CACTGAGC    2729

A                                                                 2730

(2) INFORMATION FOR SEQ ID NO: 2:

(i) SEQUENCE CHARACTERISTICS:
        (A) LENGTH: 97 amino acids
        (B) TYPE: amino acid
        (D) TOPOLOGY: linear (ii) MOLECULE TYPE: protein (xi) SEQUENCE DESCRIPTION: SEQ ID NO: 2:

Met Lys Val Ser Ala Ala Leu Leu Trp Leu Leu Leu Ile Ala Ala Ala
 1               5                   10                  15

Phe Ser Pro Gln Gly Leu Ala Gly Pro Ala Ser Val Pro Thr Thr Cys
                20                  25                  30

Cys Phe Asn Leu Ala Asn Arg Lys Ile Pro Leu Gln Arg Leu Glu Ser
            35                  40                  45

Tyr Arg Arg Ile Thr Ser Gly Lys Cys Pro Gln Lys Ala Val Ile Phe
        50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Gln Lys Ser Pro Thr Pro Lys
                85                  90                  95

Pro (2) INFORMATION FOR SEQ ID NO: 3:

(i) SEQUENCE CHARACTERISTICS:
        (A) LENGTH: 294 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..291

(xi) SEQUENCE DESCRIPTION: SEQ ID NO: 3:

ATG AAG GTC TCC GCA GCA CTT CTG TGG CTG CTG CTC ATA GCA GCT GCC     48
Met Lys Val Ser Ala Ala Leu Leu Trp Leu Leu Leu Ile Ala Ala Ala
 1               5                   10                  15

TTC AGC CCC CAG GGG CTC GCT GGG CCA GCT TCT GTC CCA ACC ACC TGC     96
Phe Ser Pro Gln Gly Leu Ala Gly Pro Ala Ser Val Pro Thr Thr Cys
                20                  25                  30

TGC TTT AAC CTG GCC AAT AGG AAG ATA CCC CTT CAG CGA CTA GAG AGC    144
Cys Phe Asn Leu Ala Asn Arg Lys Ile Pro Leu Gln Arg Leu Glu Ser
            35                  40                  45
```

```
TAC AGG AGA ATC ACC AGT GGC AAA TGT CCC CAG AAA GCT GTG ATC TTC    192
Tyr Arg Arg Ile Thr Ser Gly Lys Cys Pro Gln Lys Ala Val Ile Phe
    50                  55                  60

AAG ACC AAA CTG GCC AAG GAT ATC TGT GCC GAC CCC AAG AAG AAG TGG    240
Lys Thr Lys Leu Ala Lys Asp Ile Cys Ala Asp Pro Lys Lys Lys Trp
 65                  70                  75                  80

GTG CAG GAT TCC ATG AAG TAT CTG GAC CAA AAA TCT CCA ACT CCA AAG    288
Val Gln Asp Ser Met Lys Tyr Leu Asp Gln Lys Ser Pro Thr Pro Lys
                 85                  90                  95

CCA TAA                                                            294
Pro
```

(2) INFORMATION FOR SEQ ID NO: 4:

(i) SEQUENCE CHARACTERISTICS:
        (A) LENGTH: 97 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Lys Val Ser Ala Ala Leu Leu Trp Leu Leu Leu Ile Ala Ala Ala
 1               5                  10                  15

Phe Ser Pro Gln Gly Leu Ala Gly Pro Ala Ser Val Pro Thr Thr Cys
                 20                  25                  30

Cys Phe Asn Leu Ala Asn Arg Lys Ile Pro Leu Gln Arg Leu Glu Ser
                 35                  40                  45

Tyr Arg Arg Ile Thr Ser Gly Lys Cys Pro Gln Lys Ala Val Ile Phe
    50                  55                  60

Lys Thr Lys Leu Ala Lys Asp Ile Cys Ala Asp Pro Lys Lys Lys Trp
 65                  70                  75                  80

Val Gln Asp Ser Met Lys Tyr Leu Asp Gln Lys Ser Pro Thr Pro Lys
                 85                  90                  95

Pro
```

(2) INFORMATION FOR SEQ ID NO: 5:

(i) SEQUENCE CHARACTERISTICS:
        (A) LENGTH: 1689 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 5:

```
AATCCTTTTC CTGGCACCTC TGATATCCTT TTGAAATTCA TGTTAAAGAA TCCCTAGGCT     60

GCTATCACAT GTGGCATCTT TGTTGAGTAC ATGAATAAAT CAACTGGTGT GTTTTACGA    120

GGATGATTAT GCTTCATTGT GGGATTGTAT TTTTCTTCTT CTATCACAGG GAGAAGTGA    180

ATGACAACCT CACTAGATAC AGTTGAGACC TTTGGTACCA CATCCTACTA TGATGACGT    240

GGCCTGCTCT GTGAAAAAGC TGATACCAGA GCACTGATGG CCCAGTTTGT GCCCCCGCT    300

TACTCCCTGG TGTTCACTGT GGGCCTCTTG GCAATGTGG TGGTGGTGAT GATCCTCAT     360

AAATACAGGA GGCTCCGAAT TATGACCAAC ATCTACCTGC TCAACCTGGC CATTTCGGA    420

CTGCTCTTCC TCGTCACCCT TCCATTCTGG ATCCACTATG TCAGGGGGCA TAACTGGGT    480

TTTGGCCATG GCATGTGTAA GCTCCTCTCA GGGTTTTATC ACACAGGCTT GTACAGCGA    540

ATCTTTTTCA TAATCCTGCT GACAATCGAC AGGTACCTGG CCATTGTCCA TGCTGTGTT    600
```

```
GCCCTTCGAG CCCGGACTGT CACTTTTGGT GTCATCACCA GCATCGTCAC CTGGGGCCT      660

GCAGTGCTAG CAGCTCTTCC TGAATTTATC TTCTATGAGA CTGAAGAGTT GTTTGAAGA      720

ACTCTTTGCA GTGCTCTTTA CCCAGAGGAT ACAGTATATA GCTGGAGGCA TTTCCACAC      780

CTGAGAATGA CCATCTTCTG TCTCGTTCTC CCTCTGCTCG TTATGGCCAT CTGCTACAC      840

GGAATCATCA AAACGCTGCT GAGGTGCCCC AGTAAAAAAA AGTACAAGGC CATCCGGCT      900

ATTTTTGTCA TCATGGCGGT GTTTTTCATT TTCTGGACAC CCTACAATGT GGCTATCCT      960

CTCTCTTCCT ATCAATCCAT CTTATTTGGA AATGACTGTG AGCGGACGAA GCATCTGG     1020

CTGGTCATGC TGGTGACAGA GGTGATCGCC TACTCCCACT GCTGCATGAA CCCGGTGA     1080

TACGCCTTTG TTGGAGAGAG GTTCCGGAAG TACCTGCGCC ACTTCTTCCA CAGGCACT     1140

CTCATGCACC TGGGCAGATA CATCCCATTC CTTCCTAGTG AGAAGCTGGA AAGAACCA     1200

TCTGTCTCTC CATCCACAGC AGAGCCGGAA CTCTCTATTG TGTTTTAGGT AGATGCAG     1260

AATTGCCTAA AGAGGAAGGA CCAAGGAGAT NAAGCAAACA CATTAAGCCT TCCACACT     1320

CCTCTAAAAC AGTCCTTCAA ACCTTCCAGT GCAACACTGA AGCTCTTAAG ACACTGAA     1380

ATACACACAG CAGTAGCAGT AGATGCATGT ACCCTAAGGT CATTACCACA GGCCAGGG     1440

GGGCAGCGTA CTCATCATCA ACCTAAAAAG CAGAGCTTTG CTTCTCTCTC TAAAATGA     1500

TACCTATATT TTAATGCACC TGAATGTTAG ATAGTTACTA TATGCCGCTA CAAAAAGG     1560

AAACTTTTTA TATTTTATAC ATTAACTTCA GCCAGCTATT ATATAAATAA AACATTTT     1620

CACAATACAA TAAGTTAACT ATTTTATTTT CTAATGTGCC TAGTTCTTTC CCTGCTTA     1680

GAAAAGCTT                                                          1689

(2) INFORMATION FOR SEQ ID NO: 6:

(i) SEQUENCE CHARACTERISTICS:
        (A) LENGTH: 355 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 6:

Met Thr Thr Ser Leu Asp Thr Val Glu Thr Phe Gly Thr Thr Ser Ty
1               5                   10                  15

Tyr Asp Asp Val Gly Leu Leu Cys Glu Lys Ala Asp Thr Arg Ala Le
                20                  25                  30

Met Ala Gln Phe Val Pro Pro Leu Tyr Ser Leu Val Phe Thr Phe Gl
            35                  40                  45

Leu Leu Gly Asn Val Val Val Met Ile Leu Ile Lys Tyr Arg Ar
        50                  55                  60

Leu Arg Ile Met Thr Asn Ile Tyr Leu Leu Asn Leu Ala Ile Ser As
65              70                  75                  80

Leu Leu Phe Leu Val Thr Leu Pro Phe Trp Ile His Tyr Val Arg Gl
                85                  90                  95

His Asn Trp Val Phe Gly His Gly Met Cys Lys Leu Leu Ser Gly Ph
            100                 105                 110

Tyr His Thr Gly Leu Tyr Ser Glu Ile Phe Phe Ile Ile Leu Leu Th
        115                 120                 125

Ile Asp Arg Tyr Leu Ala Ile Val His Ala Val Phe Ala Leu Arg Al
    130                 135                 140
```

```
Arg Thr Val Thr Phe Gly Val Ile Thr Ser Ile Val Thr Trp Gly Le
145                 150                 155                 160

Ala Val Leu Ala Ala Leu Pro Glu Phe Ile Phe Tyr Glu Thr Glu Gl
                165                 170                 175

Leu Phe Glu Glu Thr Leu Cys Ser Ala Leu Tyr Pro Gly Asp Thr Va
            180                 185                 190

Tyr Ser Trp Arg His Phe His Thr Leu Arg Met Thr Ile Phe Cys Le
        195                 200                 205

Val Leu Pro Leu Leu Val Met Ala Ile Cys Tyr Thr Gly Ile Ile Ly
    210                 215                 220

Thr Leu Leu Arg Cys Pro Ser Lys Lys Tyr Lys Ala Ile Arg Le
225                 230                 235                 240

Ile Phe Val Ile Met Ala Val Phe Phe Ile Phe Trp Thr Pro Tyr As
                245                 250                 255

Val Ala Ile Leu Leu Ser Ser Tyr Gln Ser Ile Leu Phe Gly Asn As
                260                 265                 270

Cys Glu Arg Thr Lys His Leu Asp Leu Val Met Leu Val Thr Glu Va
            275                 280                 285

Ile Ala Tyr Ser His Cys Cys Met Asn Pro Val Ile Tyr Ala Phe Va
        290                 295                 300

Gly Glu Arg Phe Arg Lys Tyr Leu Arg His Phe Phe His Arg His Le
305                 310                 315                 320

Leu Met His Leu Gly Arg Tyr Ile Pro Phe Leu Pro Ser Glu Lys Le
                325                 330                 335

Glu Arg Thr Ser Ser Val Ser Pro Ser Thr Ala Glu Pro Glu Leu Se
                340                 345                 350

Ile Val Phe
        355

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 7:

GGATCCAACA TGAAGGTCTC CG                                            22

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 8:

GAATTCTTAT GGCTTTGGAG TTGGAG                                        26

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ix) FEATURE:
        (A) NAME/KEY: modified_base
```

```
        (B) LOCATION: 9
        (D) OTHER INFORMATION: /mod_base= i (ix) FEATURE:
        (A) NAME/KEY: modified_base
        (B) LOCATION: 14
        (D) OTHER INFORMATION: /mod_base= i (xi) SEQUENCE DESCRIPTION: SEQ ID NO: 9:

ACCTGGCCNT GGCNGACCTM CTCTT                                          25

(2) INFORMATION FOR SEQ ID NO: 10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 10
        (D) OTHER INFORMATION: /mod_base= i (xi) SEQUENCE DESCRIPTION: SEQ ID NO: 10:

GGCRTGGACN ATGGCCAGGT ARCGGTC                                        27

(2) INFORMATION FOR SEQ ID NO: 11:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 16..48

(xi) SEQUENCE DESCRIPTION: SEQ ID NO: 11:

AAGCTTCCAG CAGCC ATG GAC TAC AAG GAC GAC GAT GAC AAA GAA TTC         48
                Met Asp Tyr Lys Asp Asp Asp Asp Lys Glu Phe
                 1               5                      10

(2) INFORMATION FOR SEQ ID NO: 12:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 12:

Met Asp Tyr Lys Asp Asp Asp Asp Lys Glu Phe
 1               5                      10

(2) INFORMATION FOR SEQ ID NO: 13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 13:

TTAAGAATTC ACAACCTCAC TAGATAC                                        27

(2) INFORMATION FOR SEQ ID NO: 14:
```

```
        (i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO: 14:

CATAGTGGAT CCAGAATG                                                              18
```